United States Patent
Liu et al.

(10) Patent No.: US 12,331,038 B2
(45) Date of Patent: Jun. 17, 2025

(54) HEXONE GLUCOKINASE INHIBITOR AND USE THEREOF

(71) Applicants: SHANDONG XUANZHU PHARMA CO., LTD., Jinan (CN); XUANZHU BIOPHARMACEUTICAL CO., LTD., Shijiazhuang (CN)

(72) Inventors: Bin Liu, Jinan (CN); Bo Chen, Jinan (CN)

(73) Assignees: SHANDONG XUANZHU PHARMA CO., LTD., Jinan (CN); XUANZHU BIOPHARMACEUTICAL CO., LTD., Shijiazhuang (CN)

(*) Notice: Subject to any disclaimer, the term of this patent is extended or adjusted under 35 U.S.C. 154(b) by 898 days.

(21) Appl. No.: 17/426,675

(22) PCT Filed: Jan. 22, 2020

(86) PCT No.: PCT/CN2020/073813
§ 371 (c)(1),
(2) Date: Jul. 29, 2021

(87) PCT Pub. No.: WO2020/156445
PCT Pub. Date: Aug. 6, 2020

(65) Prior Publication Data
US 2022/0106299 A1   Apr. 7, 2022

(30) Foreign Application Priority Data

Jan. 29, 2019   (CN) .................... 201910085547.9
Apr. 19, 2019   (CN) .................... 201910316417.1
Oct. 17, 2019   (CN) .................... 201910985433.X

(51) Int. Cl.
C07D 403/14    (2006.01)
C07D 401/14    (2006.01)
C07D 403/04    (2006.01)

(52) U.S. Cl.
CPC ......... C07D 403/14 (2013.01); C07D 401/14 (2013.01); C07D 403/04 (2013.01)

(58) Field of Classification Search
CPC ... C07D 403/14; C07D 401/14; C07D 403/04
See application file for complete search history.

(56) References Cited

U.S. PATENT DOCUMENTS

| | | | |
|---|---|---|---|
| 8,637,523 B2 | 1/2014 | Boy et al. | |
| 8,871,756 B2 | 10/2014 | Chen et al. | |
| 9,981,976 B2 | 5/2018 | Tahari et al. | |

FOREIGN PATENT DOCUMENTS

| | | | | |
|---|---|---|---|---|
| CN | 102939283 A | 2/2013 | | |
| CN | 107001377 A | 8/2017 | | |
| CN | 107406462 A | 11/2017 | | |
| CN | 108473469 A | 8/2018 | | |
| EA | 201390766 A1 | 11/2013 | | |
| EP | 3268373 B1 | 4/2022 | | |
| JP | 2013531040 A | 8/2013 | | |
| JP | 2014521709 A | 8/2014 | | |
| JP | 2017537118 A | 12/2017 | | |
| JP | 2018512399 A | 5/2018 | | |
| RU | 2011144763 A | 5/2013 | | |
| RU | 2696269 C1 | 8/2019 | | |
| WO | WO-2011078143 A1 | 6/2011 | | |
| WO | WO-2012103297 A1 | 8/2012 | | |
| WO | WO-2013020993 A1 | 2/2013 | | |
| WO | WO-2016091774 A1 | 6/2016 | | |
| WO | WO-2016142310 A1 * | 9/2016 | ......... | A61K 31/5383 |
| WO | WO-2018113584 A1 | 6/2018 | | |

(Continued)

OTHER PUBLICATIONS

International Search Report and Written Opinion of the International Searching Authority, issued in PCT/CN2020/073813, mailed Apr. 24, 2020; ISA/CN.
Canadian Office Action from corresponding Canadian Application No. 3,127,130 dated Oct. 3, 2022.
Japan Office Action from corresponding Japanese Application No. 2021-543534 dated Sep. 7, 2022.
Written Opinion from corresponding Singapore Application No. 11202107389S dated Oct. 11, 2022.
Chou, T.C., "Drug Combination Studies and Their Synergy Quantification Using the Chou-Talalay Method," Cancer Res; 70(2): 440-446 (2010).
The extended European Search Report for Application No. 20749439. 4-1110 PCT/CN2020073813, dated Sep. 24, 2021.

(Continued)

*Primary Examiner* — Marcos L Sznaidman
(74) *Attorney, Agent, or Firm* — Harness Dickey & Pierce P.L.C.

(57) ABSTRACT

The present invention relates to the technical field of pharmaceuticals, and in particular to a ketohexokinase inhibitor compound, a pharmaceutically acceptable salt, an ester or a stereoisomer thereof, a pharmaceutical composition and formulation containing the compound, the pharmaceutically acceptable salt, the ester or the stereoisomer thereof; a method for preparing the compound, the pharmaceutically acceptable salt, the ester or the stereoisomer thereof; and use of the compound, the pharmaceutically acceptable salt, the ester or the stereoisomer thereof in the manufacture of a medicament for treating and/or preventing KHK-mediated diseases and related conditions.

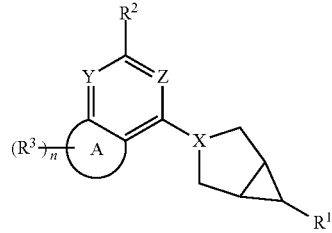

9 Claims, No Drawings

(56) References Cited

FOREIGN PATENT DOCUMENTS

WO  WO-2018232094 A1  12/2018
WO  WO-2019076358 A1  4/2019

OTHER PUBLICATIONS

Chinese Office Action for Application No. 202080008816.2 dated Apr. 13, 2022.
Chinese Search Report for Application No. 202080008816.2 dated Apr. 7, 2022.
Australian Examination Report for Application No. 2020214064 dated Dec. 8, 2021.
Aware, V. et al., "Cyclopentyl-pyrimidine based analogues as novel and potent IGF-1R inhibitor", European Journal of Medicinal Chemistry, 2015 vol. 92, pp. 246-256 [1].
CAS Registry No. 1312934-50-1; STN Entry Date Jul. 18, 2011.
CAS Registry No. 1538445-96-3; STN Entry Date Feb. 6, 2014.
CAS Registry No. 1312934-91-0; STN Entry Date Jul. 18, 2011.
CAS Registry No. 1824096-11-8; STN Entry Date Dec. 7, 2015.
CAS Registry No. 2023421-13-6; STN Entry Date Nov. 2, 2016.
CAS Registry No. 1865313-92-3; STN Entry Date Feb. 12, 2016.
CAS Registry No. 1935869-82-1; STN Entry Date Jul. 21, 2016.
Russian Office Action for Application No. 2021122641/04 dated May 13, 2022.
Russian Search Report for Application No. PCT/CN2020/073813 dated May 12, 2022.

* cited by examiner

HEXONE GLUCOKINASE INHIBITOR AND USE THEREOF

CROSS-REFERENCE TO RELATED APPLICATIONS

This application is a 371 U.S. National Stage of International Application No. PCT/CN2020/073813, filed on Jan. 22, 2020, which claims priority to Chinese Application No. 201910085547.9, filed on Jan. 29, 2019; Chinese Application No. 201910316417.1 filed on Apr. 19, 2019; and Chinese Application No. 201910985433.X, filed on Oct. 17, 2019. The entire disclosures of the above applications are incorporated herein by reference.

FIELD OF THE INVENTION

The present invention relates to the technical field of pharmaceuticals, and in particular to a ketohexokinase inhibitor compound, a pharmaceutically acceptable salt, an ester or a stereoisomer thereof; a pharmaceutical composition and formulation comprising the compound, the pharmaceutically acceptable salt, the ester or the stereoisomer thereof; a method for preparing the compound, the pharmaceutically acceptable salt, the ester or the stereoisomer thereof, and use of the compound, the pharmaceutically acceptable salt, the ester or the stereoisomer thereof in the manufacture of a medicament for treating and/or preventing KHK-mediated diseases and related conditions.

BACKGROUND OF THE INVENTION

NAFLD/NASH is a liver manifestation of metabolic syndrome. Changes in diet and lifestyle have led to the prevalence of obesity and metabolic syndromes in Western countries and many Asian countries, resulting in a significant increase in the incidence of NAFLD, which has become one of the public health issues of considerable concern. Nonalcoholic steatohepatitis (NASH) is the result of the further development of the simple fatty liver, which is pathologically manifested by lipid deposition, inflammatory cell infiltration, liver tissue necrosis and fibrotic lesions, and further by more severe liver cirrhosis and hepatocellular carcinoma (HCC). NAFLD not only affects the hepatobiliary system of patients, but also closely relates to insulin resistance, dyslipidemia, atherosclerosis, fat embolism, hematological system diseases and the like (Friedman S L et al., Nat Med, 2018, 24: 908-22). Because all the components of metabolic syndrome are related to liver fat content, patients suffering from metabolic syndrome should be assessed for NAFLD risk. Patients suffering from type II diabetes are accompanied by insulin resistance, obesity, dyslipidemia, and abnormal hepatic enzymes. Thus, NAFLD is also highly prevalent in people at risk of type II diabetes.

Due to the continuous increase in sugar (usually sucrose and high-fructose corn syrup) added in beverages and processed food, the content of fructose in modern people's diet has increased. High fructose intake has been shown to cause many undesirable metabolic effects. It plays a role in the development of obesity and metabolic syndrome, such as weight gain, hyperlipidemia, hypertension and insulin resistance ((a) Elliott S S, Keim N L, Stern J S, Teff K, Havel P J. Fructose, weight gain, and the insulin resistance syndrome; (b) Bray G A. Soft drink consumption and obesity: it is all about fructose, Current opinion in lipidology. 2010; 21(1): 51-7; (c) The American journal of clinical nutrition. 2002; 76(5): 911-22; and cardiovascular disease, The American journal of clinical nutrition. 2007; 86(4):899-906). Fructose promotes the occurrence and development of NAFLD, and aggravates the development and deterioration of NAFLD (Shi Hongbin et al., Relationship between Fructose and Non-alcoholic Fatty Liver Disease, Medical Recapitulate 2017 23(9), 1685-1689). Moreover, high fructose intake can increase the risk of NASH and advanced liver fibrosis ("2016 EASL (European Association for the Study of the Liver)-EASD (European Association for the Study of Diabetes)-EASO (European Association for the Study of Obesity) Clinical Practice Guidelines for the Management of Non-alcoholic Fatty Liver Disease"). Unlike glucose, the metabolism of fructose is not regulated by negative feedback. In comparison with other carbohydrates, fructose is metabolized preferentially, and its metabolism produces various reactions and signaling metabolites, which promote the progression of metabolic diseases. In the absence of KHK, weight gain and insulin resistance caused by fructose consumption are blocked (George Marek, Varinderpal Pannu, Prashanth Shanmugham, Brianna Pancione, Dominic Mascia, Sean Crosson, Takuji Ishimoto, and Yuri Y Sautin; Adiponectin Resistance and Proinflammatory Changes in the Visceral Adipose Tissue Induced by Fructose Consumption via Ketohexokinase-Dependent Pathway; Diabetes 2015; 64: 508-518). Reducing sugar/HFCS (high-fructose corn syrup) intake and/or blocking the production of uric acid contribute to reduce NAFLD and its downstream complications of liver cirrhosis and chronic liver disease (Thomas Jensen et al., Fruit and Sugar: A Major Mediator of Nonalcoholic Fatty Liver Disease, J Hepatol. 2018 May; 68(5): 1063-1075). Moreover, basic fructose diabetes, caused by human genetic mutagenesis, is a rare and harmless abnormality characterized by the appearance of fructose in the urine after ingestion of fructose-containing foods. The high prevalence of T2D, obesity, NAFLD/NASH, and related metabolic diseases such as cardiovascular diseases and brain stroke has led to an increase in the demand for both preventive health care and therapeutic intervention.

Ketohexokinase (also known as fructokinase) is the basic enzyme for fructose metabolism. KHK enzyme in the liver phosphorylates the C1 position of fructose with the assistance of ATP (adenosine triphosphate) to produce fructose-1-phosphate (F1P), which enters the normal metabolic pathway; at the same time, uric acid is produced from downstream of ATP. Human-derived Ketohexokinase (hKHK) expressed by two alternative mRNA spliceosomes encodes two different regioisomer enzymes KHK-A and KHK-C. KHK-C has a lower Km value, a higher Kcat value, and catalytic efficiency 405 times higher than KHK-A, indicating that KHK-C has a significantly higher affinity and ability to phosphorylate fructose than KHK-A. Although KHK-A is widely expressed while KHK-C is distributed in the liver, kidney, and intestines, KHK-C is the main metabolic site for fructose in vivo.

In the human body, endogenous fructose is produced by converting glucose to fructose through an intermediate sorbitol via the polyol pathway (Mingule A, et al., Endogenous fructose production and metabolism in the liver contributes to the development of metabolic syndrome, Nat Commun. 2013; 4: 2434), and the activity of this pathway increases with hyperglycemia. Studies have shown that KHK-knockout mice are protected from glucose-induced weight gain, insulin resistance and steatosis, indicating that endogenously produced fructose can contribute to insulin resistance and steatosis under hyperglycemia condition (Lanaspa, M A, et al., Nature Comm. 4, 2434, 2013). Fructose is the only common carbohydrate that produces uric acid during its metabolism. At the same time, fructose also stimulates the synthesis of uric acid from amino acid precursors. Therefore, it is speculated that inhibition of KHK is beneficial for many diseases in which changes in either or both of endogenous or intake fructose are involved.

Hepatic fructokinase deficiency is the basis of fructosuria. Contrary to this benign condition, the lack of aldolase B (the next enzyme in the metabolic pathway of fructose via KHK) leads to the accumulation of F1P during fructose intake and may lead to the fatal depletion of cellular ATP (hereditary fructose intolerance). In the fructose metabolism pathway, the enzyme responsible for breaking down F1P immediately downstream the KHK step is aldolase (ALDOB). The absence of this enzyme causes hereditary fructose intolerance (HFI), which is a rare disease that approximately 1 per 20,000 people suffers from the same. Such a mutation causes F1P accumulation and increased uric acid formation after ATP depletion, which collectively lead to hypoglycemia, hyperuricemia, lactic acidosis, and other metabolic disorders. HFI blocks the downstream metabolism of fructose and causes acute symptoms such as vomiting, severe hypoglycemia, diarrhea, and abdominal pain, and further causes long-term growth defects, liver and kidney damage, and potentially death (Ali M et al., J. Med. Genet. May 1998: 35(5); 353-365). Patients usually experience a year of survival before diagnosis, and the only treatment is to avoid fructose in the diet. However, the glucose in vivo is converted into endogenous fructose via the polyol pathway and metabolized in vivo, which is also a challenge to this treatment. The presence of fructose in most foods poses a challenge to diet. In addition to physical symptoms, many patients have to face emotional and social isolation due to their unusual diet, and must strictly keep to dietary restrictions (HFI-INFO Discussion Board, http://hfiinfo.proboards.com. accessed on Dec. 14, 2015). In addition, infusions containing fructose, sorbitol or invert sugar can endanger patient's life. There is a high unmet clinical need for this disease.

SUMMARY OF THE INVENTION

The purpose of the present invention is to provide a ketohexokinase inhibitor and its use. The particular technical solutions are as follows:

The present invention first provides a compound represented by the general formula (I), a pharmaceutically acceptable salt, an ester or a stereoisomer thereof:

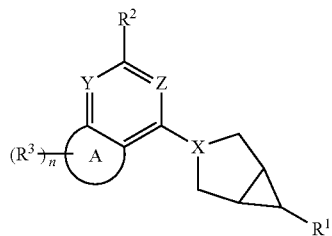

(I)

wherein,
X, Y, and Z are each independently selected from —$CR^4$— and —N—;
ring A is selected from 3-14 membered cycloalkyl, 3-14 membered heterocyclic group, 6-12 membered aryl and 5-12 membered heteroaryl;

$R^1$ is selected from hydrogen, halogen, nitro group, cyano group, -(L)$_m$-C(O)O$R^a$, -(L)$_m$-CON$R^aR^b$, -(L)$_m$-CONHSO$_2R^a$, -(L)$_m$-SO$_2R^a$, -(L)$_m$-SO$_2$NHCO$R^a$, -(L)$_m$-O$R^a$, -(L)$_m$-S$R^a$, -(L)$_m$-N$R^aR^b$, -(L)$_m$-C(O)$R^a$, -(L)$_m$-OC(O)$R^a$, -(L)$_m$-OC(O)O$R^a$, -(L)$_m$-OC(O)N$R^aR^b$, -(L)$_m$-N$R^a$C(O)$R^b$, -(L)$_m$-N$R^a$C(O)O$R^b$, -(L)$_m$-OS(O)$R^a$, -(L)$_m$-OS(O)O$R^a$, -(L)$_m$-OS(O)N$R^aR^b$, -(L)$_m$-S(O)N$R^aR^b$, -(L)$_m$-N$R^a$S(O)$R^b$, -(L)$_m$-OS(O)$_2R^a$, -(L)$_m$-S(O)$_2$N$R^aR^b$, -(L)$_m$-N$R^a$S(O)$_2R^b$; and the following groups optionally substituted with one or more Q1 groups: -(L)$_m$-C$_{1-6}$ alkyl, -(L)$_m$-C$_{1-6}$ alkoxy, -(L)$_m$-C$_{3-12}$ cycloalkyl, -(L)$_m$-C$_{3-12}$ heterocyclyl, -(L)$_m$-C$_{6-12}$ aryl and -(L)$_m$-C$_{5-12}$ heteroaryl;
L is selected from C$_{1-6}$ alkylene and halo C$_{1-6}$ alkylene;
$R^2$ is selected from the following groups optionally substituted by one or more Q2 groups: 3-12 membered heterocyclic group, 3-12 membered cycloalkyl group, 5-12 membered heteroaryl, 6-12 membered aryl, 5-12 membered spirocyclic group, 5-12 membered spiro heterocyclic group, 5-12 membered bridged group, 5-12 membered bridged heterocyclic group, N(C$_{1-6}$ alkyl)$_2$, N(C$_{1-6}$ alkyl) (C$_{3-8}$ cycloalkyl), NH(C$_{1-6}$ alkyl) and NH(C$_{3-8}$ cycloalkyl);
each $R^3$ is independently selected from hydrogen, halogen, nitro group, cyano group, amino group, hydroxyl, carboxy; and the following groups optionally substituted with one or more Q3 groups: C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-12 membered cycloalkyl group, 3-12 membered heterocyclic group, 6-12 membered aryl and 5-12 membered heteroaryl;
each $R^4$ is independently selected from hydrogen, cyano group, and the following groups optionally substituted with one or more Q4 groups: C$_{1-6}$ alkyl, —C(O)$R^a$, —C(O)O$R^a$, —C(O)N$R^aR^b$, —S(O)$R^a$, —S(O)O$R^a$, —S(O)N$R^aR^b$, —S(O)$_2R^a$, —S(O)$_2$O$R^a$, —S(O)$_2$N$R^aR^b$, 3-12 membered cycloalkyl, 3-12 membered heterocyclic group, 6-12 membered aryl and 5-12 membered heteroaryl;
each of $R^a$ and $R^b$ is independently selected from hydrogen, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl and halo C$_{1-6}$ alkoxy;
each of Q1, Q2, Q3 and Q4 groups is independently selected from hydroxyl, amino group, halogen, nitro group, cyano group, carboxy, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-10 membered cycloalkyl, 3-10 membered heterocyclic group, 6-10 membered aryl and 5-10 membered heteroaryl; and
m and n are each independently an integer from 0 to 8.

In certain embodiments, provided is said compound represented by the general formula (I), the pharmaceutically acceptable salt, the ester or the stereoisomer thereof:
wherein,
X, Y, and Z are each independently selected from —$CR^4$— and —N—;
ring A is selected from 3-12 membered cycloalkyl, 3-12 membered heterocyclic group, 6-10 membered aryl and 5-10 membered heteroaryl;
$R^1$ is selected from hydrogen, halogen, nitro group, cyano group, -(L)$_m$-C(O)O$R^a$, -(L)$_m$-CON$R^aR^b$, -(L)$_m$-CONHSO$_2R^a$, -(L)$_m$-SO$_2R^a$, -(L)$_m$-SO$_2$NHCO$R^a$, -(L)$_m$-O$R^a$, -(L)$_m$-S$R^a$, -(L)$_m$-N$R^aR^b$, -(L)$_m$-C(O)$R^a$, -(L)$_m$-OC(O)$R^a$, -(L)$_m$-OC(O)O$R^a$, -(L)$_m$-OC(O)

$NR^aR^b$, -(L)$_m$-NR$^a$C(O)R$^b$, -(L)$_m$-NR$^a$C(O)OR$^b$, -(L)$_m$-OS(O)R$^a$, -(L)$_m$-OS(O)OR$^a$, -(L)$_m$-OS(O)NR$^a$R$^b$, -(L)$_m$-S(O)NR$^a$R$^b$, -(L)$_m$-NR$^a$S(O)R$^b$, -(L)$_m$-OS(O)$_2$R$^a$, -(L)$_m$-S(O)$_2$NR$^a$R$^b$, -(L)$_m$-NR$^a$S(O)$_2$R$^b$; and the following groups optionally substituted with one or more Q1 groups: -(L)$_m$-C$_{1-6}$ alkyl, -(L)$_m$-C$_{1-6}$ alkoxy, -(L)$_m$-C$_{3-10}$ cycloalkyl, -(L)$_m$-C$_{3-10}$ heterocyclyl, -(L)$_m$-C$_{6-10}$ aryl and -(L)$_m$-C$_{5-10}$ heteroaryl;

L is selected from C$_{1-6}$ alkylene and halo C$_{1-6}$ alkylene;

R$^2$ is selected from the following groups optionally substituted by one or more Q2 groups: 3-8 membered heterocyclic group, 3-8 membered cycloalkyl group, 5-10 membered heteroaryl, 6-10 membered aryl, 5-10 membered spirocyclic group, 5-10 membered spiro heterocyclic group, 5-10 membered bridged group, 5-10 membered bridged heterocyclic group, N(C$_{1-6}$ alkyl)$_2$, N(C$_{1-6}$ alkyl) (C$_{3-8}$ cycloalkyl), NH(C$_{1-6}$ alkyl) and NH(C$_{3-8}$ cycloalkyl);

each R$^3$ is independently selected from hydrogen, halogen, nitro group, cyano group, amino group, hydroxyl, carboxy; and the following groups optionally substituted with one or more Q3 groups: C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-10 membered cycloalkyl group, 3-10 membered heterocyclic group, 6-10 membered aryl and 5-10 membered heteroaryl;

each R$^4$ is independently selected from hydrogen, cyano group, and the following groups optionally substituted with one or more Q4 groups: C$_{1-6}$ alkyl, —C(O)R$^a$, —C(O)OR$^a$, —C(O)NR$^a$R$^b$, —S(O)R$^a$, —S(O)OR$^a$, —S(O)NR$^a$R$^b$, —S(O)$_2$R$^a$, —S(O)$_2$OR$^a$, and —S(O)$_2$NR$^a$R$^b$;

each of R$^a$ and R$^b$ is independently selected from hydrogen, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl and halo C$_{1-6}$ alkoxy;

each of Q1, Q2, Q3 and Q4 groups is independently selected from hydroxyl, amino group, halogen, nitro group, cyano group, carboxy, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, and halo C$_{1-6}$ alkoxy; and m and n are each independently an integer from 0 to 6.

In certain embodiments, provided is said compound represented by the general formula (I), the pharmaceutically acceptable salt, the ester or the stereoisomer thereof:
wherein,
X, Y, and Z are each independently selected from —CR$^4$— and —N—;
ring A is selected from 3-10 membered cycloalkyl, 3-10 membered heterocyclic group, 6-10 membered aryl and 5-10 membered heteroaryl;

R$^1$ is selected from hydrogen, halogen, nitro group, cyano group, -(L)$_m$-C(O)OR$^a$, -(L)$_m$-CONR$^a$R$^b$, -(L)$_m$-CONHSO$_2$R$^a$, -(L)$_m$-SO$_2$R$^a$, -(L)$_m$-SO$_2$NHCOR$^a$, -(L)$_m$-OR$^a$, -(L)$_m$-NR$^a$R$^b$, -(L)$_m$-C(O)R$^a$, -(L)$_m$-OC(O)R$^a$, -(L)$_m$-NR$^a$C(O)R$^b$, -(L)$_m$-NR$^a$C(O)OR$^b$, -(L)$_m$-OS(O)$_2$R$^a$, -(L)$_m$-S(O)$_2$NR$^a$R$^b$, -(L)$_m$-NR$^a$S(O)$_2$R$^b$, and the following groups optionally substituted with one or more Q1 groups: -(L)$_m$-C$_{1-4}$ alkyl and -(L)$_m$-C$_{1-4}$ alkoxy;

L is selected from C$_{1-4}$ alkylene and halo C$_{1-4}$ alkylene;

R$^2$ is selected from the following groups optionally substituted by one or more Q2 groups: 3-8 membered heterocyclic group, 3-8 membered cycloalkyl group, 5-10 membered heteroaryl, 6-10 membered aryl, 5-10 membered spirocyclic group, 5-10 membered spiro heterocyclic group, N(C$_{1-4}$ alkyl)$_2$, N(C$_{1-4}$ alkyl) (C$_{3-6}$ cycloalkyl), NH(C$_{1-4}$ alkyl) and NH(C$_{3-6}$ cycloalkyl);

each R$^3$ is independently selected from hydrogen, halogen, nitro group, cyano group, amino group, hydroxyl, carboxy, and the following groups optionally substituted with one or more Q3 groups: C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy;

each R$^4$ is independently selected from hydrogen, cyano group, and the following groups optionally substituted with one or more Q4 groups: C$_{1-4}$ alkyl, —C(O)R$^a$, —C(O)OR$^a$, —C(O)NR$^a$R$^b$, —S(O)$_2$R$^a$, —S(O)$_2$OR$^a$, and —S(O)$_2$NR$^a$R$^b$;

each of R$^a$ and R$^b$ is independently selected from hydrogen, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl and halo C$_{1-4}$ alkoxy;

each of Q1, Q2, Q3, and Q4 groups is independently selected from hydroxyl, amino group, halogen, nitro group, cyano group, carboxy, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy; and m and n are each independently an integer from 0 to 6.

In certain embodiments, provided is said compound represented by the general formula (I), the pharmaceutically acceptable salt, the ester or the stereoisomer thereof:
X, Y, and Z are each independently selected from —CR$^4$— and —N—;
ring A is selected from 3-10 membered cycloalkyl and 3-10 membered heterocyclic group;

R$^1$ is selected from -(L)$_m$-C(O)OR$^a$, -(L)$_m$-CONR$^a$R$^b$, -(L)$_m$-CONHSO$_2$R$^a$, -(L)$_m$-SO$_2$R$^a$, -(L)$_m$-SO$_2$NHCOR$^a$, -(L)$_m$-OR$^a$, -(L)$_m$-NR$^a$R$^b$, -(L)$_m$-C(O)R$^a$, -(L)$_m$-OC(O)R$^a$, -(L)$_m$-NR$^a$C(O)R$^b$, -(L)$_m$-NR$^a$C(O)OR$^b$, -(L)$_m$-OS(O)$_2$R$^a$, -(L)$_m$-S(O)$_2$NR$^a$R$^b$, -(L)$_m$-NR$^a$S(O)$_2$R$^b$, and the following groups optionally substituted with 1-4 Q1 groups: -(L)$_m$-C$_{1-4}$ alkyl and -(L)$_m$-C$_{1-4}$ alkoxy;

L is selected from C$_{1-3}$ alkylene and halo C$_{1-3}$ alkylene;

R$^2$ is selected from the following groups optionally substituted by 1-4 Q2 groups: 3-6 membered heterocyclic group, 3-6 membered cycloalkyl, 5-8 membered heteroaryl, 6-8 membered aryl, 5-8 membered spirocyclic group, 5-8 membered spiro heterocyclic group, and N(C$_{1-4}$ alkyl)(C$_{3-6}$ cycloalkyl);

each R$^3$ is independently selected from hydrogen, halogen, nitro group, cyano group, amino group, hydroxyl, carboxy, and the following groups optionally substituted with 1-4 Q3 groups: C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy;

each R$^4$ is independently selected from hydrogen, or the following groups optionally substituted with one or more Q4 groups: C$_{1-4}$ alkyl, —C(O)R$^a$, —C(O)OR$^a$, —C(O)NR$^a$R$^b$, —S(O)$_2$R$^a$, and —S(O)$_2$NR$^a$R$^b$;

each of R$^a$ and R$^b$ is independently selected from hydrogen, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl and halo C$_{1-4}$ alkoxy;

each of Q1, Q2, Q3, and Q4 groups is independently selected from hydroxyl, amino group, halogen, nitro group, cyano group, carboxy, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy; and m and n are each independently an integer from 0 to 4.

In certain embodiment, provided is said compound represented by the general formula (I), the pharmaceutically acceptable salt, the ester or the stereoisomer thereof:
wherein,
X, Y, and Z are each independently selected from —CR$^4$— and —N—;
ring A is selected from 4-8 membered cycloalkyl and 4-8 membered heterocyclic group;
R$^1$ is selected from -(L)$_m$-C(O)OR$^a$, -(L)$_m$-CONR$^a$R$^b$, -(L)$_m$-SO$_2$R$^a$, -(L)$_m$-OR$^a$, -(L)$_m$-NR$^a$R$^b$, -(L)$_m$-C(O)R$^a$, -(L)$_m$-OC(O)R$^a$, -(L)$_m$-NR$^a$C(O)R$^b$, -(L)$_m$-S(O)$_2$NR$^a$R$^b$, -(L)$_m$-NR$^a$S(O)$_2$R$^b$, and the following groups optionally substituted with 1-3 Q1 groups: -(L)$_m$-C$_{1-4}$ alkyl and -(L)$_m$-C$_{1-4}$ alkoxy;
L is C$_{1-3}$ alkylene;
R$^2$ is selected from the following groups optionally substituted by 1-4 Q2 groups: 3-6 membered heterocyclic group, 5-8 membered spiro heterocyclic group, 5-6 membered heteroaryl, and N(C$_{1-4}$ alkyl)(C$_{3-6}$ cycloalkyl);
each R$^3$ is independently selected from hydrogen, halogen, nitro group, cyano group, amino group, hydroxyl and carboxy;
each R$^4$ is independently selected from hydrogen and C$_{1-4}$ alkyl;
each of R$^a$ and R$^b$ is independently selected from hydrogen and C$_{1-4}$ alkyl;
each of Q1 and Q2 groups is independently selected from hydroxyl, amino group, halogen, nitro group, cyano group, carboxy, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy; and m and n are each independently an integer from 0 to 3.

In certain embodiments, provided is said compound represented by the general formula (I), the pharmaceutically acceptable salt, the ester or the stereoisomer thereof:
wherein,
X, Y and Z are each independently —N—;
ring A is 4-7 membered cycloalkyl;
R$^1$ is selected from -(L)$_m$-C(O)OR$^a$, -(L)$_m$-CONR$^a$R$^b$, -(L)$_m$-SO$_2$R$^a$, -(L)$_m$-OR$^a$, -(L)$_m$-NR$^a$R$^b$, -(L)$_m$-C(O)R$^a$, and the following groups optionally substituted with 1-3 Q1 groups: -(L)$_m$-C$_{1-4}$ alkyl and -(L)$_m$-C$_{1-4}$ alkoxy;
L is methylene;
R$^2$ is selected from the following groups optionally substituted by 1-3 Q2 groups: oxetanyl, azetidinyl, tetrahydrofuranyl, tetrahydrothienyl, pyrrolidinyl, imidazolidinyl, oxazolidinyl, thiazolidinyl, piperidinyl, piperazinyl, morpholinyl, furyl, pyranyl, pyrrolyl, thienyl, thiazolyl, isothiazolyl, thiadiazolyl, imidazolyl, pyrazolyl, oxazolyl, isoxazolyl, oxadiazolyl, triazolyl, tetrazolyl, pyridyl, pyrimidinyl, pyrazinyl, pyridazinyl, triazinyl, tetrazinyl,

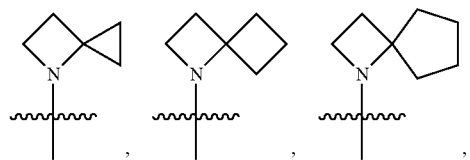

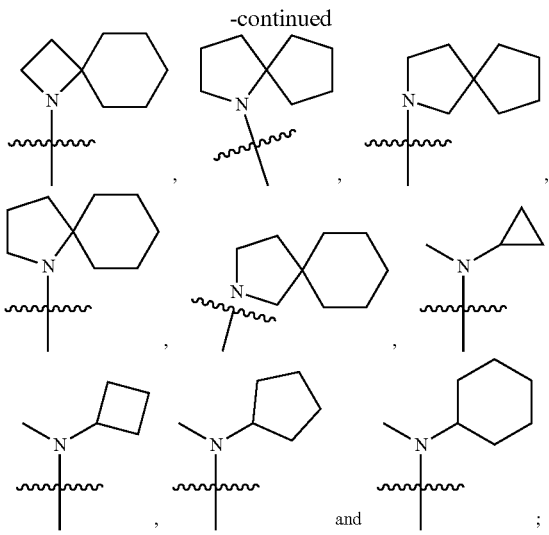

each R$^3$ is independently selected from hydrogen, halogen, nitro group, cyano group, amino group, hydroxyl and carboxy;
each of R$^a$ and R$^b$ is independently selected from hydrogen, methyl, ethyl, propyl, isopropyl, butyl, isobutyl, sec-butyl, and tert-butyl;
each of Q1 and Q2 groups is independently selected from hydroxyl, amino group, fluorine, chlorine, bromine, iodine, nitro group, cyano group, carboxy, methyl, ethyl, propyl, isopropyl, butyl, isobutyl, sec-butyl, tert-butyl, methoxy, ethoxy, propoxy, methylamino, dimethylamino, trifluoromethyl and trifluoromethoxy; and m and n are each independently 0, 1, 2 or 3.

In certain embodiments, provided is said compound represented by the general formula (I), the pharmaceutically acceptable salt, the ester or the stereoisomer thereof:
wherein,
X, Y and Z are each independently —N—;
ring A is 4-7 membered cycloalkyl;
R$^1$ is selected from -(L)$_m$-C(O)OR$^a$, -(L)$_m$-CONR$^a$R$^b$, -(L)$_m$-SO$_2$R$^a$, -(L)$_m$-OR$^a$, -(L)$_m$-NR$^a$R$^b$, -(L)$_m$-C(O)R$^a$, -(L)$_m$-OC(O)R$^a$; and the following groups optionally substituted with 1-3 Q1 groups: -(L)$_m$-C$_{1-4}$ alkyl and -(L)$_m$-C$_{1-4}$ alkoxy;
L is C$_{1-3}$ alkylene;
R$^2$ is selected from the following groups optionally substituted by 1-3 Q2 groups: 4-6 membered heterocyclic group, 5-6 membered heteroaryl, and N(C$_{1-4}$ alkyl)(C$_{3-6}$ cycloalkyl);
each R$^3$ is independently selected from hydrogen, halogen, nitro group, cyano group, amino group, hydroxyl and carboxy;
each of R$^a$ and R$^b$ is independently selected from hydrogen and C$_{1-4}$ alkyl;
each of Q1 and Q2 groups is independently selected from hydroxyl, amino group, halogen, nitro group, cyano group, carboxy, C$_{1-4}$ alkyl, C$_{1-4}$ alkoxy, C$_{1-4}$ alkylamino, di(C$_{1-4}$ alkyl)amino, halo C$_{1-4}$ alkyl, hydroxy C$_{1-4}$ alkyl, amino C$_{1-4}$ alkyl, and halo C$_{1-4}$ alkoxy; and m and n are each independently an integer from 0 to 3.

In certain embodiments, provided is said compound represented by the general formula (I), the pharmaceutically acceptable salt, the ester or the stereoisomer thereof:

wherein,

X, Y and Z are each independently —N—;

Ring A is 4-7 membered cycloalkyl;

$R^1$ is selected from -$(L)_m$-C(O)O$R^a$, -$(L)_m$-CON$R^aR^b$, -$(L)_m$-SO$_2R^a$, -$(L)_m$-O$R^a$, -$(L)_m$-N$R^aR^b$, -$(L)_m$-C(O)$R^a$; and the following groups optionally substituted with 1-3 Q1 groups: -$(L)_m$-$C_{1-4}$ alkyl and -$(L)_m$-$C_{1-4}$ alkoxy;

L is methylene;

$R^2$ is selected from the following groups optionally substituted by 1-3 Q2 groups: oxetanyl, azetidinyl, tetrahydrofuranyl, tetrahydrothienyl, pyrrolidinyl, imidazolidinyl, oxazolidinyl, thiazolidinyl, piperidinyl, piperazinyl, morpholinyl, furyl, pyranyl, pyrrolyl, thienyl, thiazolyl, isothiazolyl, thiadiazolyl, imidazolyl, pyrazolyl, oxazolyl, isoxazolyl, oxadiazolyl, triazolyl, tetrazolyl, pyridyl, pyrimidinyl, pyrazinyl, pyridazinyl, triazinyl, tetrazinyl,

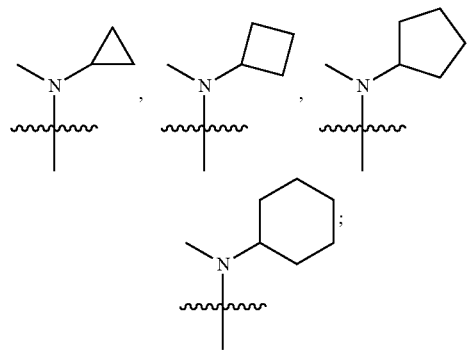

and each $R^3$ is independently selected from hydrogen, halogen, nitro group, cyano group, amino group, hydroxyl and carboxy;

each of $R^a$ and $R^b$ is independently selected from hydrogen, methyl, ethyl, propyl, isopropyl, butyl, isobutyl, sec-butyl, and tert-butyl;

each of Q1 and Q2 groups is independently selected from hydroxyl, amino group, fluorine, chlorine, bromine, iodine, nitro group, cyano group, carboxy, methyl, ethyl, propyl, isopropyl, butyl, isobutyl, sec-butyl, tert-butyl, methoxy, ethoxy, propoxy, methylamino, dimethylamino, trifluoromethyl and trifluoromethoxy; and m and n are each independently 1, 2 or 3.

In certain embodiments, provided is said compound represented by the general formula (I), the pharmaceutically acceptable salt, the ester or the stereoisomer thereof:

wherein, ring A is a 5-6 membered cycloalkyl group; preferably a 5-6 membered partially saturated cycloalkyl group and a 5-6 membered saturated cycloalkyl group.

The options for any substituent group in any embodiment of the present invention may be combined with each other, and the technical solution(s) resulted from the combination is/are still comprised in the protection scope of the present invention.

In some embodiments of the present invention, the structures of the aforementioned compounds of the general formula (I), the pharmaceutically acceptable salt, the ester or the stereoisomer thereof are shown in Table 1:

TABLE 1

| Number | Structure |
|---|---|
| Compound 1 | 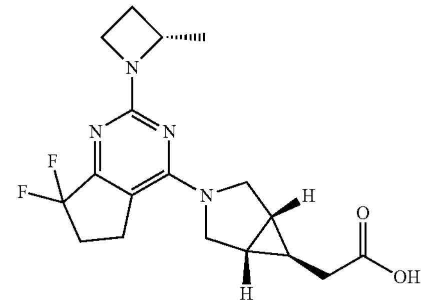 |
| Compound 1-1 | 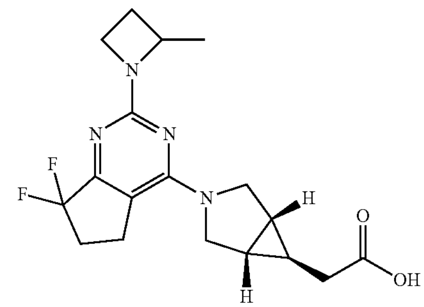 [SMILES: CC1CCN1c1nc(N2C[C@@H]3[C@@H](CC(=O)O)[C@@H]3C2)c2c(n1)C(F)(F)CC2] |
| Compound 1-2 | 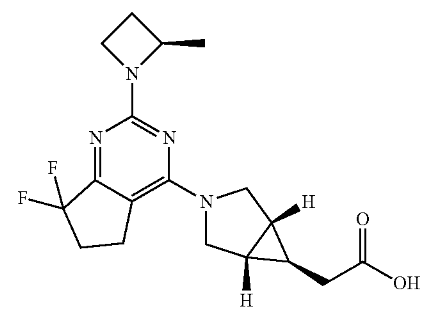 [SMILES: C[C@@H]1CCN1c1nc(N2C[C@@H]3[C@@H](CC(=O)O)[C@@H]3C2)c2c(n1)C(F)(F)CC2] |
| Compound 2 | 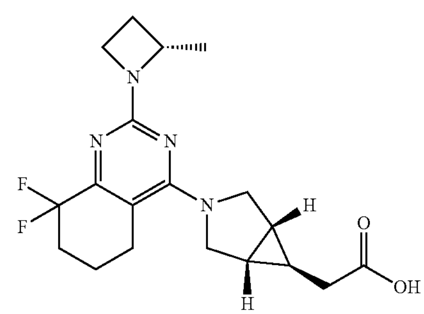 [SMILES: C[C@H]1CCN1c1nc(N2C[C@@H]3[C@@H](CC(=O)O)[C@@H]3C2)c2c(n1)C(F)(F)CCC2] |
| Compound 2-1 | 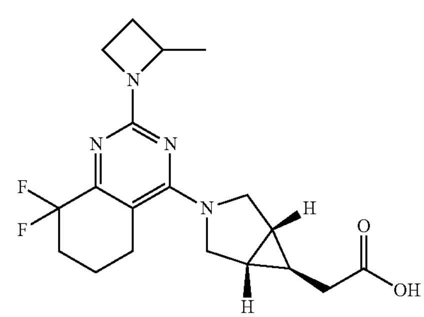 [SMILES: CC1CCN1c1nc(N2C[C@@H]3[C@@H](CC(=O)O)[C@@H]3C2)c2c(n1)C(F)(F)CCC2] |

TABLE 1-continued
| Number | Structure |
|---|---|
| Compound 2-2 | 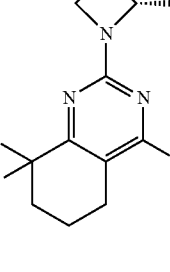 |
| Compound 3 | 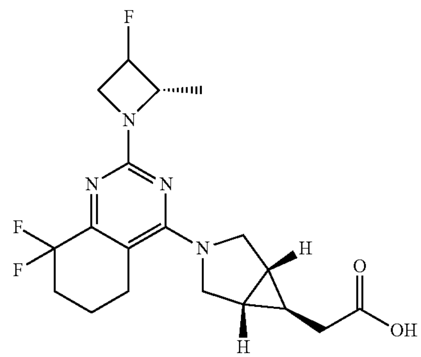 |
| Compound 3-1 | 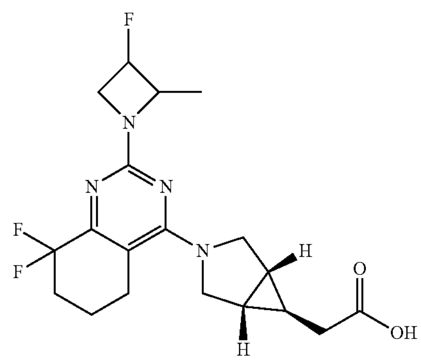 [SMILES: CC1C(F)CN1c1nc(N2C[C@@H]3[C@@H](CC(=O)O)[C@@H]3C2)c2c(n1)C(F)(F)CCC2] |
| Compound 3-2 | 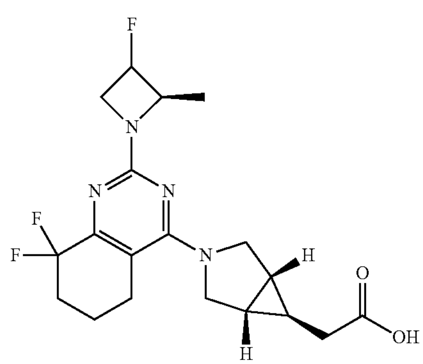 [SMILES: C[C@@H]1C(F)CN1c1nc(N2C[C@@H]3[C@@H](CC(=O)O)[C@@H]3C2)c2c(n1)C(F)(F)CCC2] |
TABLE 1-continued
| Number | Structure |
|---|---|
| Compound 4 | 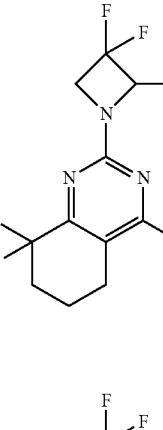 |
| Compound 4-1 | 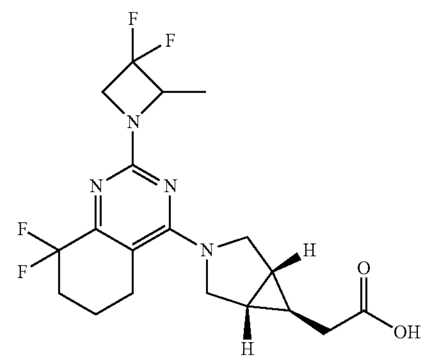 [SMILES: CC1N(c2nc(N3C[C@@H]4[C@@H](CC(=O)O)[C@@H]4C3)c3c(n2)C(F)(F)CCC3)CC1(F)F] |
| Compound 4-2/ Compound 4-3 | 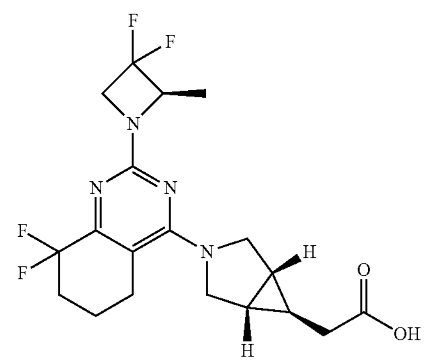 [SMILES: C[C@H]1N(c2nc(N3C[C@@H]4[C@@H](CC(=O)O)[C@@H]4C3)c3c(n2)C(F)(F)CCC3)CC1(F)F] |
| Compound 5 | 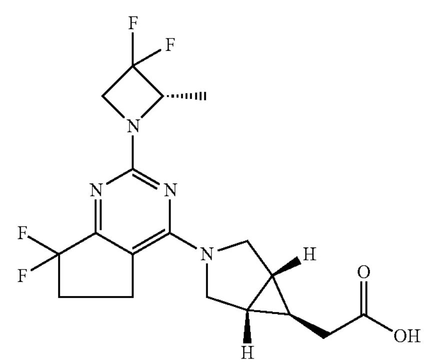 [SMILES: C[C@@H]1N(c2nc(N3C[C@@H]4[C@@H](CC(=O)O)[C@@H]4C3)c3c(n2)C(F)(F)CC3)CC1(F)F] |

TABLE 1-continued

| Number | Structure |
|---|---|
| Compound 5-1 | |
| Compound 5-2 | |
| Compound 6 | |
| Compound 6-1 | |
| Compound 6-2 | 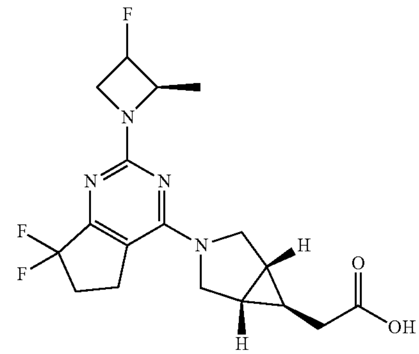 [SMILES: C[C@@H]1C(F)CN1c1nc(N2C[C@@H]3[C@@H](CC(=O)O)[C@@H]3C2)c2c(n1)C(F)(F)CC2] |
| Compound 7 | 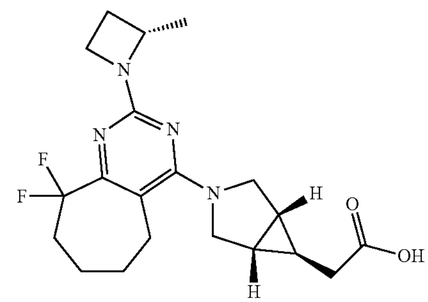 [SMILES: C[C@H]1CCN1c1nc(N2C[C@@H]3[C@@H](CC(=O)O)[C@@H]3C2)c2c(n1)C(F)(F)CCCC2] |
| Compound 7-1 | 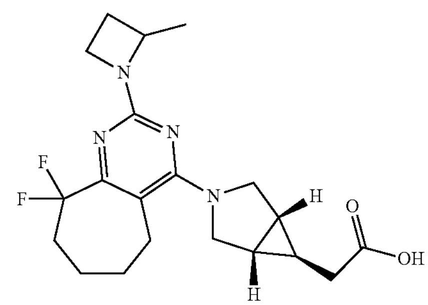 |
| Compound 7-2 | 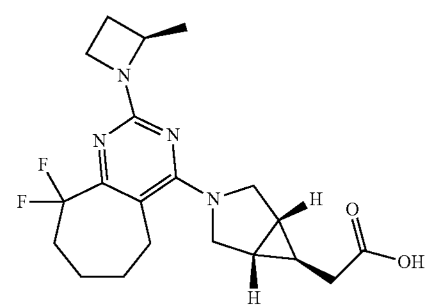 [SMILES: C[C@@H]1CCN1c1nc(N2C[C@@H]3[C@@H](CC(=O)O)[C@@H]3C2)c2c(n1)C(F)(F)CCCC2] |
| Compound 8 | 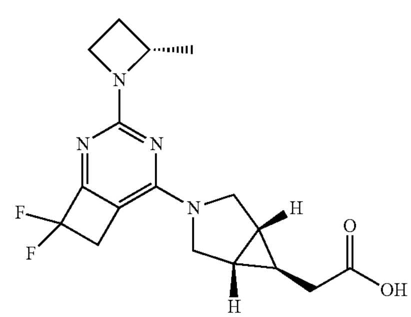 |

TABLE 1-continued

| Number | Structure |
|---|---|
| Compound 8-1 | 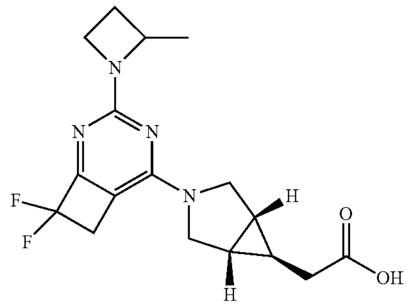 [SMILES: CC1CCN1c1nc(N2C[C@@H]3[C@@H](CC(=O)O)[C@@H]3C2)c2c(n1)C(F)(F)C2] |
| Compound 8-2 | 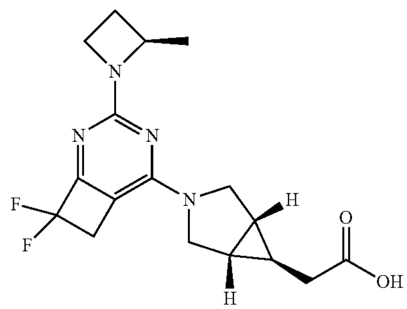 [SMILES: C[C@@H]1CCN1c1nc(N2C[C@@H]3[C@@H](CC(=O)O)[C@@H]3C2)c2c(n1)C(F)(F)C2] |
| Compound 9 | 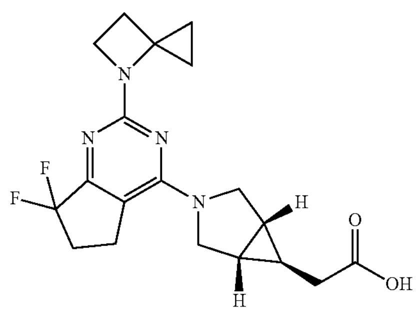 [SMILES: O=C(O)C[C@@H]1[C@H]2CN(c3nc(N4CCC45CC5)nc4c3CCC4(F)F)C[C@@H]12] |
| Compound 10 | 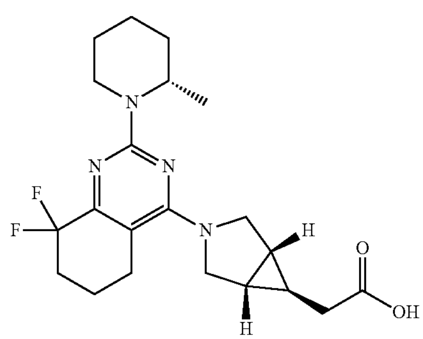 [SMILES: C[C@H]1CCCCN1c1nc(N2C[C@@H]3[C@@H](CC(=O)O)[C@@H]3C2)c2c(n1)C(F)(F)CCC2] |
| Compound 10-1 | 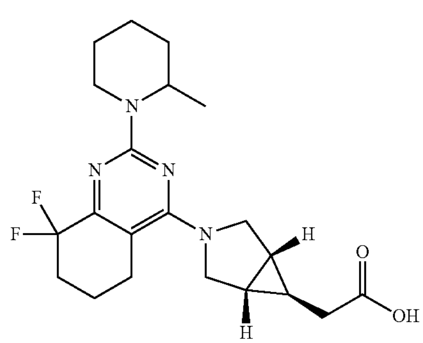 [SMILES: CC1CCCCN1c1nc(N2C[C@@H]3[C@@H](CC(=O)O)[C@@H]3C2)c2c(n1)C(F)(F)CCC2] |
| Compound 11 | |
| Compound 12 | |
| Compound 12-1 | |
| Compound 13 | |

TABLE 1-continued

| Number | Structure |
|---|---|
| Compound 14 | 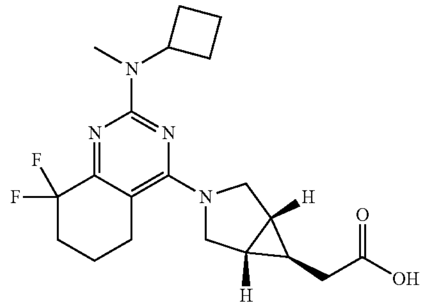 [SMILES: CN(c1nc(N2C[C@@H]3[C@@H](CC(=O)O)[C@@H]3C2)c2c(n1)C(F)(F)CCC2)C1CCC1] |
| Compound 15 | 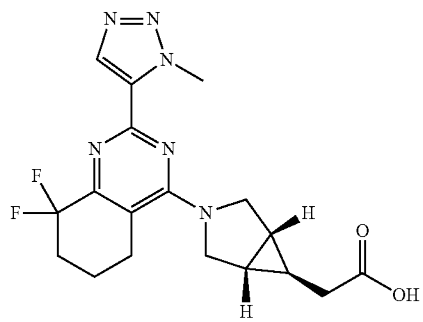 [SMILES: Cn1nncc1-c1nc(N2C[C@@H]3[C@@H](CC(=O)O)[C@@H]3C2)c2c(n1)C(F)(F)CCC2] |
| Compound 16 | 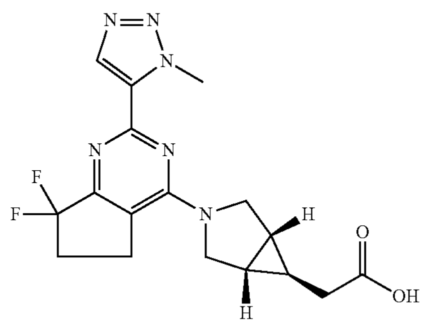 [SMILES: Cn1nncc1-c1nc(N2C[C@@H]3[C@@H](CC(=O)O)[C@@H]3C2)c2c(n1)C(F)(F)CC2] |
| Compound 17 | 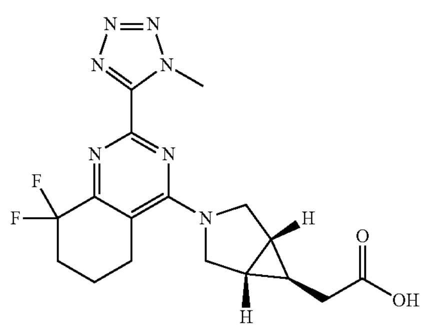 [SMILES: Cn1nnnc1-c1nc(N2C[C@@H]3[C@@H](CC(=O)O)[C@@H]3C2)c2c(n1)C(F)(F)CCC2] |
| Compound 18 | 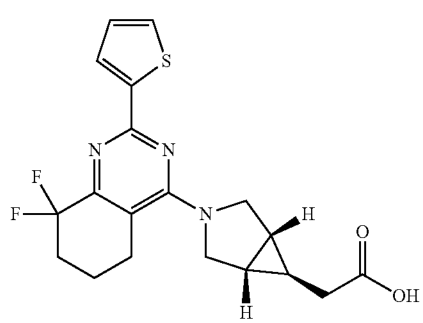 [SMILES: O=C(O)C[C@@H]1[C@H]2CN(c3nc(-c4cccs4)nc4c3CCCC4(F)F)C[C@@H]12] |
| Compound 19 | |
| Compound 20 | |

The term "pharmaceutically acceptable salt(s)" as used in the present invention refers to pharmaceutically acceptable acid and base addition salt(s).

The term "ester(s)" as used in the present invention refers to pharmaceutically acceptable ester(s), in particular, ester(s) that hydrolyze(s) in vivo, and comprises the ester(s) that is/are easily decomposed in vivo to leave the parent compound (the compound represented by general formula (I)) or the salt thereof. In some embodiments of the present invention, the pharmaceutically acceptable ester(s) comprise(s) those derived from pharmaceutically acceptable aliphatic carboxylic acid(s) and phosphoric acid(s).

The term "stereoisomer(s)" of the compound represented by the general formula (I) of the present invention refers to that the compound represented by the formula (I) will be present as enantiomers if having asymmetric carbon atoms; the compound will be present as cis-trans isomers if having carbon-carbon double bond(s) or ring structure(s); and the compound will be present as tautomers if having ketone(s) or oxime(s). In some embodiments of the present invention, the stereoisomer(s) comprise(s) but are not limited to: enantiomer(s), diastereomer(s), racemic isomer(s), cis-trans isomer(s), tautomer(s), geometric isomer(s), epimer(s), and mixture(s) thereof.

The embodiments of the present invention also provide, but are not limited to, two preparation methods for the above compounds. The reaction scheme of the preparation method I is as follows:

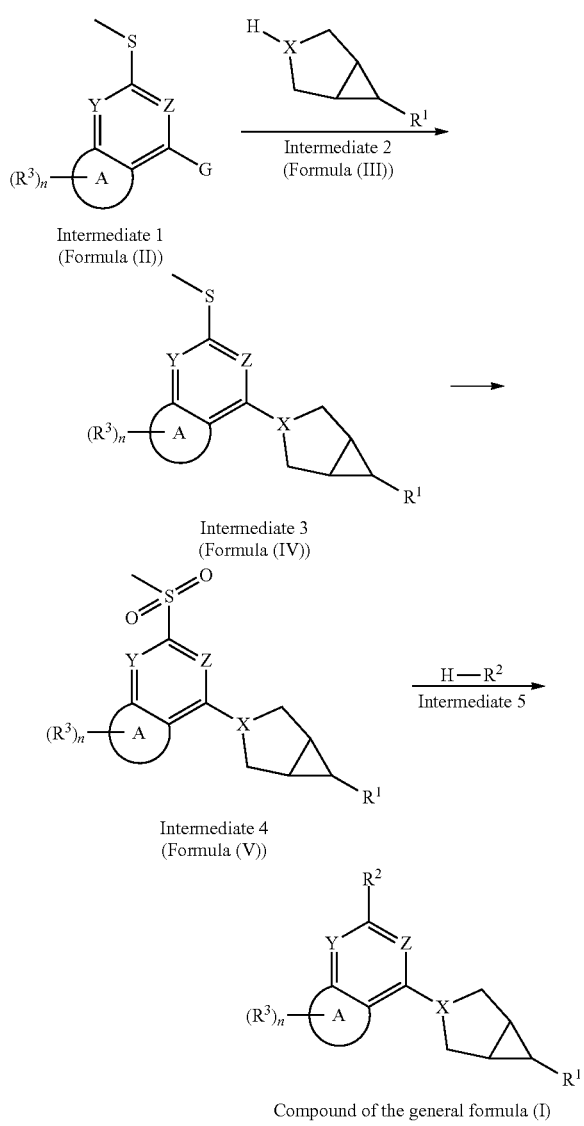

Step 1: Preparation of Intermediate 1
Intermediate 1 is prepared in laboratory.
Step 2: Preparation of Intermediate 2
Intermediate 2 is prepared by referring to the preparation method of the document (U.S. Ser. No. 15/381,295).
Step 3: Preparation of Intermediate 3
Intermediate 1 is dissolved in a suitable solvent (such as NMP), added with Intermediate 2 and an alkaline substance (such as potassium carbonate). The reaction is carried out at 70-100° C. for 10-40 hours, added with water, and extracted with a suitable organic solvent (such as ethyl acetate). Then, the organic phase is concentrated, and subjected to an appropriate method (such as silica gel column chromatography) to obtain Intermediate 3.
Step 4: Preparation of Intermediate 4
Intermediate 3 is dissolved in a suitable solvent (such as dichloromethane), added with metachloroperbenzoic acid. Then the reaction is conducted at 10-30° C. for 0.5-5 hours, quenched by adding a suitable substance (such as sodium thiosulfate), washed with a suitable reagent (such as saturated sodium carbonate, and saturated brine), dried, concentrated, and subjected to an appropriate method (such as silica gel column chromatography) to obtain Intermediate 4.

Step 5: Preparation of the Compound of General Formula (I) of the Present Invention
Intermediate 4 is dissolved in a suitable solvent (such as NMP), and added with DIEA, H—$R^2$ or $R^2$ salt. The reaction is conducted at 100-200° C. for 1-5 hours, added with water, extracted with a suitable organic solvent (such as ethyl acetate), and spin-dried. The spin-dried product is dissolved in a suitable solvent (such as THF/$H_2O$), added with an alkaline reagent (such as NaOH, KOH, etc.). The reaction is carried out at 10-50° C. for 0.2-5 hours, adjusted to pH 4.5-5.5, concentrated, and subjected to an appropriate method (such as silica gel column chromatography) to obtain the compound of the general formula (I) of the present invention.

The above preparation process can also be briefly summarized as the following steps of:
reacting the compound represented by formula (II) with the compound represented by formula (III) to obtain the compound represented by formula (IV);
subjecting the thio group in the compound represented by formula (IV) to functional group conversion reaction to obtain the compound represented by formula (V); and
reacting the compound represented by formula (V) to obtain the compound represented by the general formula (I).

The reaction scheme of preparation method II is as follows:

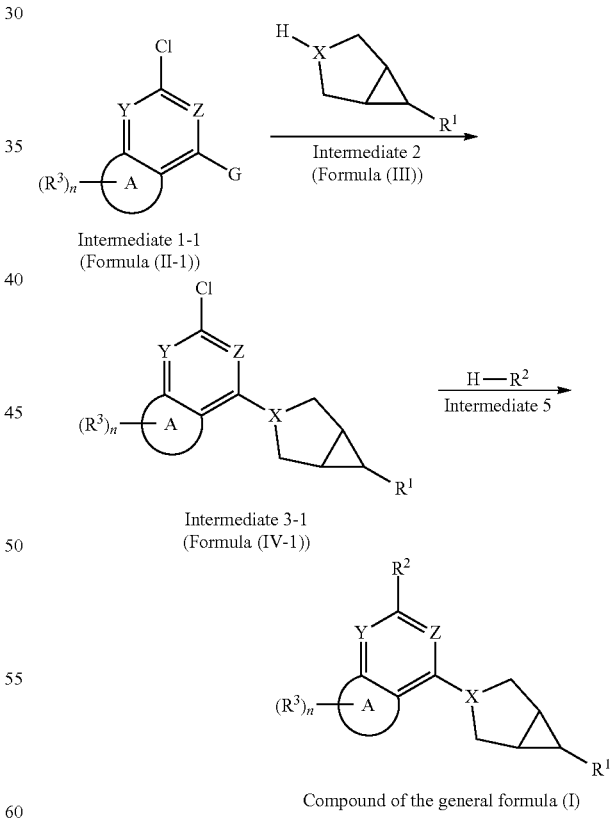

Step 1: Preparation of Intermediate 1-1
Intermediate 1-1 is prepared in laboratory.
Step 2: Preparation of Intermediate 2
Intermediate 2 is prepared by referring to the preparation method of the document (U.S. Ser. No. 15/381,295).

Step 3: Preparation of Intermediate 3-1

Intermediate 1-1 is dissolved in a suitable solvent (such as acetonitrile), and added with Intermediate 2 and an alkaline substance (such as DIPEA). Then, the reaction is conducted at 70-100° C. for 10-30 hours, spin-dried, and subjected to an appropriate method (such as silica gel column chromatography) to obtain Intermediate 3-1.

Step 4: Preparation of the Compound of General Formula (I) of the Present Invention Intermediate 3-1 is dissolved in a suitable solvent (such as dioxane), and added with H—R$^2$, Pd(pph$_3$)Cl$_2$, and x-phos. The reaction is conducted at 80-200° C. for 10-20 hours under the protection of nitrogen, cooled to 10-30° C., spin-dried, and subjected to an appropriate method (such as silica gel column chromatography) to obtain a product. The product is then dissolved in a suitable solvent (such as THF and water), and added with an alkaline substance (such as NaOH, KOH, and etc.). The reaction is carried out at 10-30° C. for 0.5-5 hours, adjusted to an acidic pH, and filtrated to obtain the compound of general formula (I) of the present invention.

The above preparation process can also be briefly summarized as the following steps of:

reacting the compound represented by formula (II-1) with the compound represented by formula (III) to obtain the compound represented by formula (IV-1); and reacting the compound represented by the formula (IV-1) to obtain the compound represented by the general formula (I).

The term "functional group conversion reaction" as used herein can be achieved by using known chemical synthesis methods, comprising but not limited to substitution reaction, addition reaction, elimination reaction, dehydration reaction, hydrolysis reaction, oxidation reaction and esterification reaction, etc. These reactions are well-known for those skilled in the chemistry field, and will not be described in the present invention. In the embodiments, those reactions can be achieved through one-step or multi-step reaction(s).

In addition, some necessary starting materials, such as the materials for synthesizing intermediates, can be synthesized according to steps and methods similar to those described in the Organic Chemistry Handbook, and will not further described in the present invention.

The substituent G in the above reaction schemes is halogen; and R$^1$, R$^2$, R$^3$, X, Y, Z, n and ring A are as defined above.

The present invention also provides intermediates for synthesizing the compound represented by the general formula (I), the intermediates having the following structural formulae:

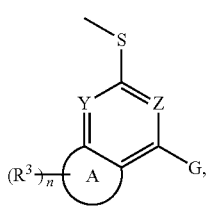

formula (II)

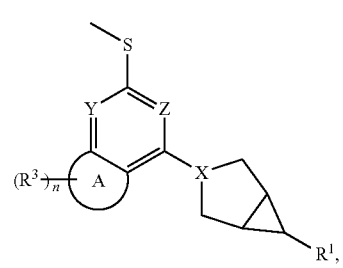

formula (IV)

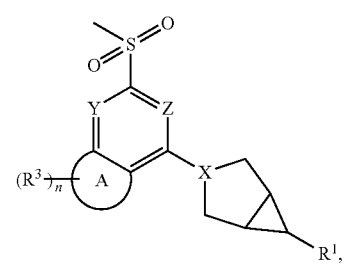

formula (V)

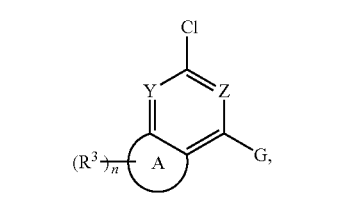

formula (II-1)

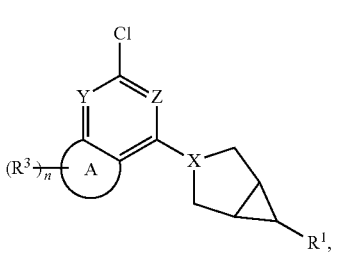

formula (IV-1)

wherein, the substituent G is halogen; and R$^1$, R$^3$, X, Y, Z, n and ring A are as defined above.

The present invention also provides a pharmaceutical composition comprising the above compound represented by the general formula (I), the pharmaceutically acceptable salt, the ester or the stereoisomer thereof, and one or more second therapeutic agents; and optionally one or more pharmaceutically acceptable carrier(s) and/or diluent(s).

The present invention also provides a pharmaceutical formulation comprising the above compound represented by the general formula (I), the pharmaceutically acceptable salt, the ester or the stereoisomer thereof, and one or more pharmaceutically acceptable carrier(s) and/or diluent(s); wherein the pharmaceutical formulation is in any dosage form that is clinically or pharmaceutically acceptable.

In some embodiments of the present invention, the above-mentioned pharmaceutical formulation may be administered to patients or subjects in need of such treatment orally, parenterally, rectally, or pulmonarily. For oral administration, the pharmaceutical composition may be made into oral formulations. For example, it may be made into conventional oral solid formulations, such as tablets, capsules, pills, granules, etc. It may also be made into oral liquid formulations, such as oral solutions, oral suspensions, syrups, etc. When the pharmaceutical composition is made into oral formulations, suitable filler(s), binder(s), disintegrant(s), lubricant(s), etc. may be added. For parenteral administration, the above-mentioned pharmaceutical formulation may also be made into injections, including solutions for injection, sterile powders for injection, and concentrated solutions for injection. When the pharmaceutical composition is made into injections, it may be made by the conventional methods in the pharmaceutical field. When the pharmaceutical composition is formulated into the injections, the additives may not be added, or appropriate additives may be added according to the nature of the pharmaceuticals. For rectal administration, the pharmaceutical composition may be made into suppositories and the like. For pulmonary administration, the pharmaceutical composition may be made into inhalants or sprays.

The pharmaceutically acceptable carrier(s) and/or diluent(s) usable in the pharmaceutical composition or pharmaceutical formulation of the present invention may be any conventional carrier and/or diluent in the pharmaceutical formulation field, and the choice of the specific carrier(s) and/or diluent(s) depends on the route of administration for or the type and the condition of disease of the particular patient to be treated. The preparation method of a suitable pharmaceutical composition for a specific route of administration is completely within the knowledge of those skilled in the pharmaceutical field. For example, pharmaceutical carrier(s) and/or diluent(s) may include solvent(s), diluent(s), dispersant(s), suspending agent(s), surfactant(s), isotonic agent(s), thickener(s), emulsifier(s), binder(s), lubricant(s), stabilizer(s), hydrating agent(s), emulsification accelerator(s), buffer(s), absorbent(s), colorant(s), ion exchanger(s), release agent(s), coating agent(s), flavoring agent(s), antioxidant(s), etc. conventional in the pharmaceutical field. If necessary, flavor(s), preservative(s), sweetener(s), etc. may also be added to the pharmaceutical composition.

The present invention also provides use of the compound represented by the aforementioned general formula (I), the pharmaceutically acceptable salt, the ester or the stereoisomer thereof, the aforementioned pharmaceutical formulation or the aforementioned pharmaceutical composition in the manufacture of a medicament for the treatment and/or prevention of KHK-mediated diseases and related conditions, which may be selected from endocrine disorders, urinary diseases, metabolic diseases, non-alcoholic steatohepatitis, liver cirrhosis, fatty liver, hepatitis, liver failure, hereditary fructose intolerance, non-alcoholic fatty liver disease, hepatobiliary diseases, fibrotic diseases, cardiovascular and cerebrovascular diseases, immune inflammatory diseases, central nervous system diseases, gastrointestinal diseases, and excessive proliferative diseases such as cancer.

The present invention also provides use of the compound represented by the aforementioned general formula (I), the pharmaceutically acceptable salt, the ester or the stereoisomer thereof, the aforementioned pharmaceutical formulation or the aforementioned pharmaceutical composition in the treatment and/or prevention of KHK-mediated diseases and related conditions, which may be selected from endocrine disorders, urinary diseases, metabolic diseases, non-alcoholic steatohepatitis, liver cirrhosis, fatty liver, hepatitis, liver failure, hereditary fructose intolerance, non-alcoholic fatty liver disease, hepatobiliary diseases, fibrotic diseases, cardiovascular and cerebrovascular diseases, immune inflammatory diseases, central nervous system diseases, gastrointestinal diseases, excessive proliferative diseases such as cancer.

The present invention also provides a method for treating a disease, comprising administering to a patient in need thereof a therapeutically effective amount of the compound represented by the aforementioned general formula (I), the pharmaceutically acceptable salt, the ester or the stereoisomer thereof, the aforementioned pharmaceutical formulation or the aforementioned pharmaceutical composition; wherein the disease is a KHK-mediated disease and related conditions, which may be selected from endocrine disorders, urinary diseases, metabolic diseases, non-alcoholic steatohepatitis, liver cirrhosis, fatty liver, hepatitis, liver failure, hereditary fructose intolerance, non-alcoholic fatty liver disease, hepatobiliary diseases, fibrotic diseases, cardiovascular and cerebrovascular diseases, immune inflammatory diseases, central nervous system diseases, gastrointestinal diseases, excessive proliferative diseases such as cancer.

In the specification and claims of the present application, the compounds are named according to the chemical structural formulae. If the name and the chemical structural formula representing the same compound do not match with each other, the chemical structural formula shall prevail.

In the present application, unless otherwise specified, the scientific and technical terms used herein have the meanings commonly understood by those skilled in the art. However, in order to better understand the present invention, the definitions of some terms are provided below. When the definitions and explanations of the terms provided in the present application do not match the meaning commonly understood by those skilled in the art, the definitions and explanations of the terms provided in the present application shall prevail.

The term "halogen" as used in the present invention refers to fluorine, chlorine, bromine and iodine, and preferably fluorine and chlorine.

The term "halo" as used in the present invention refers to the substituent group in which any hydrogen may be substituted with one or more identical or different halogens. "Halogen" is as defined above.

The term "$C_{1-6}$ alkyl group" as used in the present invention refers to a straight or branched chain alkyl containing 1-6 carbon atoms, including, for example, "$C_{1-5}$ alkyl", "$C_{1-4}$ alkyl", "$C_{1-3}$ alkyl", "$C_{1-2}$ alkyl", "$C_{2-6}$ alkyl", "$C_{2-5}$ alkyl", "$C_{2-4}$ alkyl", "$C_{2-3}$ alkyl", "$C_{3-6}$ alkyl", "$C_{3-5}$ alkyl", "$C_{3-4}$ alkyl", "$C_{4-6}$ alkyl", "$C_{4-5}$ alkyl", and "$C_{5-6}$ alkyl", etc. Specific examples include but are not limited to: methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, and 1,2-dimethylpropyl, etc. The term "$C_{1-4}$ alkyl" as used in the present invention refers to a specific example of $C_{1-6}$ alkyl containing 1 to 4 carbon atoms.

The term "$C_{1-6}$ alkylene" as used in the present invention refers to the group formed by removing one hydrogen atom from the aforementioned $C_{1-6}$ alkyl, including, for example, "$C_{1-5}$ alkylene", "$C_{1-4}$ alkylene", "$C_{1-3}$ alkylene", "$C_{1-2}$ alkylene", "$C_{2-6}$ alkylene", "$C_{2-5}$ alkylene", "$C_{2-4}$ alkylene", "$C_{2-3}$ alkylene", "$C_{3-6}$ alkylene", "$C_{3-5}$ alkylene", "$C_{3-4}$ alkylene", "$C_{4-6}$ alkylene", "$C_{4-5}$ alkylene", and "$C_{5-6}$ alkylene", etc. Specific examples include but are not limited to: methylene, ethylene, propylene, butylene, pentylene, and hexylene, etc. The term "$C_{1-4}$ alkylene" as used in the present invention refers to a specific example of $C_{1-6}$ alkylene containing 1 to 4 carbon atoms.

As used herein, the terms "$C_{1-6}$ alkoxy", "$C_{1-6}$ alkylamino", and "di($C_{1-6}$ alkyl)amino" refer to the groups in a form of $C_{1-6}$ alkyl-O—, $C_{1-6}$ alkyl-NH—, and $(C_{1-6}$ alkyl$)_2$-N—, wherein the definition of "$C_{1-6}$ alkyl" is as described above.

As used herein, the terms "$C_{1-4}$ alkoxy", "$C_{1-4}$ alkylamino", and "di($C_{1-4}$ alkyl)amino" refer to the groups in a form of $C_{1-4}$ alkyl-O—, $C_{1-4}$ alkyl-NH—, and $(C_{1-4}$ alkyl$)_2$-N—, wherein the definition of "$C_{1-4}$ alkyl" is as described above.

As used herein, the terms "halo $C_{1-6}$ alkyl", "halo $C_{1-6}$ alkylene", "hydroxy $C_{1-6}$ alkyl", "amino $C_{1-6}$ alkyl", and "halo $C_{1-6}$ alkoxy" refer to the groups formed by replacing hydrogen atom(s) in $C_{1-6}$ alkyl, $C_{1-6}$ alkylene, and $C_{1-6}$ alkoxy with one to more, e.g., 1-4, 1-3 or 1-2, halogen atoms, hydroxyl and amino groups, respectively.

As used herein, the terms "halo $C_{1-4}$ alkyl", "halo $C_{1-4}$ alkylene", "hydroxy $C_{1-4}$ alkyl", "amino $C_{1-4}$ alkyl", and "halo $C_{1-4}$ alkoxy" refer to the groups formed by replacing hydrogen atoms in $C_{1-4}$ alkyl, $C_{1-4}$ alkylene, and $C_{1-4}$ alkoxy with one to more, e.g., 1-4, 1-3, 1-2, halogen atoms, hydroxyl, and amino groups, respectively.

The term "3-14 membered cycloalkyl" as used in the present invention refers to a saturated or partially saturated non-aromatic cyclic alkyl group containing 3-14 carbon atoms, including "3-8 membered cycloalkyl" and "8-14 membered fused cycloalkyl", and preferably "3-12 membered cycloalkyl" and "3-10 membered cycloalkyl".

The term "3-8 membered cycloalkyl" as used in the present invention refers to a saturated or partially saturated monocyclic non-aromatic cyclic alkyl containing 3-8 carbon atoms, including "3-8 membered saturated cycloalkyl" and "3-8 membered partially saturated cycloalkyl"; preferably "3-4 membered cycloalkyl", "3-5 membered cycloalkyl", "3-6 membered cycloalkyl", "3-7 membered cycloalkyl", "4-5 membered cycloalkyl", "4-6 membered cycloalkyl", "4-7 membered cycloalkyl", "4-8 membered cycloalkyl", "5-6-membered cycloalkyl", "5-7 membered cycloalkyl", "5-8 membered cycloalkyl", "6-7 membered cycloalkyl", "6-8 membered cycloalkyl", "7-8-membered cycloalkyl", "3-6 membered saturated cycloalkyl", "4-7 membered saturated cycloalkyl", "4-8 membered saturated cycloalkyl", "5-8 membered saturated cycloalkyl", "5-7 membered saturated cycloalkyl", "5-6 membered saturated cycloalkyl", "3-6 membered partially saturated cycloalkyl", "4-7 membered partially saturated cycloalkyl", "4-8-membered partially saturated cycloalkyl", "5-8 membered partially saturated cycloalkyl", "5-7 membered partially saturated cycloalkyl", and "5-6 membered partially saturated cycloalkyl", etc. Specific examples of said "3-8 membered saturated cycloalkyl" include, but are not limited to: cyclopropyl, cyclobutanyl, cyclopentyl, cyclohexyl, cycloheptyl, and cyclooctyl, etc. Specific examples of said "3-8 membered partially saturated cycloalkyl" include, but are not limited to cyclopropenyl, cyclobutenyl, cyclopentenyl, cyclopentadienyl, cyclohexenyl, cyclohex-1,3-dienyl, cyclohex-1,4-dienyl, cycloheptenyl, cyclohept-1,3-dienyl, cyclohept-1,4-dienyl, cyclohept-1,3,5-trienyl, cyclooctenyl, cyclooctyl-1,3-dienyl, cyclooctyl-1,4-dienyl, cyclooctyl-1,5-dienyl, cyclooctyl-1,3,5-trienyl, and cyclooctatetraenyl, etc.

The term "8-14 membered fused ring group" as used in the present invention refers to a saturated or partially saturated, non-aromatic cyclic group containing 8-14 ring atoms which is formed by two or more ring structures sharing two adjacent carbon atoms with each other. One of the fused rings may be an aromatic ring, but the fused rings as a whole do not have aromaticity. Said "8-14 membered fused ring group" includes "8-12 membered fused ring group", "8-10 membered fused ring group", "8-9 membered fused ring group", and "9-10 membered fused ring group", etc, which may be formed by fusing 5-6 membered cycloalkyl with 5-6 membered cycloalkyl, benzene with 5-6 membered cycloalkyl, and benzene with 5-6 membered saturated cycloalkyl, etc. Specific examples thereof include, but are not limited to: bicyclo[3.1.0]hexyl, bicyclo[4.1.0]heptyl, bicyclo[2.2.0]hexyl, bicyclo[3.2.0]heptyl, bicyclo[4.2.0]octyl, octahydropentalenyl, octahydro-1H-indenyl, decahydronaphthalyl, tetradecahydrophenanthryl, bicyclo[3.1.0]hex-2-enyl, bicyclo[4.1.0]hept-3-enyl, bicyclo[3.2.0]hept-3-enyl, bicyclo[4.2.0]oct-3-enyl, 1,2,3,3a-tetrahydrocyclopentadienyl, 2,3,3a,4,7,7a-hexahydro-1H-indenyl, 1,2,3,4,4a,5,6,8a-octahydronaphthyl, 1,2,4a,5,6,8a-hexahydronaphthyl, 1,2,3,4,5,6,7,8,9,10-decahydrophenanthryl, benzocyclopentyl, benzocyclohexyl, benzocyclohexenyl, and benzocyclopentenyl, etc.

The term "3-14 membered heterocyclic group" as used in the present invention refers to a saturated or partially saturated, non-aromatic cyclic group containing 3-14 ring atoms and at least one (for example, 1, 2, 3, 4, or 5) heteroatom(s) which is nitrogen atom, oxygen atom and/or sulfur atom; optionally, the ring atom in the ring structure (such as carbon atom, nitrogen atom or sulfur atom) may be oxo. Said "3-14 membered heterocyclic group" includes "3-8 membered heterocyclic group" and "8-14 membered fused heterocyclic group", and preferably 3-12 membered heterocyclic group and 3-10 membered heterocyclic group.

The term "3-8 membered heterocyclic group" as used in the present invention refers to a saturated or partially saturated, non-aromatic, monocyclic cyclic group containing 3-8 ring atoms and at least one (for example, 1, 2, 3, 4, or 5) heteroatom(s) which is nitrogen atom, oxygen atom and/or sulfur atom; optionally, the ring atom in the ring structure (such as carbon atom, nitrogen atom or sulfur atom) may be oxo. Said "3-8 membered heterocyclic group" includes "3-8 membered saturated heterocyclic group" and "3-8 membered partially saturated heterocyclic group". Preferably, said "3-8 membered heterocyclic group" in the present invention contains 1-3 heteroatoms. Preferably, said "3-8 membered heterocyclic group" in the present invention contains 1-2 heteroatom(s), and the heteroatom(s) are selected from nitrogen atom and/or oxygen atom. Preferably, said "3-8 membered heterocyclic group" in the present invention contains one nitrogen atom. Said "3-8 membered heterocyclic group" is preferably "3-7 membered heterocyclic group", "3-6 membered heterocyclic group", "4-7 membered heterocyclic group", "4-6 membered heterocyclic group", "6-8 membered heterocyclic group", "5-7 membered heterocyclic group", "5-6 membered heterocyclic group", "3-6 membered saturated heterocyclic group", "4-6 membered saturated heterocyclic group", "5-6 membered saturated heterocyclic group", "3-6 membered nitrogen-containing heterocyclic group", "3-6 membered saturated nitrogen-containing heterocyclic group", "4-6 membered nitrogen-containing heterocyclic group", "4-6 membered saturated nitrogen-containing heterocyclic group", "5-6 membered nitrogen-containing heterocyclic group", and "5-6 membered saturated nitrogen-containing heterocyclic group", etc. Specific examples of "3-8 membered heterocyclic group" include, but are not limited to: aziridinyl, 2H-aziridinyl, diaziridinyl, 3H-diazacyclopropenyl, azetidinyl, 1,4-dioxanyl, 1,3-dioxanyl, 1,3-dioxolanyl, 1,4-dioxacyclohexadienyl, tetrahydrofuranyl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, thiazolidinyl, piperidinyl, tetrahydropyridinyl, piperidinonyl, tetrahydropyridinonyl, dihydropiperidinonyl, piperazinyl, morpholinyl, 4,5-dihydrooxazolyl, 4,5-dihydroisoxazolyl, 2,3-dihydroisoxazolyl, oxazolidinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, 4H-1,3-thiazinyl, 6H-1,3-thiazinyl, 2H-pyranyl, 2H-pyran-2-onyl, and 3,4-dihydro-2H-pyranyl, etc.

The term "8-14 membered fused heterocyclic group" as used in the present invention refers to a saturated or partially saturated, non-aromatic cyclic group containing 8-14 ring atoms and with at least one heteroatom(s) which is formed by two or more than two ring structures sharing two adjacent atoms with each other, wherein one of the fused rings may be an aromatic ring, but the fused rings as a whole do not have aromaticity, the heteroatom is nitrogen atom, oxygen atom and/or sulfur atom; optionally, the ring atom (such as carbon atom, nitrogen atom or sulfur atom) in the ring structure may be oxo. Said "8-14 membered fused heterocyclic group" includes but is not limited to "8-9 membered fused heterocyclic group", "9-10 membered fused heterocyclic group", etc, which may be formed by fusing 5-6 membered heterocyclic group with 5-6 membered heterocyclic group, 5-6 membered heterocyclic group with 5-6 membered cycloalkyl, benzene with 5-6 membered heterocyclic group, benzene with 5-6 membered saturated heterocyclic group, 5-6 membered heteroaryl with 5-6 membered heterocyclic group, or 5-6 membered heteroaryl with 5-6 membered saturated heterocyclic group, wherein said 5-6 membered heteroaryl is as defined above. Specific examples of said "8-10 membered fused heterocyclic group" include but are not limited to: pyrrolidinocyclopropyl, cyclopentylazacyclopropyl, pyrrolidinocyclobutyl, pyrrolidinopyrrolidinyl, pyrrolidinopiperidinyl, pyrrolidinopiperazinyl, pyrrolidinomorpholinyl, piperidinomorpholinyl, benzopyrrolidinyl, benzocyclopentyl, benzocyclohexyl, benzotetrahydrofuranyl, benzopyrrolidinyl, benzimidazolidinyl, benzoxazolidinyl, benzothiazolidinyl, benzoisoxazolidinyl, benzoisothiazolidinyl, benzopiperidinyl, benzomorpholinyl, benzopiperazinyl, benzotetrahydropyranyl, pyridocyclopentyl, pyridocyclohexyl, pyridotetrahydrofuranyl, pyridopyrrolidinyl, pyridoimidazolidinyl, pyridooxazolidinyl, pyridothiazolidinyl, pyridoisoxazolidinyl, pyridoisothiazolidinyl, pyridopiperidinyl, pyridomorpholinyl, pyridopiperazinyl, pyridotetrahydropyranyl, pyrimidocyclopentyl, pyrimidocyclohexyl, pyrimidotetrahydrofuranyl, pyrimidopyrrolidinyl, pyrimidoimidazolidinyl, pyrimidooxazolidinyl, pyrimidothiazolidinyl, pyrimidoisoxazolidinyl, pyrimidoisothiazolidinyl, pyrimidopiperidinyl, pyrimidomorpholinyl, pyrimidopiperazinyl, pyrimidotetrahydropyranyl; tetrahydroimidazo[4,5-c]pyridyl, 3,4-dihydroquinazolinyl, 1,2-dihydroquinoxalinyl, benzo[d][1,3]dioxolyl, 2H-chromenenyl, 2H-chromenen-2-onyl, 4H-chromenyl, 4H-chromen-4-onyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, octahydro-benzo[d]imidazolyl, decahydroquinolinyl, hexahydrothienoimidazolyl, hexahydrofuroimidazolyl, 4,5,6,7-tetrahydro-1H-benzo[d]imidazolyl, octahydrocyclopenteno[c]pyrrolyl, and 4H-1,3-benzoxazinyl, etc.

The term "6-12-membered aryl" as used in the present invention refers to an aromatic cyclic group containing 6-12 ring carbon atoms, including "6-8-membered monocyclic aryl" and "8-12-membered fused aryl", and preferably 6-10 membered aryl.

The term "6-8 membered monocyclic aryl" as used in the present invention refers to a monocyclic aryl group containing 6-8 ring carbon atoms; specific examples thereof include, but are not limited to: phenyl, cyclooctatetraenyl, etc., and preferably phenyl.

The term "8-12 membered fused aryl" as used in the present invention refers to an unsaturated, aromatic cyclic group containing 8-12 ring carbon atoms which is formed by two or more ring structure(s) sharing two adjacent atoms with each other; and is preferably a "9-10 membered fused aryl group"; and specific examples thereof includes naphthyl and the like.

The term "5-12 membered heteroaryl" as used in the present invention refers to an aromatic cyclic group containing 5-12 ring atoms (at least one of which is heteroatom, such as nitrogen atom, oxygen atom or sulfur atom). Said "5-12 membered heteroaryl" includes "5-8 membered monocyclic heteroaryl" and "8-12 membered fused heteroaryl", and preferably 5-10 membered heteroaryl.

The term "5-8 membered monocyclic heteroaryl" as used in the present invention refers to a monocyclic cyclic group containing 5-8 ring atoms (at least one of which is heteroatom, such as nitrogen atom, oxygen atom or sulfur atom). Optionally, the ring atoms (e.g., carbon atoms, nitrogen atoms, or sulfur atoms) in the ring structure may be oxo. Said "5-8 membered monocyclic heteroaryl" includes, for example, "5-7 membered monocyclic heteroaryl", "5-6 membered monocyclic heteroaryl", "5-6 membered nitrogen-containing monocyclic heteroaryl", and "5 membered nitrogen-containing monocyclic heteroaryl", etc. Specific examples of "5-8 membered monocyclic heteroaryl" include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidinyl, pyridazinyl, pyrazinyl, 1,2,3-triazinyl, 1,3,5-triazinyl, 1,2,4,5-tetrazinyl, azepinyl, 1,3-diazepinyl, and azacyclooctatetraenyl, etc. Said "5-6 membered heteroaryl" refers to specific examples containing 5-6 ring atoms of 5-8 membered heteroaryl.

The term "8-12 membered fused heteroaryl" as used in the present invention refers to an unsaturated, aromatic ring structure containing 8-12 ring atoms (wherein at least one of which is heteroatom, such as nitrogen atom, oxygen atom or sulfur atom) formed by two or more ring structures sharing two adjacent atoms with each other. Optionally, the ring atoms (e.g., carbon atoms, nitrogen atoms, or sulfur atoms) in the ring structure may be oxo. Said "8-12 membered fused heteroaryl" includes "9-10 membered fused heteroaryl", and "8-9 membered fused heteroaryl", etc, which may be formed by fusing benzene with 5-6 membered heteroaryl, or 5-6 membered heteroaryl with 5-6 membered heteroaryl, etc. Specific examples include but are not limited to: pyrrolopyrrole, pyrrolofuran, pyrazolopyrrole, pyrazolothiophene, furothiophene, pyrazolooxazole, benzofuranyl, benzoisofuranyl, benzothienyl, indolyl, isoindolyl, benzoxazolyl, benzimidazolyl, indazolyl, benzotriazolyl, quinolinyl, 2-quinolinonyl, 4-quinolinonyl, 1-isoquinolinonyl, isoquinolinyl, acridinyl, phenanthridinyl, benzopyridazinyl, phthalazinyl, quinazolinyl, quinoxalinyl, purinyl, naphthyridinyl and the like.

The term "5-12-membered bridged group" as used in the present invention refers to a structure containing 5-12 carbon atoms formed by any two rings sharing two atoms that are not directly connected. Said "5-12-membered bridged group" includes 5-12 membered saturated bridged group, and 5-12-membered partially saturated bridged cyclic group; and preferably 5-10 membered bridged group, 5-8 membered bridged group, 5-10 membered saturated bridged group, 5-8 membered saturated bridged group, 6-10 membered saturated bridged group, and 7-12 membered partially saturated bridged groups. Specific examples of said 5-12 membered bridged group includes but are not limited to bicyclo[2.1.1]hexyl, bicyclo[2.2.1]heptyl, bicyclo[2.2.2]octyl, bicyclo[3.2.1]octyl, bicyclo[3.3.1]nonyl, bicyclo[2.2.1]hept-5-enyl, bicyclo[3.2.1]oct-6-enyl, dicyclopentadienyl, etc.

The term "5-12-membered bridged heterocyclic group" as used in the present invention refers to the group that at least one ring carbon atom in the above-mentioned 5-12-membered bridged cyclic group is substituted with heteroatom selected from O, S, and N, preferably 1-3 heteroatoms. It also includes the cases where carbon atom(s), nitrogen atom(s), and sulfur atom(s) are oxo. 5-10 membered bridged heterocyclic groups and 5-8 membered bridged heterocyclic groups are preferred.

The term "5-12 membered spirocyclic group" as used in the present invention refers to a structure containing 5-12 carbon atoms formed by at least two rings sharing one atom, including 5-12 membered saturated spirocyclic group and 5-12 membered partially saturated spirocyclic group. Specific examples of said 5-12 membered saturated spirocyclic group include but are not limited to the group formed by substituting any replaceable hydrogen atom with a ring structure such as

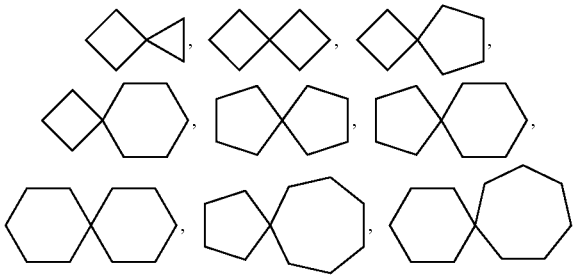

and the like. 5-12 membered partially saturated spirocyclic group refers to the spirocyclic group with at least one ring being a unsaturated cyclic group. Specific examples thereof include the group formed by substituting any replaceable hydrogen atom with a ring structure such as

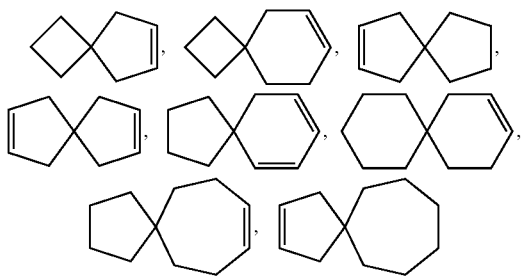

and the like. Preferred is 5-8 membered spirocyclic group, including "5-8 membered saturated spirocyclic group" and "5-8 membered unsaturated spirocyclic group".

The term "5-12 membered spiroheterocyclic group" as used in the present invention refers to the 5-12 membered spirocyclic group in which at least one ring carbon atom is substituted with a heteroatom, preferably 1-3 heteroatom(s), selected from O, S, and N. It also includes those in which carbon atom(s), nitrogen atom(s) and sulfur atom(s) are oxo. Preferred is 5-10 membered spiroheterocyclic group, 5-8 membered spiroheterocyclic group, and 5-6 membered spiroheterocyclic group.

The term "optionally substituted with" as used in the present invention includes both "substituted with" and "unsubstituted with".

The term "therapeutically effective amount" as used in the present invention refers to the amount of the aforementioned compound, the pharmaceutical formulation, and the pharmaceutical composition that may at least alleviate the symptoms of a patient's condition(s) when being administered to the patient. The actual amount including the "therapeutically effective amount" varies according to various conditions, including but not limited to the specific conditions being treated, the severity of the condition, the physical and healthy status of the patient, and the route of administration. A skilled medical practitioner can easily determine the appropriate amount using methods known in the medical field.

Advantageous technical effects of the present invention:
(1) The present compound, the pharmaceutically acceptable salt, the ester or the stereoisomer thereof has excellent KHK inhibitory activity, and may treat and/or prevent KHK-mediated diseases and related conditions;
(2) the present compound, the pharmaceutically acceptable salt, the ester or the stereoisomer thereof has good pharmacokinetic properties, a longer-lasting effect, and high bioavailability;
(3) the present compound, the pharmaceutically acceptable salt, the ester or the stereoisomer thereof has good safety; and
(4) the present compound requires simple preparation process, has high drug purity and stable quality, and is easy for large-scale industrial production.

The beneficial effects of the compounds provided in the examples of the present invention are further illustrated by the following experiments. However, it should not be understood that the compounds provided in the examples of the present invention only have the following beneficial effects.

Experimental Example 1. Test on the Compounds Provided as in Examples of the Present Invention for Inhibitory Activity Against KHK Kinase In Vitro Test compounds: the compounds provided in Examples of the present invention, the chemical names and preparation methods thereof can be found in the Preparation Examples.

Control drug: PF-06835919, prepared by referring to the method in the document (U.S. Ser. No. 15/381,295).

Experimental Reagents:

| Reagent | Vendor | Cat No. |
| --- | --- | --- |
| HEPES | Life Technologies | 15630-080 |
| ADP-GloTM Kinase Assay kit | Promega | V9102 |
| D-Fructose | Sigma | F2543 |
| KHK-C | Origene | TP323488 |
| Brij 35 detergent | Merck | 203728 |
| ATP | Promega | V915B |
| $MgCl_2$ | Sigma | M1028 |
| KCl | Sigma | P9541 |
| DMSO | MP | 196055 |

| Reagent | Vendor | Cat No. |
|---------|--------|---------|

Experimental Consumables:

| Consumables | Vendor | Cat No. |
|-------------|--------|---------|
| Topseal A | PerkinElmer | E5341 |
| 96 Well Plate | Nunc | 249944 |
| 384-Well Polypropylene microplate | Labcyte | P-05525 |
| Optiplate-384 | Perkin Elmer | 6007290 |

Experimental Instruments:

| Instrument | Vendor | Cat No. |
|------------|--------|---------|
| Echo 550 Liquid Handler | Labcyte | Echo 550 |
| Plate reader | Perkin Elmer | Envision 2104 |
| Centrifuge | Eppendorf | 5810R |
| Multi-channel pipettes | Eppendorf/Sartorius | / |

Experimental Protocol I:
1. Compound Dilution
    1) The present compounds and the control drug were formulated in DMSO to 10 mM as stock solutions for test.
    2) The stock solutions of the compounds of the present invention and the control drug were diluted by 10-fold to 1 mM, and then further diluted in a 3-fold gradient to 11 concentrations, with the highest concentration being 1 mM.
    3) 0.1 μL of the compounds of the present invention and the control drug as diluted was transferred with Echo550 to a 384-well plate, in duplicate per concentration, and centrifuged at 1000 rpm for 1 min.
2. Enzyme Reaction Test
    1) 5 μL of KHK-C kinase working solution was added to the 384-well plate, centrifuged at 1000 rpm for 1 min, and incubated at room temperature of 25° C. for 15 min.
    2) 5 μL of the substrate working solution was added to the 384-well plate to initiate the kinase reaction, centrifuged at 1000 rpm for 1 min, and incubated at room temperature of 25° C. for 60 min.
    3) The final concentrations of the KHK-C kinase reaction were 1 nM for KHK-C, 100 μM for ATP, 200 μM for D-Fructose, 50 mM for HEPES, 10 mM for MgCl$_2$, and 0.01% for Brij35, and the final concentration of DMSO was 1%.
    4) The final concentrations of the test compounds and the control drug were 10000 nM, 3333.33 nM, 1111.11 nM, 370.37 nM, 123.457 nM, 41.15 nM, 13.71 nM, 4.572 nM, 1.524 nM, 0.508 nM, and 0.169 nM, respectively.
3. Reaction Termination and Detection
    1) The 384-well plate was added with 10 μL of the ADP Glo reagent, centrifuged at 1000 rpm for 1 min, and then incubated at room temperature of 25° C. for 40 min.
    2) The 384-well plate was added with 20 μL of the kinase detection reagent, centrifuged at 1000 rpm for 1 min, and then incubated at room temperature of 25° C. for 40 min.
    3) After the reaction was completed, the fluorescence value LUM was read on Envision.
4. Data Analysis
The following equation was used to calculate the inhibition (% inh):

$$\text{inhibition (\%)} = 100\% \times \frac{Lum_{HC} - Lum_{CPD}}{Lum_{HC} - Lum_{LC}}$$

wherein,
$Lum_{HC}$ represents luminescence signal intensity of High control (with the same volume of DMSO as the test compound added to the reaction);
$Lum_{LC}$ represents luminescence signal intensity of Low control (the control drug at 10 μM); and
$Lum_{cpd}$ represents luminescence signal intensity of the test compound.
GraphPad Prism 5.0 software was used for curve fitting to calculate IC$_{50}$.

Experimental Results:

TABLE 2

Inhibitory activity of the compounds in Examples of the present invention against KHK-C

| Compound | IC$_{50}$(nM) |
|----------|---------------|
| PF-06835919 | 7.07 |
| Compound 2 | 0.52 |

It can be seen from the above experimental results that the compounds as provided in the Examples of the present invention may effectively inhibit the activity of KHK-C kinase and are effective KHK-C kinase inhibitors.

Experimental Protocol II:
1. Compound Dilution
    1) The compounds of the present invention and the control drug were formulated in DMSO to 10 mM as stock solutions for test.
    2) The stock solutions of the compounds of the present invention were diluted by 10-fold to 1 mM, and then further diluted in a 3-fold gradient to 11 concentrations, with the highest concentration being 1 mM. The stock solution of the control drug was diluted by 100-fold to 0.1 mM, and then further diluted in a 3-fold gradient to 11 concentrations, with the highest concentration being 0.1 mM.
    3) 0.1 μL of the compounds of the present invention and the control drug as diluted was transferred with Echo550 to a 384-well plate, in duplicate per concentration, and then centrifuged at 1000 rpm for 1 min.
2. Enzyme Reaction Test
    1) 5 μL of KHK-C kinase working solution was added to the 384-well plate, centrifuged at 1000 rpm for 1 min, and then incubated at room temperature of 25° C. for 15 min.
    2) 5 μL of the substrate working solution was added to the 384-well plate to initiate the kinase reaction, centrifuged at 1000 rpm for 1 min, and incubated at room temperature of 25° C. for 60 min.
    3) The final concentrations of the KHK-C kinase reaction system were 1 nM for KHK-C, 100 μM for ATP, 200 μM for D-Fructose, 50 mM for HEPES, 10 mM for MgCl$_2$, and 0.01% for Brij35, and the final concentration of DMSO was 1%.

4) The final concentrations of the test compounds were 10000 nM, 3333.33 nM, 1111.11 nM, 370.37 nM, 123.457 nM, 41.15 nM, 13.71 nM, 4.572 nM, 1.524 nM, 0.508 nM, and 0.169 nM, respectively.
5) The final concentrations of the control drug were 1000 nM, 333.33 nM, 111.11 nM, 37.037 nM, 12.346 nM, 4.115 nM, 1.371 nM, 0.4572 nM, 0.1524 nM, 0.0508 nM, and 0.0169 nM, respectively.

3. Reaction Termination and Detection
1) The 384-well plate was added with 10 μL of the ADP Glo reagent, centrifuged at 1000 rpm for 1 min, and then incubated at room temperature of 25° C. for 40 min.
2) The 384-well plate was added with 20 μL of the kinase detection reagent, centrifuged at 1000 rpm for 1 min, and then incubated at room temperature of 25° C. for 40 min.
3) After the reaction was completed, the fluorescence value LUM was read on Envision.

4. Data Analysis
The following equation was used to calculate the inhibition (% inh):

$$\text{inhibition (\%)} = 100\% \times \frac{Lum_{HC} - Lum_{CPD}}{Lum_{HC} - Lum_{LC}}$$

wherein,
$Lum_{HC}$ represents luminescence signal intensity of High control (with the same volume of DMSO as the test compound added to the reaction);
$Lum_{LC}$ represents luminescence signal intensity of Low control (the control drug at 1 μM); and
$Lum_{cpd}$ represents luminescence signal intensity of the test compound.
GraphPad Prism 5.0 software was used for curve fitting to calculate $IC_{50}$.

Experimental Results:

TABLE 3

Inhibitory activity of the compounds in the Examples of the present invention against KHK-C

| Compound | IC$_{50}$(nM) |
|---|---|
| PF-06835919 | 9.5 |
| Compound 1 | 0.82 |
| Compound 3-1 | 0.73 |
| Compound 4-1 | 2.2 |
| Compound 4-2 | 1.5 |
| Compound 6-1 | 0.90 |

Other specific compounds were also tested with the above experimental protocol for the inhibitory activity against KHK-C kinase. The test compound 1-2, compound 5-1, compound 7, compound 10, compound 14, and compound 15 etc. showed good inhibitory activity against KHK-C (1 nM-0.3 μM).

It can be seen from the above experimental results that the compounds as provided in the Examples of the present invention may effectively inhibit the activity of KHK-C kinase and are effective KHK-C kinase inhibitors.

Experimental Example 2. Test on the Compounds as Provided in Examples of the Present Invention for Inhibitory Activity in Cells In Vitro Test compounds: the compounds provided in Examples of the present invention, the chemical names and preparation methods thereof can be found in the Preparation Examples.

Control drug: PF-06835919, prepared by referring to the method in the document (U.S. Ser. No. 15/381,295).

Experimental Reagents:

| Reagent | Vendor | Cat No. |
|---|---|---|
| MEM medium | Gibco | 10370-021 |
| HepG2 hepatoma cell | ATCC | HB-8065 |
| sodium pyruvate | Gibco | 11360-070 |
| glutamine | Gibco | 35050-061 |
| Fetal Bovine Serum (FBS) | Gibco | 10091-148 |
| DPBS buffer | Gibco | 14200-075 |
| 0.25% trypsin (containing EDTA) | Gibco | 25200-072 |
| DMSO | Sigma | D4540 |
| Penicillin&Streptomycin | Gibco | 10378016 |
| Ammonium acetate | TEDIA | AS0139-028 |
| D-fructose | sigma | F3510-100G |

Experimental Instruments:

| Instrument | Vendor | Cat No. |
|---|---|---|
| CO$_2$ Incubator | SANYO | MCO-15A4 |
| biosafety cabinet | Shanghai Lishen Technology Instrument Co., Ltd | 1200A2 |
| refrigerated centrifuge | Eppendorf | Centrifuge5840R |
| microscope | Nikon | TS100-F |

Experimental Protocol:
1. Cell Culture and Inoculation
1) HepG2 cells in the logarithmic growth phase were collected and counted with a platelet counter. The Trypan blue exclusion method was used to detect cell viability and ensure that cell viability is 90% or above.
2) The concentration of HepG2 cells was adjusted, and 81 μL of the cell suspension in a FBS-free basal medium (starvation treatment) was add to a 96-well plate, with a cell inoculum amount of $5 \times 10^4$ cells per test well.
3) The HepG2 cells in the 96-well plate were cultured overnight at 37° C., 5% $CO_2$, and 95% humidity.
2. Administration
1) Before administration, 9 μL of FBS was added to the test wells of the 96-well plate to stop the starvation treatment.
2) 10× stock solutions of the individual test compounds were prepared by dilution in a 3-fold gradient to 8 concentrations, with the highest concentration of 100 μM. 10 μL of the test compound solutions was added to each well of the 96-well plate inoculated with the cells, in triplicate per test compound concentration. For the solvent control, 10 μL of 1% DMSO solution was added to each well, in triplicate.
3) The cells in the 96-well plate added with the test compounds were incubated at 37° C., 5% $CO_2$, and 95% humidity for 30 min.
4) An 11-fold D-Fructose solution was prepared at the concentration of 220 mM. 10 μL of the D-Fructose solution was added to the 96-well plate inoculated with HepG2 cells per well, in triplicate. For the solvent control, 10 μL of 11% DPBS solution was added, in triplicate.
5) The cells in the 96-well plate added with D-fructose were incubated at 37° C., 5% $CO_2$, and 95% humidity for 3 hours.
3. Sample Treatment
The medium in the 96-well plate was removed, and the cells in the 96-well plate were washed with cold DPBS (200

μl/well) for 3 times. 30 μL of cold 10 mM ammonium acetate (pH 7.4) was added into each well to lyse the cells (hypotonic lysis). After lysis on ice for 5 minutes, the cells were fully pipetted and the cell lysate was taken for LC-MS analysis.

4. Data Analysis

The data were analyzed with GraphPad Prism 5.0 software, and fitted with nonlinear S-curve regression, so as to obtain a dose-effect curve to calculate the EC50 value.

5. Experimental Results:

TABLE 4

The inhibition effects of the compounds of the examples of the present invention on the production of fructose-1-phosphate induced by D-Fructose in HepG2 cells

| Compound | EC50 (nM) |
| --- | --- |
| PF-06835919 | 169.3 |
| Compound 1 | 21.9 |
| Compound 2 | 14.5 |
| Compound 3-1 | 7.3 |
| Compound 4-1 | 11.8 |
| Compound 4-2 | 18.2 |
| Compound 6-1 | 39 |

KHK-C kinase is expressed highest in the liver and can specifically metabolize fructose to produce fructose-1-phosphate. It can be seen from the above experimental results that the compounds in Examples of the present invention may effectively inhibit production of fructose-1-phosphate induced by D-Fructose in HepG2 cells, and are effective KHK-C inhibitors.

DETAILED DESCRIPTION OF THE EMBODIMENTS

The technical solutions of the present invention will be described in combination with the following specific examples, and the described examples are only a part of examples of the present invention, but not all the examples. Based on the examples in the present invention, any other examples obtained by the ordinary skilled person in the art without creative work are within the protection scope of the present invention.

The meanings of the abbreviations used in the following experiments are as follows: PE: petroleum ether; EA: ethyl acetate; DAST: diethylaminosulfur trifluoride; THF: tetrahydrofuran; NMP: N-methylpyrrolidone; DCM: dichloromethane; DCE: 1,2-dichloroethane; mCPBA: m-chloroperoxybenzoic acid; EtONa: sodium ethoxide; DBN: 1,5-diazabicyclo[4.3.0]non-5-ene; DIEA: N,N-diisopropylethylamine.

Preparation Examples

Example 1. Preparation of 2-((1R,5S,6R)-3-(7,7-difluoro-2-((S)-2-methylazetidin-1-yl)-6,7-dihydro-5H-cyclopenta[d]pyrimidin-4-yl)-3-azabicyclo[3.1.0]hexan-6-yl)acetic acid (Compound 1)

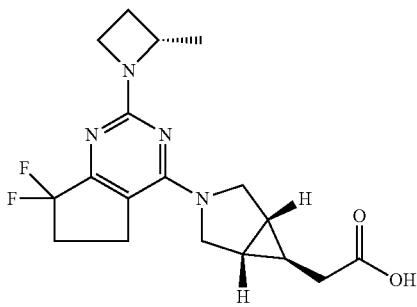 [SMILES: C[C@H]1CCN1c1nc(N2C[C@@H]3[C@@H](CC(=O)O)[C@@H]3C2)c2c(n1)C(F)(F)CC2]

(1) Preparation of 1-ethyl 2,4-dimethyl 1-oxobutane-1,2,4-tricarboxylate

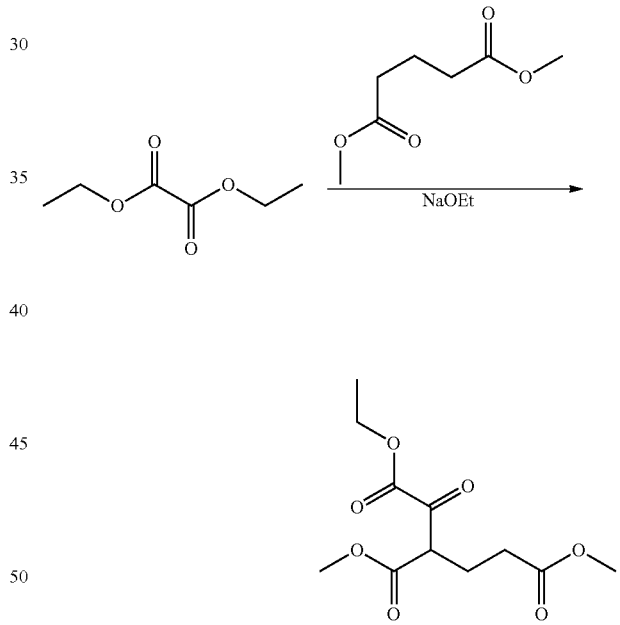

Metallic sodium (4.3 g, 186.9 mmol) was added into ethanol (200 mL). After the metallic sodium was completely dissolved, the resulting solution was spin-dried, and resuspended in tetrahydrofuran (200 mL). The solution was added with diethyl oxalate (27.4 g, 187.5 mmol) slowly, and then added with dimethyl glutarate (30.0 g, 187.3 mmol). The reaction was conducted at 25° C. for 16 hours, monitored by TLC (Rf=0.5, PE:EA=1:1), spin-dried, added with water (300 mL) and methyl tert-butyl ether (200 mL), and layer-separated. The aqueous phase was adjusted to pH 1, and extracted with 3×200 ml ethyl acetate. The organic phases were then combined, dried over anhydrous sodium sulfate, filtered, and spin-dried, and the residue was obtained for direct use in the next step.

(2) Preparation of 2-oxoadipic acid

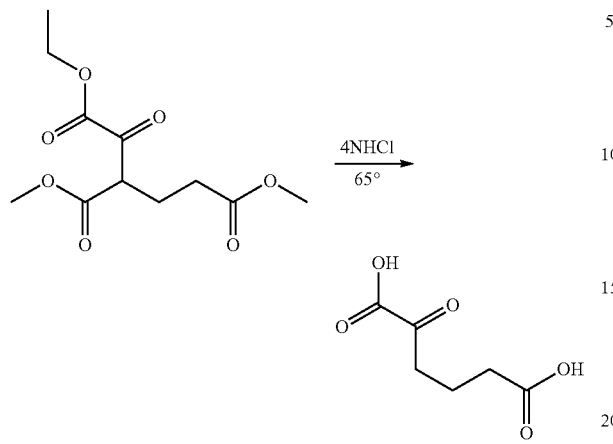

1-ethyl 2,4-dimethyl 1-oxobutane-1,2,4-tricarboxylate (the crude product in the previous step) was added into 4N hydrochloric acid (230 mL, 920 mmol) and heated to 65° C. for 6 hours. Then, the reaction was spin-dried, thus obtaining 21.0 g of the compound with a two-step yield of 70.0%.

(3) Preparation of 6-methoxy-5,6-dioxohexanoic acid

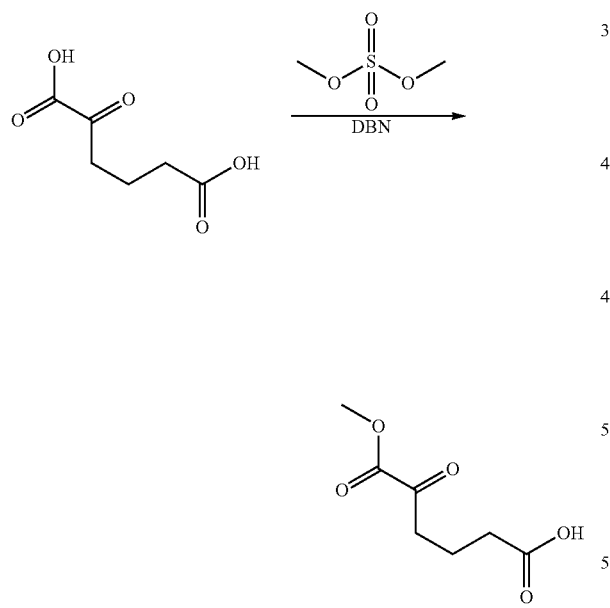

At 0° C., 2-oxoadipic acid (10.0 g, 62.5 mmol) was added into DBN (9.3 g, 74.9 mmol) in acetone (100 mL). The resulting solution was then added dropwise with dimethyl sulfate (7.9 g, 62.6 mmol). The reaction was carried out at 25° C. for 16 hours, spin-dried, added with water (50 mL), adjusted to pH 2-3, and extracted with 3×100 mL ethyl acetate. Then, the organic phases were combined, dried over anhydrous sodium sulfate, filtered, and spin-dried, and the residue was obtained for direct use in the next step.

(4) Preparation of dimethyl 2-oxohexanedioate

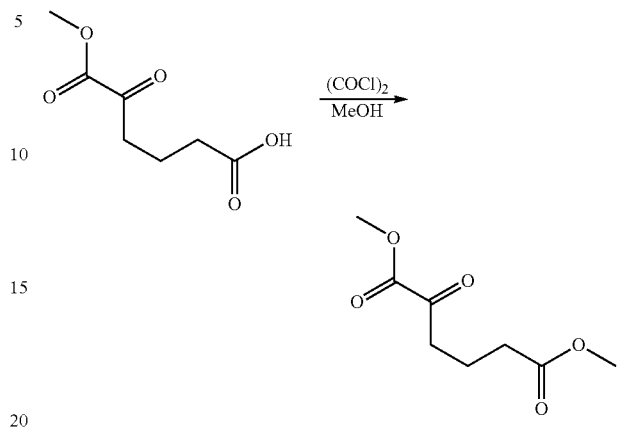

6-methoxy-5,6-dioxohexanoic acid (the crude product in the previous step) was dissolved in dichloromethane (100 mL), and the resulting solution was added with 2 drops of N,N-dimethylformamide, and then added with oxalyl chloride (15.9 g, 125.2 mmol) at 0° C. The reaction was carried out at 25° C. for 16 hours, and spin-dried, and the residue was added with methanol (40 mL) at 0° C., and then reacted at 25° C. for 2 hours. The reaction was spin-dried, and the residue was subjected to column chromatography (PE:EA=5:1), thus obtaining the product (7.9 g, two-step yield: 66.9%).

(5) Preparation of dimethyl 2,2-difluorohexanedioate

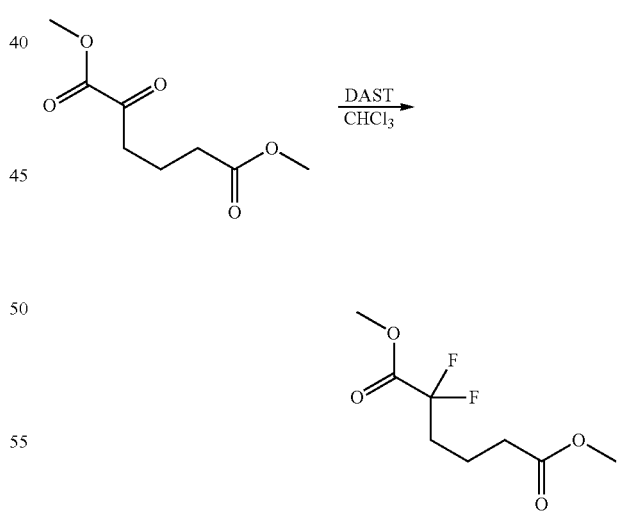

Dimethyl 2-oxohexanedioate (4.8 g, 25.5 mmol) was dissolved in chloroform (50 mL), and the resulting solution was added to DAST. The reaction was carried out at 25° C. for 48 hours, quenched by adding water, and extracted with 3×100 ml ethyl acetate. Then, the organic phases were combined, concentrated, and subjected to column chromatography (ethyl acetate:petroleum ether=1:3), thus obtaining the product (2.0 g, 37.0%).

(6) Preparation of methyl 3,3-difluoro-2-oxocyclopentane-1-carboxylate

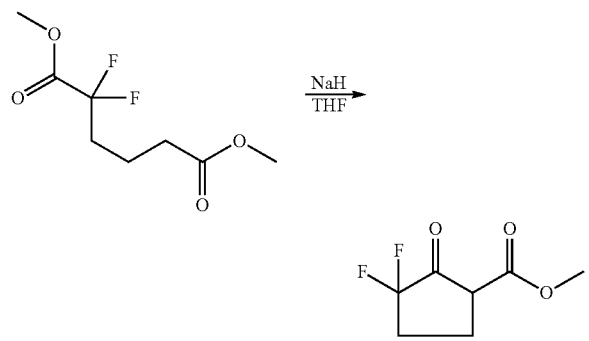

Sodium hydride (60%) (0.57 g, 14.2 mmol) was dissolved in THF (40 mL), and the resulting solution was added with dimethyl 2,2-difluorohexanedioate (2.0 g, 9.5 mmol) in THE (10 mL). The reaction was carried out at 20° C. for 16 hours, then quenched by adding water, adjusted to pH5-6, and extracted with 3×100 ml ethyl acetate. Then, the organic phases were combined, dried over anhydrous sodium sulfate, filtered, concentrated, thus obtaining the product for direct use in the next step (product 1.6 g, yield: 94.1%).

(7) Preparation of 7,7-difluoro-2-(methylthio)-6,7-dihydro-5H-cyclopenta[d]pyrimidin-4-ol

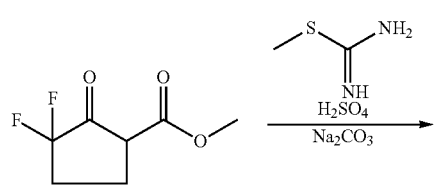

Methyl 3,3-difluoro-2-oxocyclopentane-1-carboxylate (2.4 g, 13.5 mmol) was dissolved in water (40 mL), and added with methyl isothiourea sulfate (3.8 g, 20.2 mmol) and sodium carbonate (2.85 g, 26.9 mmol). The reaction was carried out at 25° C. for 16 hours, adjusted to pH2 with 1N hydrochloric acid, and extracted with 3×100 ml ethyl acetate. Then, the organic phases were combined, dried over anhydrous sodium sulfate, filtered and concentrated, thus obtaining 2.4 g crude product for direct use in the next step.

(8) Preparation of 4-chloro-7,7-difluoro-2-(methylthio)-6,7-dihydro-5H-cyclopenta[d]pyrimidine

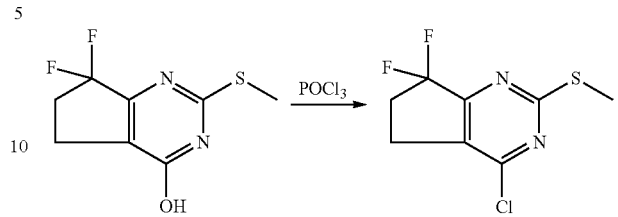

7,7-difluoro-2-(methylthio)-6,7-dihydro-5H-cyclopenta[d]pyrimidin-4-ol (2.4 g crude product) was dissolved in phosphorus oxychloride (5 mL)/1,2-dichloroethane (10 mL). The reaction was carried out at 110° C. for 16 h, concentrated, adjusted to pH7-8 with saturated sodium bicarbonate, and extracted with 3×80 ml ethyl acetate. Then, the organic phases were combined, concentrated, and subjected to column chromatography (ethyl acetate:petroleum ether=1:10), thus obtaining 1.4 g of the compound with a two-step yield of 43.8%.

(9) Preparation of methyl 2-((1R,5S,6s)-3-(7,7-difluoro-2-(methylthio)-6,7-dihydro-5H-cyclopenta[d]pyrimidin-4-yl)-3-azabicyclo[3.1.0]hexan-6-yl)acetate

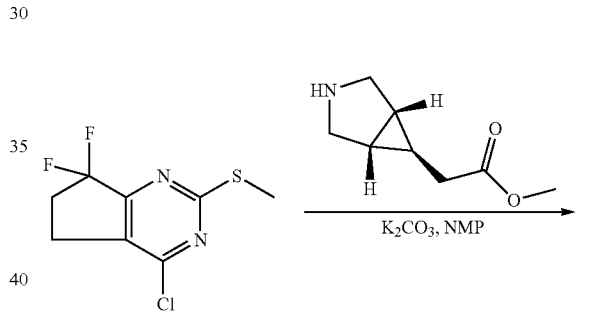

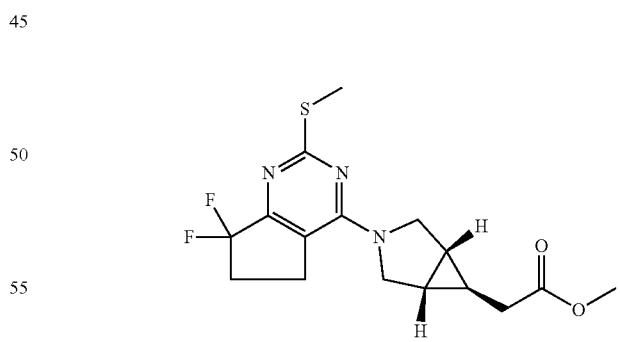

4-chloro-7,7-difluoro-2-(methylthio)-6,7-dihydro-5H-cyclopenta[d]pyrimidine (200 mg, 0.84 mmol) was dissolved in NMP (5 mL), and added with methyl 2-((1R,5S,6s)-3-azabicyclo[3.1.0]hexan-6-yl)acetate (160 mg, 1.03 mmol) and potassium carbonate (260 mg, 1.88 mmol). The reaction was carried out at 90° C. for 16 hours, added with water, and then extracted with 3×50 ml ethyl acetate. The organic phases were combined, and concentrated, thus obtaining the crude product for direct use in the next step.

(10) Preparation of methyl 2-((1R,5S,6s)-3-(7,7-difluoro-2-(methylsulfonyl)-6,7-dihydro-5H-cyclopenta[d]pyrimidin-4-yl)-3-azabicyclo[3.1.0]hexan-6-yl)acetate

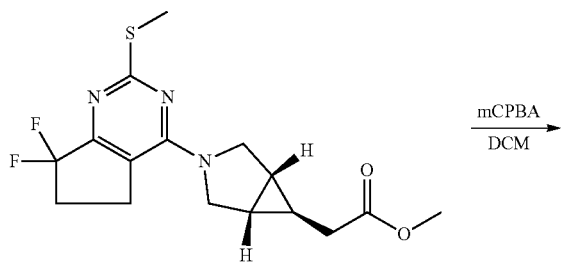

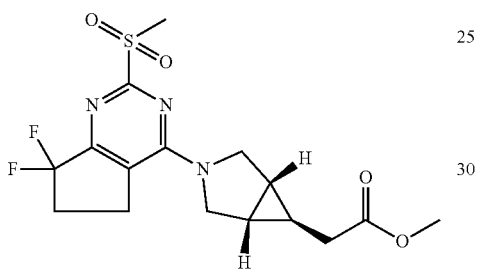

Methyl 2-((1R,5S,6s)-3-(7,7-difluoro-2-(methylthio)-6,7-dihydro-5H-cyclopenta[d]pyrimidin-4-yl)-3-azabicyclo[3.1.0]hexan-6-yl)acetate (the crude product from the previous step) was dissolved in dichloromethane (10 mL), and added with m-chloroperoxybenzoic acid (80%) (400 mg, 1.85 mmol). The reaction was carried out at 20° C. for 3 hours, added with saturated sodium carbonate solution, and layer-separated. The aqueous phase was extracted with 2×30 ml dichloromethane. Then, the organic phases were combined, spin-dried, and subjected to column chromatography (ethyl acetate:petroleum ether=3:1), thus obtaining 160 mg of the compound with two-step yield of 48.6%.

(11) Preparation of methyl 2-((1R,5S,6R)-3-(7,7-difluoro-2-((S)-2-methylazetidin-1-yl)-6,7-dihydro-5H-cyclopenta[d]pyrimidin-4-yl)-3-azabicyclo[3.1.0]hexan-6-yl)acetate

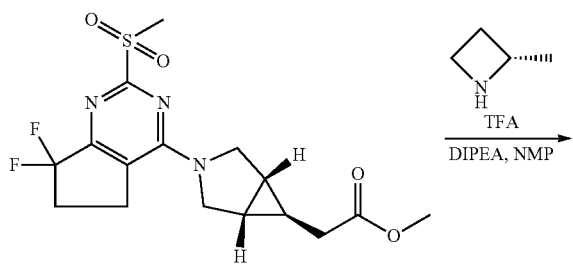

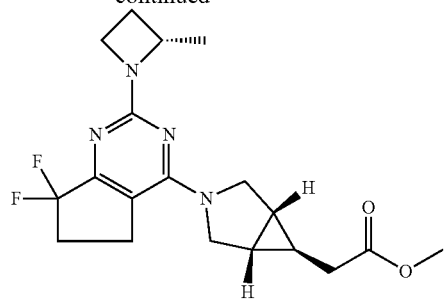

Methyl 2-((1R,5S,6s)-3-(7,7-difluoro-2-(methylsulfonyl)-6,7-dihydro-5H-cyclopenta[d]pyrimidin-4-yl)-3-azabicyclo[3.1.0]hexan-6-yl)acetate (100 mg, 0.26 mmol) was dissolved in NMP (3 mL), and added with DIEA (0.5 ml) and (S)-2-methylazetidine trifluoroacetate (107 mg, 0.58 mmol). Then, the reaction was subjected to microwave reaction at 160° C. for 2 hours, added with water, and extracted with 2×30 ml ethyl acetate. Then, the organic phases were combined, spin-dried, and subjected to column chromatography (Ethyl acetate:petroleum ether-1:1), thus obtaining 60 mg of the compound with yield of 61.4%.

(12) Preparation of 2-((1R,5S,6R)-3-(7,7-difluoro-2-((S)-2-methylazetidin-1-yl)-6,7-dihydro-5H-cyclopenta[d]pyrimidin-4-yl)-3-azabicyclo[3.1.0]hexan-6-yl)acetic acid

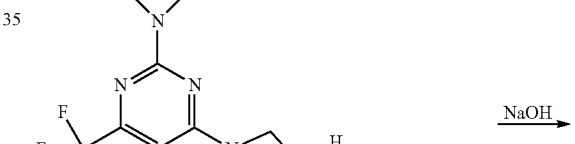

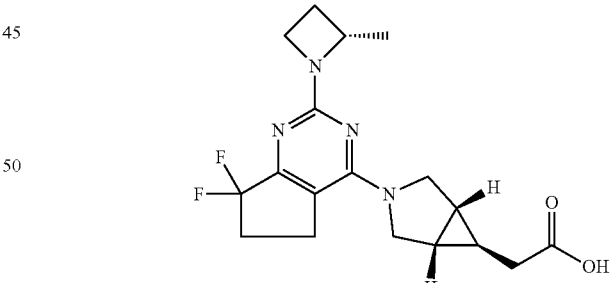

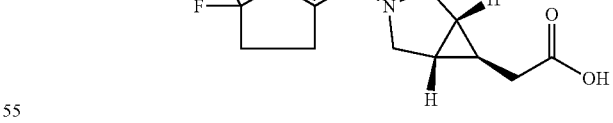

Methyl 2-((1R,5S,6R)-3-(7,7-difluoro-2-((S)-2-methylazetidin-1-yl)-6,7-dihydro-5H-cyclopenta[d]pyrimidin-4-yl)-3-azabicyclo[3.1.0]hexan-6-yl)acetate (60 mg, 0.16 mmol) was dissolved in MeOH/THF/H$_2$O (3/3/3 mL), and added with NaOH (26 mg, 0.65 mmol). The reaction was carried out for at 25° C. for 3 hours, adjusted to pH5 with 1N hydrochloric acid, concentrated, and subjected to column chromatography (ACN/H$_2$O=40:60), thus obtaining the product (38 mg, 65.8%).

Molecular formula: C$_{18}$H$_{22}$F$_2$N$_4$O$_2$; Molecular weight: 364.4; LC-MS (M/e): 365.0 (M+H$^+$)

¹HNMR (400 MHz, MeOD): δ: 4.38-4.43 (m, 1H), 3.98-4.05 (m, 3H), 3.84-3.91 (m, 1H), 3.61-3.68 (m, 2H), 3.04-3.09 (m, 2H), 2.31-2.48 (m, 3H), 2.30 (d, J=7.2 Hz, 2H), 1.90-1.96 (m, 1H), 1.56 (s, 2H), 1.48 (d, J=6.4 Hz, 3H), 0.85-0.89 (m, 1H).

Example 1-1. Preparation of 2-((1R,5S,6s)-3-(7,7-difluoro-2-(2-methylazetidin-1-yl)-6,7-dihydro-5H-cyclopenta[d]pyrimidin-4-yl)-3-azabicyclo[3.1.0]hexan-6-yl)acetic acid (Compound 1-1

(1) Preparation of methyl 2-((1R,5S,6s)-3-(2-chloro-7,7-difluoro-6,7-dihydro-5H-cyclopenta[d]pyrimidin-4-yl)-3-azabicyclo[3.1.0]hexan-6-yl)acetate

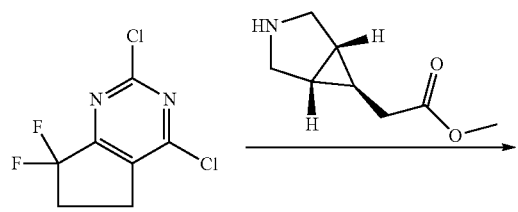

2,4-dichloro-7,7-difluoro-6,7-dihydro-5H-cyclopenta[d]pyrimidine (100 mg, 0.44 mmol) and methyl 2-((1R,5S,6s)-3-azabicyclo[3.1.0]hexan-6-yl)acetate (70 mg, 0.45 mmol) were dissolved in acetonitrile (10 ml), and the resulting solution was added into N,N-diisopropylethylamine (0.5 ml). Then, the reaction was carried out at 25° C. for 6 hours, spin-dried and subjected to column chromatography (ethyl acetate:petroleum ether=1:2), thus obtaining 120 mg of the compound with a yield of 78.6%.

(2) Preparation of methyl 2-((1R,5S,6s)-3-(7,7-difluoro-2-(2-methylazetidin-1-yl)-6,7-dihydro-5H-cyclopenta[d]pyrimidin-4-yl)-3-azabicyclo[3.1.0]hexan-6-yl)acetate

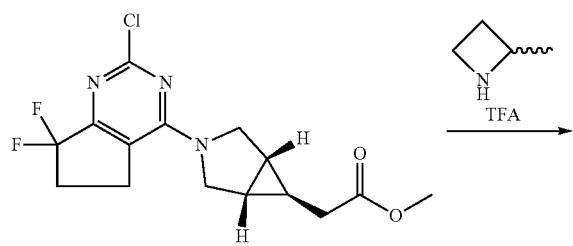

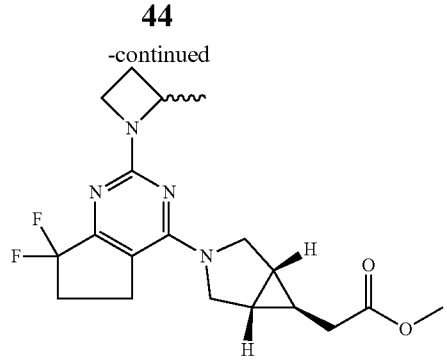

Methyl 2-((1R,5S,6s)-3-(2-chloro-7,7-difluoro-6,7-dihydro-5H-cyclopenta[d]pyrimidin-4-yl)-3-azabicyclo[3.1.0]hexan-6-yl) acetate (80 mg, 0.23 mmol) and 2-methylazetidine trifluoroacetate (100 mg, 0.54 mmol) were dissolved in acetonitrile (10 ml) and the resulting solution was added in N,N-diisopropylethylamine (0.5 ml), heated to 70° C. for 16 hours, spin-dried, and subjected to column chromatography (ethyl acetate:petroleum ether=1:2), thus obtaining 50 mg of the compound with a yield of 56.8%.

(3) Preparation of 2-((1R,5S,6s)-3-(7,7-difluoro-2-(2-methylazetidin-1-yl)-6,7-dihydro-5H-cyclopenta[d]pyrimidin-4-yl)-3-azabicyclo[3.1.0]hexan-6-yl) acetic acid

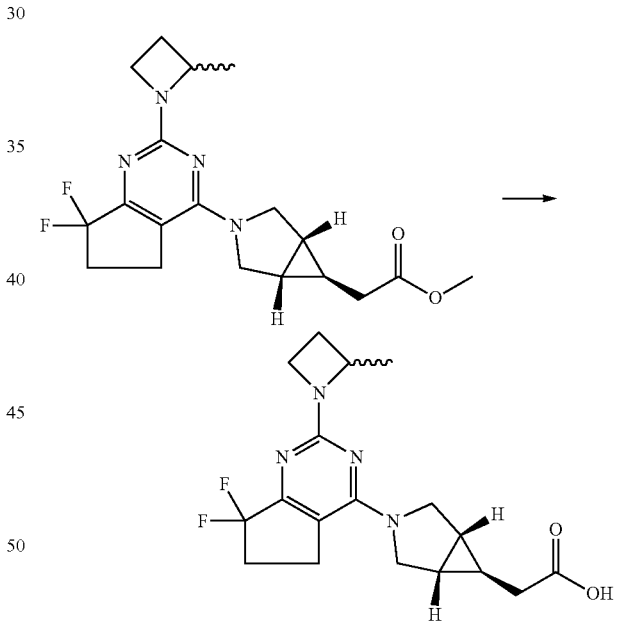

Methyl 2-((1R,5S,6s)-3-(7,7-difluoro-2-(2-methylazetidin-1-yl)-6,7-dihydro-5H-cyclopenta[d]pyrimidin-4-yl)-3-azabicyclo[3.1.0]hexan-6-yl)acetate (50 mg, 0.13 mmol) was dissolved in MeOH/H₂O (5/0.5 mL), and added with NaOH (21 mg, 0.52 mmol). The reaction was carried out at 25° C. for 3 hours, adjusted to pH4-5 with 1N hydrochloric acid, spin-dried, and subjected to preparative thin layer chromatography (dichloromethane:methanol=20:1), thus obtaining 23 mg of the compound with a yield of 47.9%.

Molecular formula: $C_{18}H_{22}F_2N_4O_2$; Molecular weight: 364.4; LC-MS (M/e): 365.2 (M+H⁺)

¹HNMR (400 MHz, CDCl₃): δ: 4.41-4.44 (m, 1H), 3.94-4.03 (m, 4H), 3.61-3.69 (m, 2H), 3.04-3.09 (m, 2H), 2.50-

2.59 (m, 3H), 2.38-2.47 (m, 2H), 1.94-2.00 (m, 1H), 1.55 (s, 2H), 1.51 (d, J=6.0 Hz, 3H), 0.90-0.99 (m, 1H).

Compound 1-2 was prepared according to the above preparation method. Related characterization data are shown as follows:

$^1$HNMR (400 MHz, DMSO): δ: 12.11 (s, br, 1H), 4.30-4.21 (m, 1H), 3.88-3.72 (m, 4H), 3.58 (s, br, 2H), 3.02-2.99 (m, 2H), 2.49-2.21 (m, 3H), 2.20-2.17 (d, J=7.2 Hz, 2H), 1.90-1.81 (m, 1H), 1.51 (s, 2H), 1.40-1.39 (d, J=6.0 Hz, 3H), 0.77-0.72 (m, 1H).

Example 2. Preparation of 2-((1R,5S,6R)-3-(8,8-difluoro-2-((S)-2-methylazetidin-1-yl)-5,6,7,8-tetrahydroquinazolin-4-yl)-3-azabicyclo[3.1.0]hexan-6-yl)acetic acid (Compound 2)

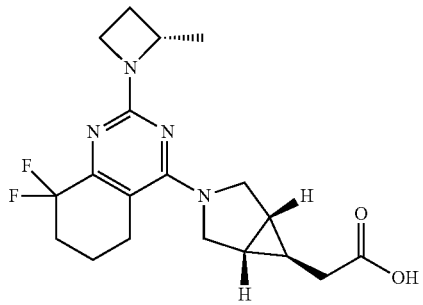 [SMILES: C[C@H]1CCN1c1nc(N2C[C@@H]3[C@@H](CC(=O)O)[C@@H]3C2)c2c(n1)C(F)(F)CCC2]

(1) Preparation of 1-ethyl 2,5-dimethyl-1-oxopentane-1,2,5-tricarboxylate

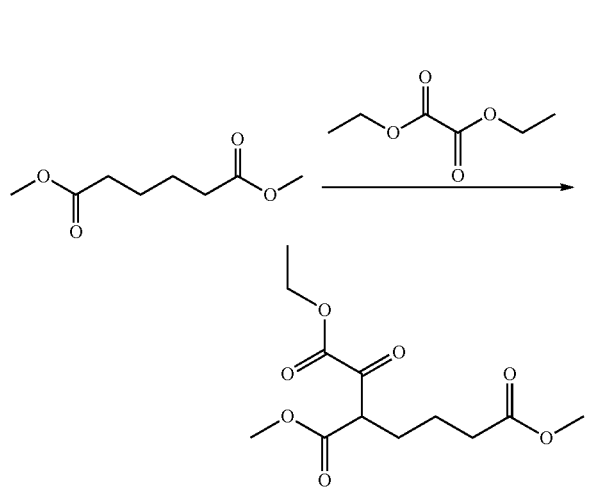

Metallic sodium (2.07 g, 90 mmol) was dissolved in anhydrous ethanol (32 mL) and stirred until clear. The solvent was concentrated to obtain EtONa as a white solid. EtONa was dissolved in THF (60 mL), and added with diethyl oxalate (13.2 g, 90 mmol) dropwise. After the addition was completed, the mixture was stirred for 30 min, and then added with dimethyl adipate (15.7 g, 90 mmol). After the addition was completed, the reaction was performed at 25° C. for 14 hours, added with water (100 mL), extracted with EA (100 mL), and layer-separated. The organic phases were washed with water (100 mL). The aqueous phases were combined, adjusted to pH 1 with concentrated HCl and were further extracted with EA (100 mL×3), and the organic phases were combined, dried and concentrated, thus obtaining 19 g of the title compound with a yield of 76.6%.

(2) Preparation of 2-oxoheptanedioic acid

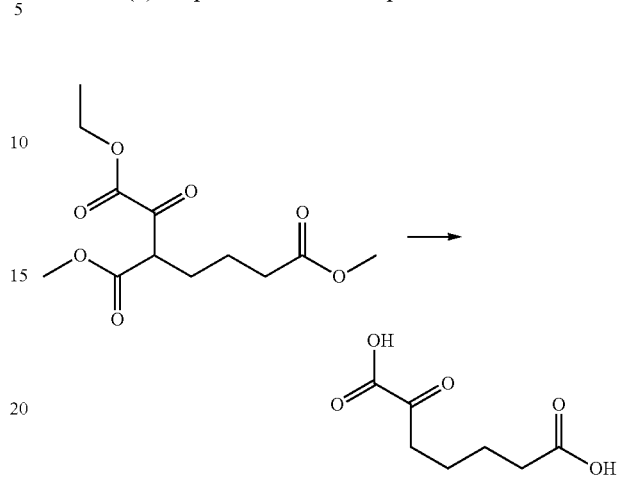

1-ethyl 2,5-dimethyl 1-oxopentane-1,2,5-tricarboxylate (14.0 g, 51.1 mmol) was dissolved in 4N HCl (75 mL). After the addition was completed, the reaction was carried out at 65° C. for 12 hours and then subjected to solvent concentration, thus obtaining 7.9 g of the title compound with a yield of 88.9%.

(3) Preparation of 7-methoxy-6,7-dioxoheptanoic acid

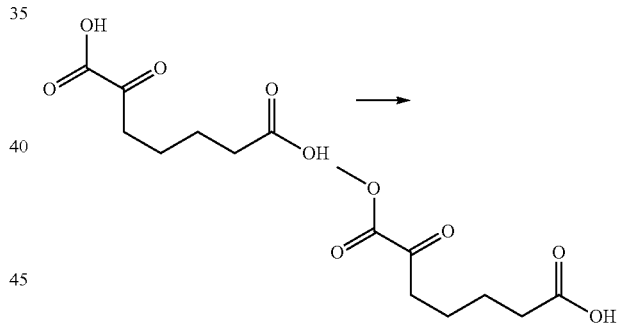

2-oxoheptanedioic acid (7.9 g, 45.4 mmol) was dissolved in acetone (100 mL), added with DBN (6.2 g, 49.9 mmol), and added with dimethyl sulfate (7.0 g, 55.4 mmol) at 0° C. After the addition is completed, the reaction was carried out at 25° C. for 12 hours, quenched with 2M hydrochloric acid, and extracted with EA. Then, the organic phases were combined, dried and concentrated, thus obtaining 9.0 g of the title compound for direct use in the next step.

(4) Preparation of dimethyl 2-oxoheptanedioate

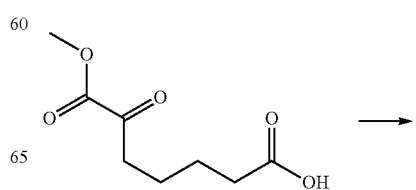

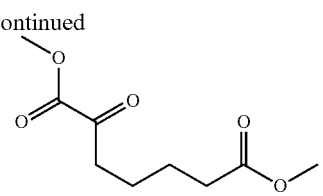

7-methoxy-6,7-dioxoheptanoic acid (9.0 g, 47.8 mmol) was dissolved in methanol (150 mL), and added with dichlorosulfane (15 mL) dropwise at 0° C. After the addition was completed, the reaction was conducted at 65° C. for 12 hours, and then subjected to solvent concentration, thus obtaining 6.6 g of the title compound with a two-step yield of 72%.

(5) Preparation of dimethyl 2,2-difluoroheptanedioate

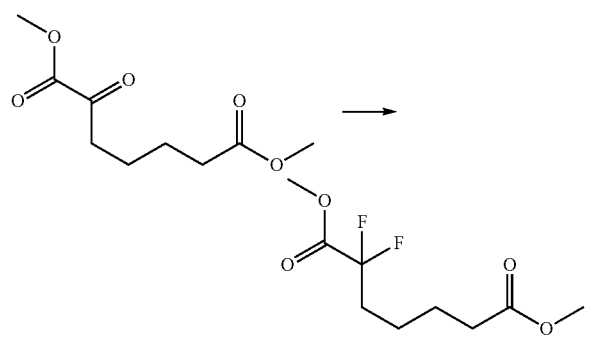

Dimethyl 2-oxoheptanedioate (1.4 g, 6.93 mmol) was dissolved in dichloromethane (25 mL), and added with DAST (5.6 g, 34.65 mmol) at 0° C. The reaction was carried at 20° C. for 16 hours, quenched by adding water, concentrated, and subjected to column chromatography (ethyl acetate:petroleum ether=1:5), thus obtaining the product (1.1 g, yield 71%).

(6) Preparation of methyl 3,3-difluoro-2-oxocyclohexane-1-carboxylate

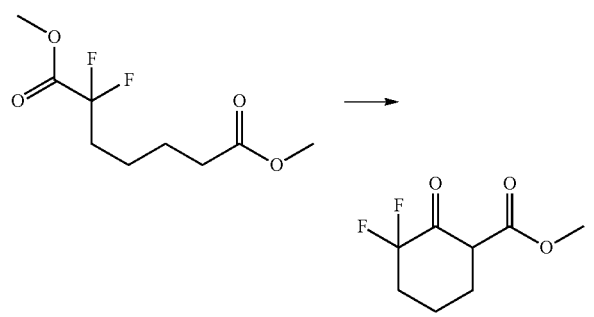

Sodium hydride (300 mg, 60%, 7.5 mmol) was dissolved in THF (20 mL), and added with dimethyl 2,2-difluoroheptanedioate (1 g, 4.46 mmol) in THF (10 mL). Then, the reaction was carried out at 20° C. for 16 hours, then quenched by adding 2 M hydrochloric acid, adjusted to pH 5, and extracted with ethyl acetate. The organic phase was washed with water, and concentrated, thus obtaining the crude product for direct use in the next step of reaction.

(7) Preparation of 8,8-difluoro-2-(methylthio)-5,6,7, 8-tetrahydroquinazolin-4-ol

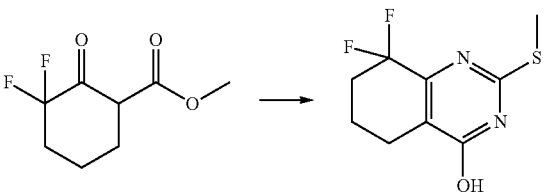

Methyl 3,3-difluoro-2-oxocyclohexane-1-carboxylate (the crude product) was dissolved in water (20 mL), and added with methyl isothiourea sulfate (1.8 g, 7.55 mmol) and sodium carbonate (945 mg, 8.92 mmol). Then, the reaction was carried out at 30° C. for 16 hours, concentrated and subjected to column chromatography (ACN/H$_2$O=0-40%), thus obtaining the crude product for the next step.

(8) Preparation of 4-chloro-8,8-difluoro-2-(methylthio)-5,6,7,8-tetrahydroquinazoline

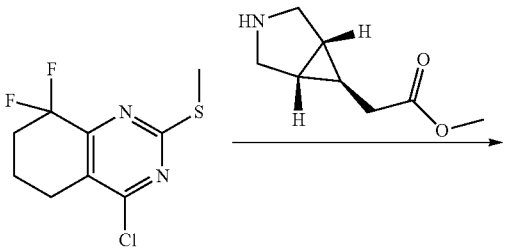

8,8-difluoro-2-(methylthio)-5,6,7,8-tetrahydroquinazolin-4-ol (the crude product) was dissolved in phosphoric trichloride (8 mL)/1,2-dichloroethane (4 mL). The reaction was carried out at 110° C. for 16 hours, concentrated, diluted with ethyl acetate, washed with saturated sodium bicarbonate followed by saturated brine, dried over anhydrous sodium sulfate, filtered and concentrated, thus obtaining the product (100 mg, a three-step yield of 9%).

(9) Preparation of methyl 2-((1R,5S,6s)-3-(8,8-difluoro-2-(methylthio)-5,6,7,8-tetrahydroquinazolin-4-yl)-3-azabicyclo[3.1.0]hexan-6-yl)acetate

49

-continued

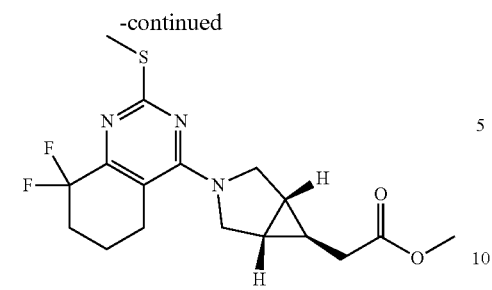

4-chloro-8,8-difluoro-2-(methylthio)-5,6,7,8-tetrahydroquinazoline (100 mg, 0.4 mmol) was dissolved in NMP (5 mL), and added with methyl 2-((1R,5S,6s)-3-azabicyclo[3.1.0]hexan-6-yl) acetate (81 mg, 0.48 mmol) and potassium carbonate (110 mg, 0.8 mmol). The reaction was carried out at 90° C. for 30 hours and then subjected to column chromatography (ACN/H$_2$O=0-70%), thus obtaining the product (90 mg, yield: 61%).

(10) Preparation of methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate

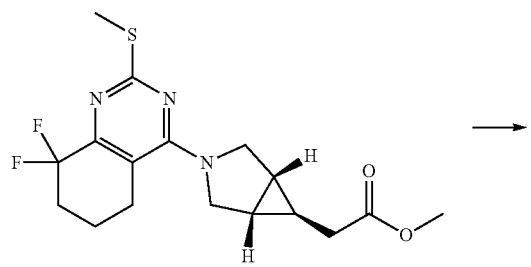

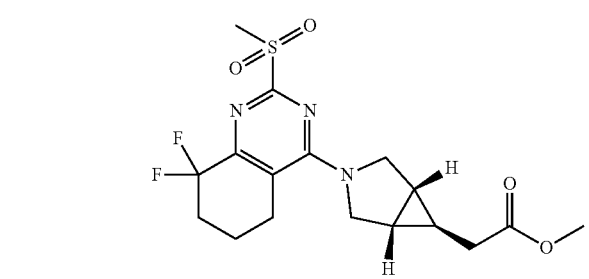

Methyl 2-((1R,5S,6s)-3-(8,8-difluoro-2-(methylthio)-5,6,7,8-tetrahydroquinazolin-4-yl)-3-azabicyclo[3.1.0]hexan-6-yl)acetate (the crude product from the previous step) was dissolved in dichloromethane (5 mL), and added with m-chloroperoxybenzoic acid (159 mg, 0.92 mmol). The reaction was carried out at 20° C. for 2 hours, quenched by adding sodium thiosulfate, washed with saturated sodium carbonate followed by saturated brine, dried over anhydrous sodium sulfate, and concentrated, thus obtaining the product (120 mg of the crude product) for direct use in the next step.

50

(11) Preparation of methyl 2-((1R,5S,6R)-3-(8,8-difluoro-2-((S)-2-methylazetidin-1-yl)-5,6,7,8-tetrahydroquinazolin-4-yl)-3-azabicyclo[3.1.0]hexan-6-yl)acetate

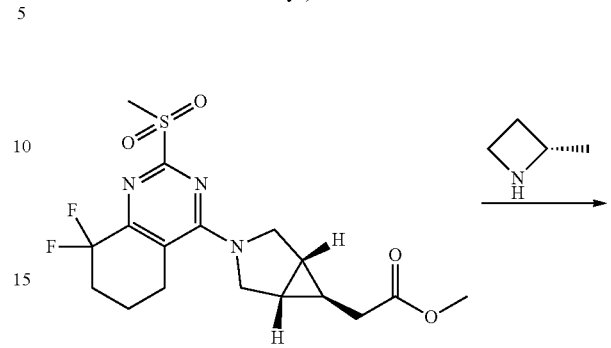

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate (80 mg the crude product) was dissolved in NMP (5 mL), then added with DIEA (125 mg, 0.97 mmol) and (S)-2-methyl azetidine (107 mg, 0.239 mmol). Then, the reaction was subject to microwave at 160° C. for 1 hour and then to column chromatography (ACN/H$_2$O=0-60%), thus obtaining 40 mg of the product.

(12) Preparation of 2-((1R,5S,6R)-3-(8,8-difluoro-2-((S)-2-methylazetidin-1-yl)-5,6,7,8-tetrahydroquinazolin-4-yl)-3-azabicyclo[3.1.0]hexan-6-yl)acetic acid

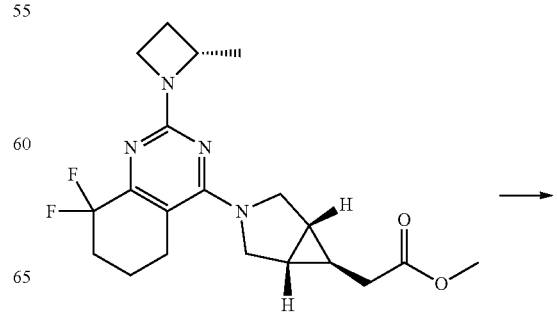

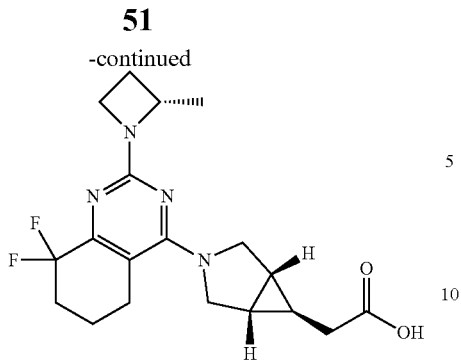

Methyl 2-((1R,5S,6R)-3-(8,8-difluoro-2-((S)-2-methyl-azetidin-1-yl)-5,6,7,8-tetrahydroquinazolin-4-yl))-3-azabicyclo[3.1.0]hexan-6-yl)acetate (30 mg, 0.076 mmol) was dissolved in THF/H$_2$O (3/3 mL), then added with NaOH (20 mg, 0.5 mmol). The reaction was carried out at 30° C. for 1 hour, adjusted pH5, concentrated, and subjected to column chromatography (ACN/H$_2$O=0-65%), thus obtaining the product (7.9 mg, yield: 27.5%). Molecular formula: C$_{19}$H$_{24}$F$_2$N$_4$O$_2$; Molecular weight: 378.4; LC-MS (M/e): 379.2 (M+H$^+$)

$^1$H-NMR (400 MHz, Methanol-D4) δ: 4.45-4.36 (m, 1H), 4.12-3.97 (m, 3H), 3.87 (q, J=8.0 Hz, 1H), 3.65-3.52 (m, 2H), 2.65-2.75 (m, 2H), 2.43-2.12 (m, 5H), 1.99-1.88 (m, 1H), 1.85-1.78 (m, 2H), 1.57-1.49 (s, 2H), 1.47 (d, J=8.0 Hz, 3H), 0.92-0.85 (m, 1H).

Example 3-1. Preparation of 2-((1R,5S,6s)-3-(8,8-difluoro-2-(3-fluoro-2-methylazetidin-1-yl)-5,6,7,8-tetrahydroquinazolin-4-yl)-3-azabicyclo[3.1.0]hexan-6-yl)acetic acid (Compound 3-1

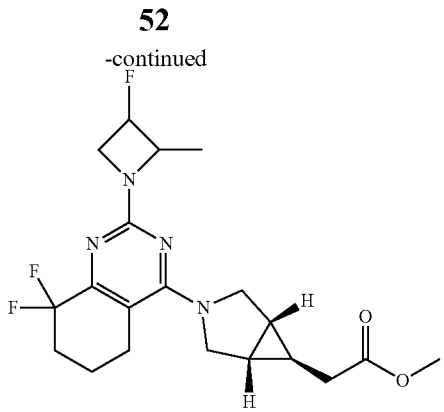

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate (50 mg, 0.12 mmol, referring to Example 2 for the preparation method) was dissolved in NMP (2 mL), and added with DIEA (77 mg, 0.6 mmol) and 3-fluoro-2-methylazacyclobutane hydrochloride (47 mg, 0.37 mmol). Then, the reaction was subjected to microwave at 160° C. for 2 hour, and then to column chromatography (ACN/H$_2$O=0-80%), thus obtaining 20 mg of the product (20 mg, yield: 41%).

(2) Preparation of 2-((1R,5S,6s)-3-(8,8-difluoro-2-(3-fluoro-2-methylazetidin-1-yl)-5,6,7,8-tetrahydroquinazolin-4-yl)-3-azabicyclo[3.1.0]hexan-6-yl)acetic acid

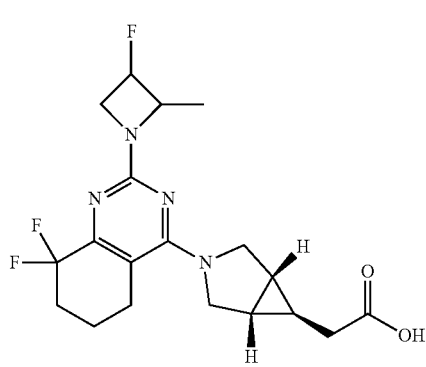 [SMILES: CC1C(F)CN1c1nc(N2C[C@@H]3[C@@H](CC(=O)O)[C@@H]3C2)c2c(n1)C(F)(F)CCC2]

(1) Preparation of methyl 2-((1R,5S,6s)-3-(8,8-difluoro-2-(3-fluoro-2-methylazetidin-1-yl)-5,6,7,8-tetrahydroquinazolin-4-yl)-3-azabicyclo[3.1.0]hexan-6-yl)acetate

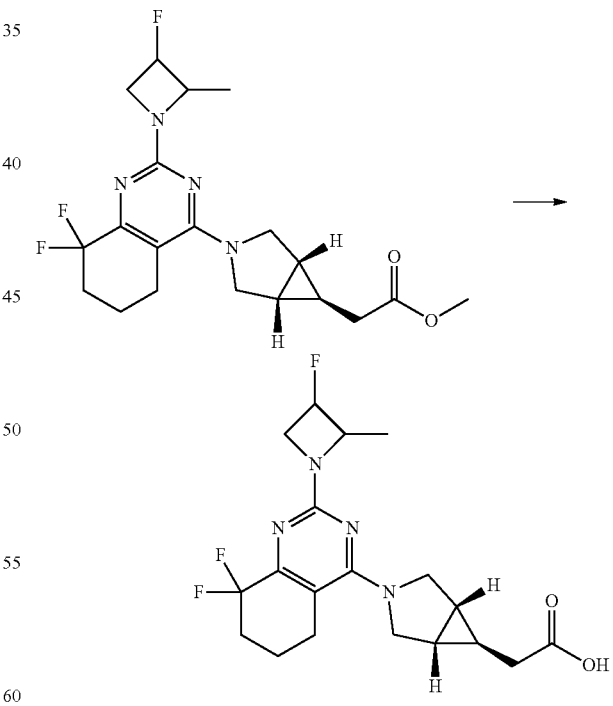

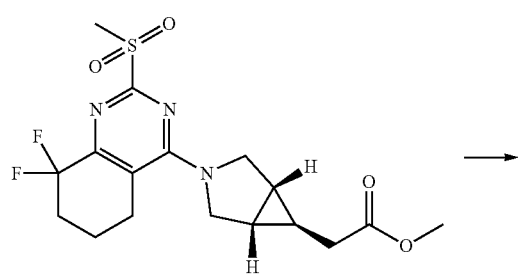

Methyl 2-((1R,5S,6s)-3-(8,8-difluoro-2-(3-fluoro-2-methylazetidin-1-yl)-5,6,7,8-tetrahydroquinazolin-4-yl))-3-azabicyclo[3.1.0]hexan-6-yl)acetate (20 mg, 0.048 mmol) was dissolved in THF/H$_2$O (2/2 mL), and added with NaOH (4 mg, 0.097 mmol). The reaction was carried out at 20° C. for 3 hours, adjusted to pH5, concentrated, and subjected to preparative thin layer chromatography (ACN/H₂O=1-65%), thus obtaining the product (9 mg, yield: 47%).

Molecular formula: $C_{19}H_{23}F_3N_4O_2$; Molecular weight: 396.4; LC-MS (M/e): 379.2 (M+H⁺)

¹H-NMR (400 MHz, CDCl₃) δ: 5.05-4.86 (m, 1H), 4.55-4.30 (m, 3H), 4.15-3.95 (m, 3H), 3.72-3.57 (m, 2H), 2.70 (s, 1H), 2.38 (m, 2H), 2.35-2.15 (m, 2H), 1.95-1.81 (m, 2H), 1.62-1.48 (m, 5H), 1.09-0.98 (m, 2H).

Example 4-1. Preparation of 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl)acetic acid (Compound 4-1

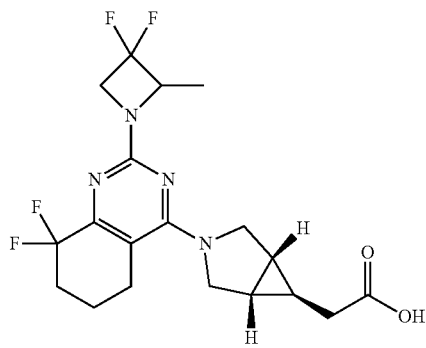 [SMILES: CC1N(c2nc(N3C[C@@H]4[C@@H](CC(=O)O)[C@@H]4C3)c3c(n2)C(F)(F)CCC3)CC1(F)F]

(1) Preparation of methyl 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl)acetate

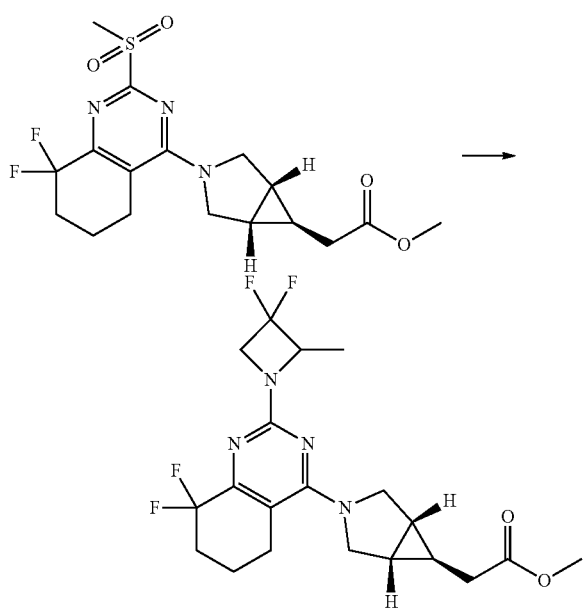

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate (100 mg, 0.25 mmol, referring to Example 2 for the preparation method) was dissolved in NMP (2 mL), and then added with DIEA (97 mg, 0.75 mmol) and 3,3-difluoro-2-methylazacyclobutane hydrochloride (72 mg, 0.5 mmol). Then, the reaction was subjected to microwave at 160° C. for 2 hours. After that, the reaction was additionally added with 3,3-difluoro-2-methylazacyclobutane hydrochloride (72 mg, 0.5 mmol), and then further subjected to microwave at 160° C. for 2 hours. Then, the reaction was subjected to column chromatography (ACN/H₂O=0-85%), thus obtaining the product (50 mg, yield: 47%).

(2) Preparation of 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl) acetic acid

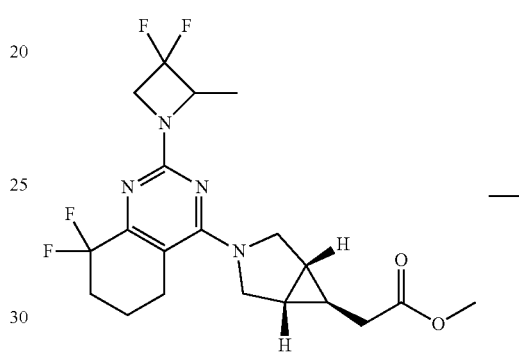

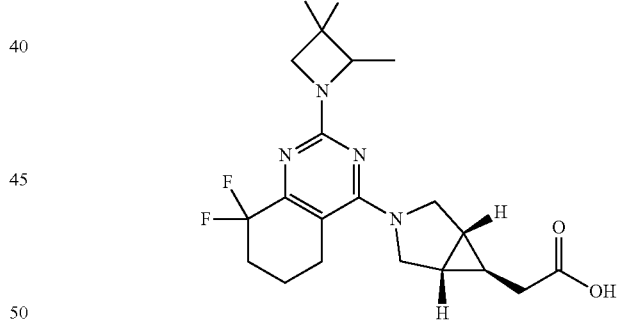

Methyl 2-((1R,5S,6s)-3-(2-(3,3-difluoro-2-methylazetidin-1-yl)-8,8-difluoro-5,6,7,8-tetrahydroquinazolin-4-yl))-3-azabicyclo[3.1.0]hexan-6-yl)acetate (50 mg, 0.117 mmol) was dissolved in THF/H₂O (3/3 mL), and then added with NaOH (9 mg, 0.234 mmol). The reaction was carried out at 20° C. for 3 hours, adjusted to pH 5, concentrated, and then subjected to preparative thin layer chromatography (MeOH/CH₂Cl₂=1/20) to obtain the product (24 mg, yield: 50%).

Molecular formula: $C_{19}H_{22}F_4N_4O_2$; Molecular weight: 414.4; LC-MS (M/e): 415.2 (M+H⁺)

¹H-NMR (400 MHz, CDCl₃) δ: 4.70-4.55 (m, 1H), 4.34 (t, J=12 Hz, 2H), 4.12-4.02 (m, 2H), 3.69-3.57 (m, 2H), 2.75-2.65 (m, 2H), 2.46-2.18 (m, 4H), 1.95-1.82 (m, 2H), 1.52 (m, 3H), 1.40-1.25 (m, 2H), 1.09-0.98 (m, 1H).

Example 4-2: Preparation of a Single Configuration isomer of 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl)acetic acid (1) Preparation of methyl 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl)acetate

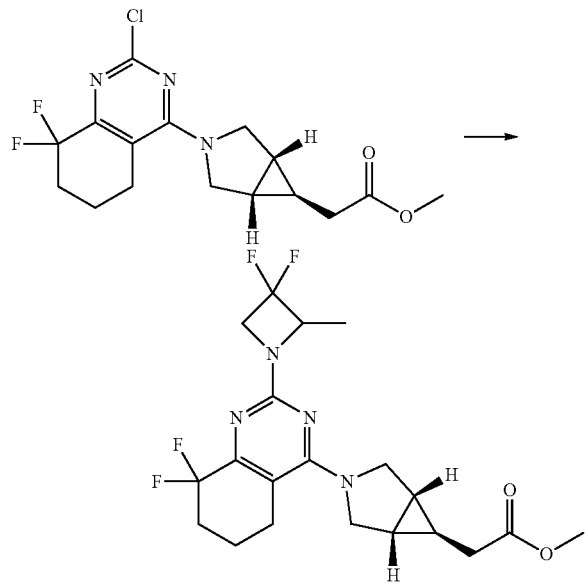

Methyl 2-((1R,5S,6s)-3-(2-chloro-8,8-difluoro-5,6,7,8-tetrahydroquinazolin-4-yl)-3-azabicyclo[3.1.0]hexan-6-yl)acetate (300 mg, 0.84 mmol) was dissolved in ACN (10 mL), and then added with DIEA (542 mg, 4.2 mmol) and 2-methyl 3,3-difluoroazacyclobutane hydrochloride (150 mg, 1.04 mmol). Then, the reaction was carried out at 80° C. for 16 hours, and then subjected to column chromatography (EA/PE=30%), thus obtaining the product (150 mg, yield: 42%).

(2) Preparation of a Single Configuration isomer of 2-((1R,5S,6s)-3-(2-(3,3-difluoro-2-methylazetidin-1-yl)-8,8-difluoro-5,6,7,8-tetrahydroquinazolin-4-yl)-3-azabicyclo[3.1.0]hexan-6-yl) acetic acid

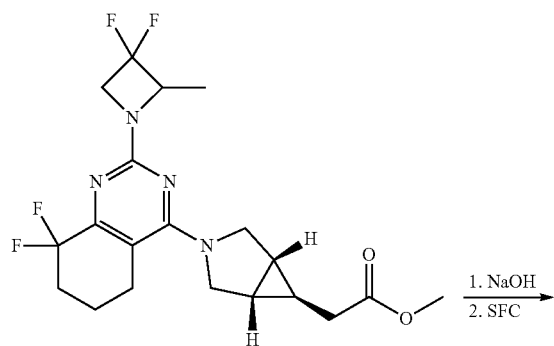

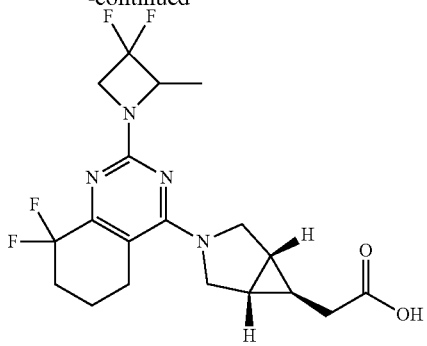

Compound 4-2 (retention time: 20.987)

Compound 4-3 (retention time: 19.762)

Methyl 2-((1R,5S,6s)-3-(2-(3,3-difluoro-2-methylazetidin-1-yl)-8,8-difluoro-5,6,7,8-tetrahydroquinazolin-4-yl))-3-azabicyclo[3.1.0]hexan-6-yl)acetate (150 mg, 0.35 mmol) was dissolved in THF/H$_2$O (8/8 mL), and then added with NaOH (28 mg, 0.7 mmol). The reaction was carried out at 20° C. for 16 hours, adjusted to pH5, concentrated, and subjected to column chromatography (ACN/H$_2$O=0-70%), thus obtaining the product (100 mg, yield: 69%), which was further subjected to a chiral column IG-3 (IG30CD-WE016), thus obtaining compound 4-2 (retention time: 20.987) and compound 4-3 (retention time: 19.762).

Among them, one of compound 4-2 and compound 4-3 is compound 4, and the structure of the other single configuration isomer is:

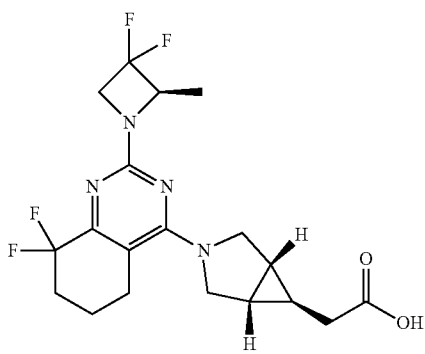 [SMILES: C[C@H]1N(c2nc(N3C[C@@H]4[C@@H](CC(=O)O)[C@@H]4C3)c3c(n2)C(F)(F)CCC3)CC1(F)F]

Molecular formula: C$_{19}$H$_{22}$F$_4$N$_4$O$_2$; Molecular weight: 414.4; LC-MS (M/e): 415.2 (M+H$^+$)

Compound 4-2: $^1$H-NMR (400 MHz, CDCl$_3$) δ: 4.70-4.55 (m, 1H), 4.34 (t, J=12 Hz, 2H), 4.12-4.02 (m, 2H), 3.69-3.57 (m, 2H), 2.75-2.65 (m, 2H), 2.46-2.18 (m, 4H), 1.95-1.82 (m, 2H), 1.52 (m, 3H), 1.40-1.25 (m, 2H), 1.09-0.98 (m, 1H).

Compound 4-3: $^1$H-NMR (400 MHz, CDCl$_3$) δ: 4.70-4.55 (m, 1H), 4.34 (t, J=12 Hz, 2H), 4.12-4.02 (m, 2H), 3.69-3.57 (m, 2H), 2.75-2.65 (m, 2H), 2.46-2.18 (m, 4H), 1.95-1.82 (m, 2H), 1.52 (m, 3H), 1.40-1.25 (m, 2H), 1.09-0.98 (m, 1H).

Example 5-1. Preparation of 2-((1R,5S,6s)-3-(2-(3,3-difluoro-2-methylazetidin-1-yl)-7,7-difluoro-6,7-dihydro-5H-cyclopenta[d]pyrimidin-4-yl)-3-azabicyclo[3.1.0]hexan-6-yl)acetic acid (Compound 5-1

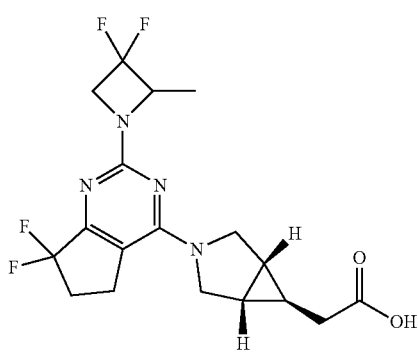 [SMILES: CC1N(c2nc(N3C[C@@H]4[C@@H](CC(=O)O)[C@@H]4C3)c3c(n2)C(F)(F)CC3)CC1(F)F]

(1) Preparation of methyl 2-((1R,5S,6s)-3-(2-(3,3-difluoro-2-methylazetidin-1-yl)-7,7-difluoro-6,7-dihydro-5H-cyclopenta[d]pyrimidin-4-yl)-3-azabicyclo[3.1.0]hexan-6-yl)acetate

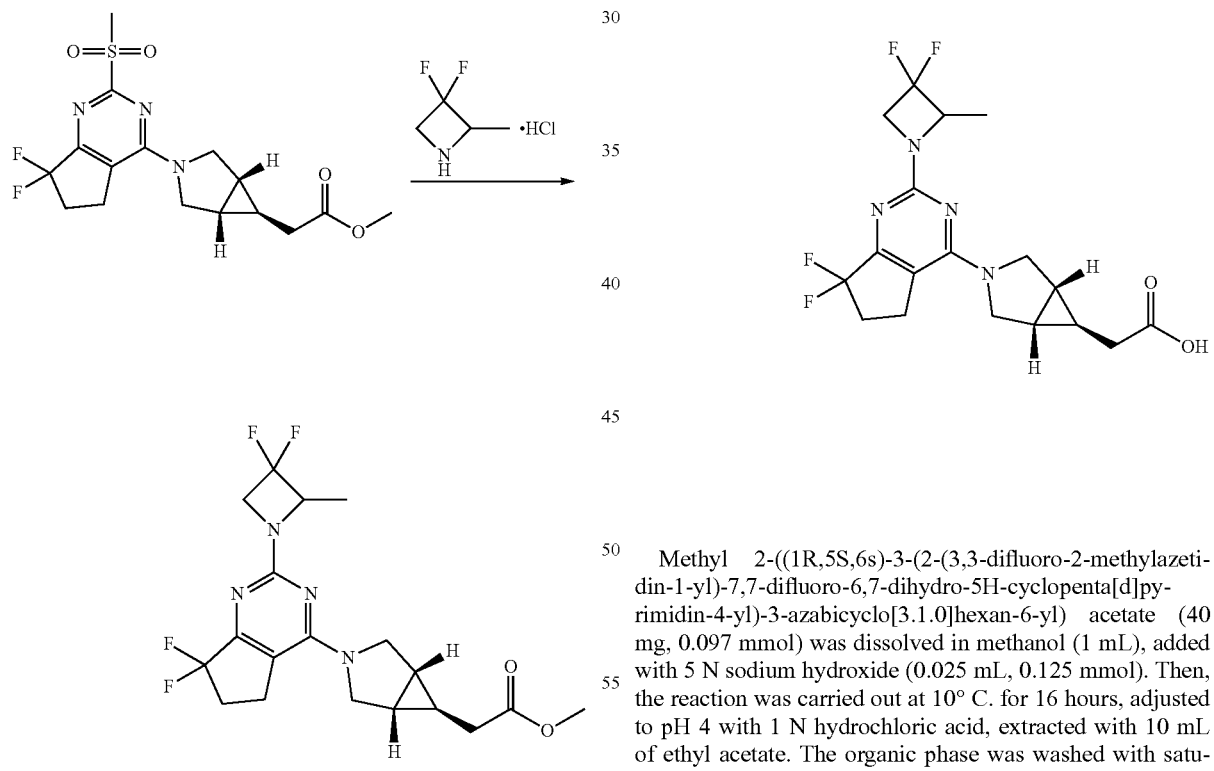

Methyl 2-((1R,5S,6s)-3-(7,7-difluoro-2-(methylsulfonyl)-6,7-dihydro-5H-cyclopenta(d)pyrimidine-4-yl)-3-azabicyclo[3.1.0]hexan-6-yl)acetate (70 mg, 0.18 mmol, referring to Example 1 for the preparation method) was dissolved in N-methylpyrrolidone (2 mL), and then added with diisopropylaminoethylamine (93.1 mg, 0.72 mmol) and 3,3-difluoro-2-methylazetidine hydrochloride (57.4 mg, 0.40 mmol). Then, the reaction was subjected to microwave at 150° C. for 2 hours, diluted with ethyl acetate, washed with saturated brine. Then, the organic phase was dried over anhydrous sodium sulfate, spin-dried, and subjected to column chromatography (30% ethyl acetate/petroleum ether), thus obtaining the product (40 mg, yield 53%).

(2) Preparation of 2-((1R,5S,6s)-3-(2-(3,3-difluoro-2-methylazetidin-1-yl)-7,7-difluoro-6,7-dihydro-5H-cyclopenta[d]pyrimidin-4-yl)-3-azabicyclo[3.1.0]hexan-6-yl)acetic acid

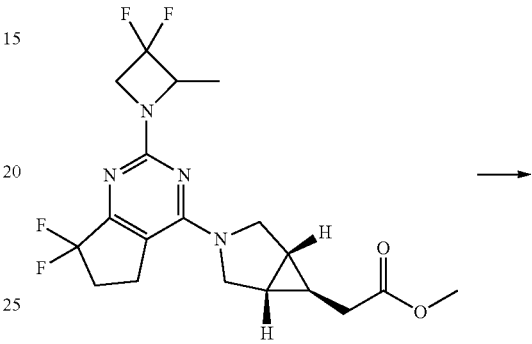

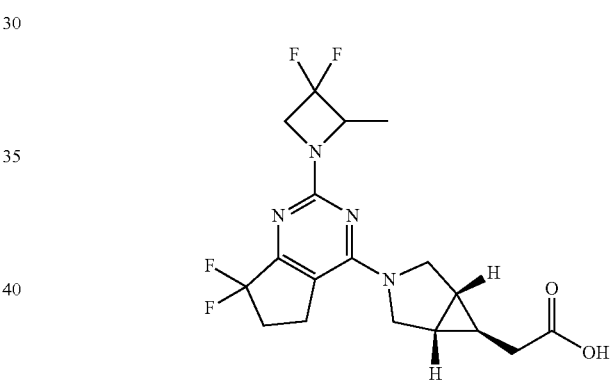

Methyl 2-((1R,5S,6s)-3-(2-(3,3-difluoro-2-methylazetidin-1-yl)-7,7-difluoro-6,7-dihydro-5H-cyclopenta[d]pyrimidin-4-yl)-3-azabicyclo[3.1.0]hexan-6-yl) acetate (40 mg, 0.097 mmol) was dissolved in methanol (1 mL), added with 5 N sodium hydroxide (0.025 mL, 0.125 mmol). Then, the reaction was carried out at 10° C. for 16 hours, adjusted to pH 4 with 1 N hydrochloric acid, extracted with 10 mL of ethyl acetate. The organic phase was washed with saturated brine, spin-dried, and subjected to column chromatography (5% methanol/dichloromethane), thus obtaining the product (6.5 mg, yield 17%).

Molecular formula: $C_{18}H_{20}F_4N_4O_2$; Molecular weight: 400.4; LC-MS (M/e): 401.2 (M+H$^+$)

$^1$H-NMR (400 MHz, CDCl$_3$) δ: 4.68-4.62 (m, 1H), 4.38 (t, J=12.0, 2H), 4.06 (t, J=12.0, 2H), 3.73-3.66 (m, 2H), 3.10-3.07 (m, 2H), 2.52-2.40 (m, 4H), 1.61-1.33 (m, 5H), 1.03-1.00 (m, 1H).

Example 6-1. Preparation of 2-((1R,5S,6s)-3-(7,7-difluoro-2-(3-fluoro-2-methylazetidin-1-yl)-6,7-dihydro-5H-cyclopenta[d]pyrimidin-4-yl)-3-azabicyclo[3.1.0]hexan-6-yl)acetic acid (Compound 6-1

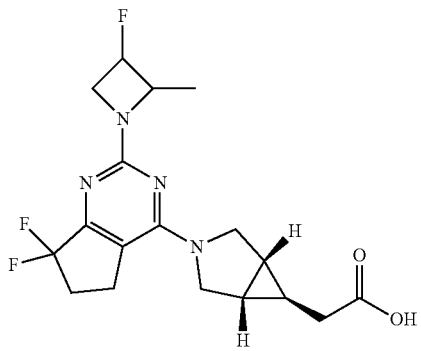 [SMILES: CC1C(F)CN1c1nc(N2C[C@@H]3[C@@H](CC(=O)O)[C@@H]3C2)c2c(n1)C(F)(F)CC2]

(1) Preparation of methyl 2-((1R,5S,6s)-3-(7,7-difluoro-2-(3-fluoro-2-methylazetidin-1-yl)-6,7-dihydro-5H-cyclopenta[d]pyrimidin-4-yl)-3-azabicyclo[3.1.0]hexan-6-yl)acetate

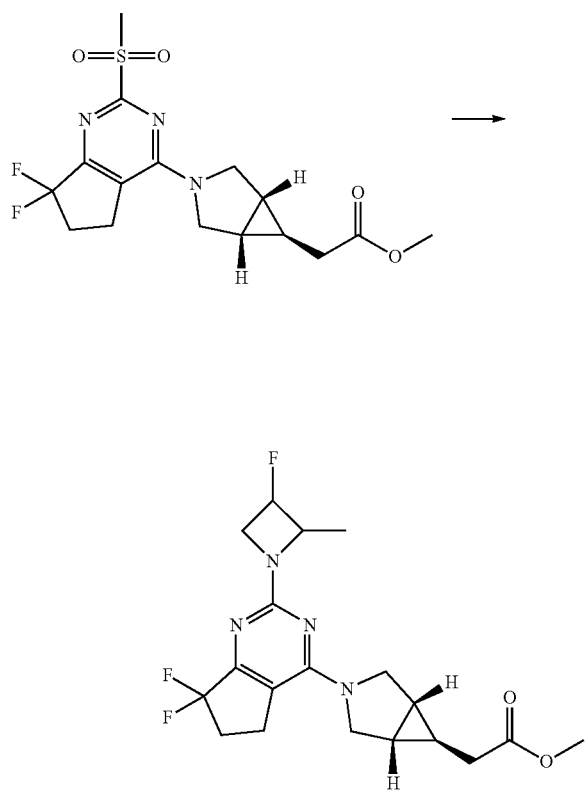

Methyl 2-((1R,5S,6s)-3-(7,7-difluoro-2-(methylsulfonyl)-6,7-dihydro-5H-cyclopenta[d]pyrimidine-4-yl)-3-azabicyclo[3.1.0]hexan-6-yl)acetate (50 mg, 0.13 mmol, referring to Example 1 for the preparation method) was dissolved in N-methylpyrrolidone (2 mL), and added with diisopropylaminoethylamine (50.4 mg, 0.39 mmol) and 3-fluoro-2-methylazetidine hydrochloride (19.5 mg, 0.15 mmol). Then, the reaction was subjected to microwave at 150° C. for 2 hours, diluted with ethyl acetate. The organic phase was washed with saturated brine, dried over anhydrous sodium sulfate, spin-dried, and subjected to column chromatography (30% ethyl acetate/petroleum ether), thus obtaining the product (30 mg, yield 59%).

(2) Preparation of 2-((1R,5S,6s)-3-(7,7-difluoro-2-(3-fluoro-2-methylazetidin-1-yl)-6,7-dihydro-5H-cyclopenta[d]pyrimidin-4-yl)-3-azabicyclo[3.1.0]hexan-6-yl)acetic acid

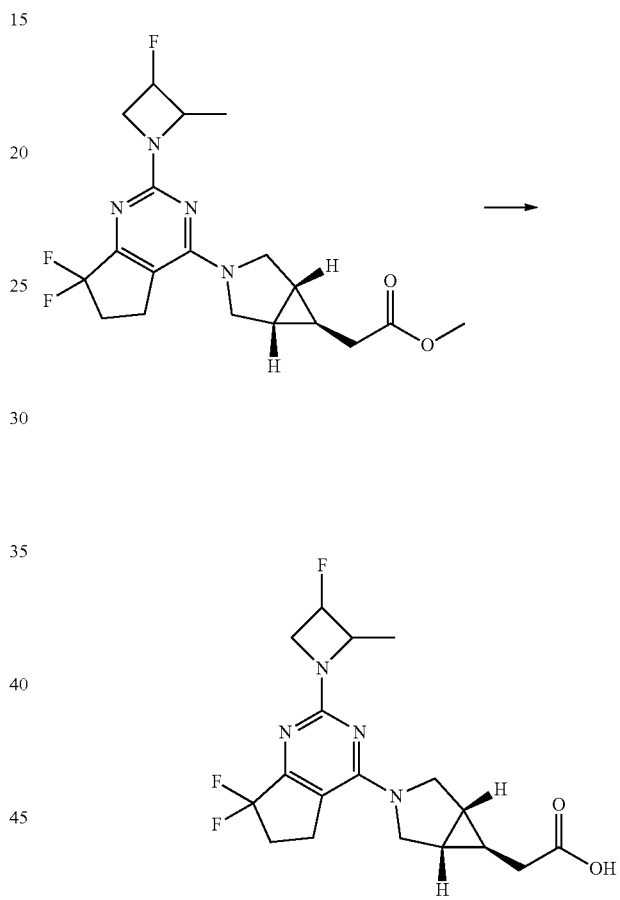

Methyl 2-((1R,5S,6s)-3-(7,7-difluoro-2-(3-fluoro-2-methylazetidin-1-yl)-6,7-dihydro-5H-cyclopenta[d]pyrimidin-4-yl)-3-azabicyclo[3.1.0]hex-6-yl) acetate (30 mg, 0.076 mmol) was dissolved in methanol (1 mL) and water (0.3 mL), and added with sodium hydroxide (3.94 mg, 0.098 mmol). The reaction was carried out at 10° C. for 16 hours, adjusted to pH4 with 1 N hydrochloric acid, extracted with 10 mL of ethyl acetate. The organic phase was washed with saturated brine, spin-dried, and subjected to column chromatography (5% methanol/dichloromethane), thus obtaining the product (14 mg, yield 48%).

Molecular formula: $C_{18}H_{21}F_3N_4O_2$; Molecular weight: 382.4; LC-MS (M/e): 383.2 (M+H$^+$)

$^1$H-NMR (400 MHz, CDCl$_3$) δ: 5.32-5.30 (m, 0.5H), 4.99-4.97 (m, 0.5H), 4.46-4.29 (m, 2H), 4.08-3.97 (m, 3H), 3.69-3.62 (m, 2H), 3.07-3.01 (m, 2H), 2.52-2.37 (m, 5H), 1.57-1.53 (m, 5H), 1.02-0.59 (m, 1H).

Example 7. Preparation of 2-((1R,5S,6R)-3-(9,9-difluoro-2-((S)-2-methylazetidin-1-yl)-6,7,8,9-tetrahydro-5H-cyclopenta[d]pyrimidin-4-yl)-3-azabicyclo[3.1.0]hexan-6-yl)acetic acid (Compound 7)

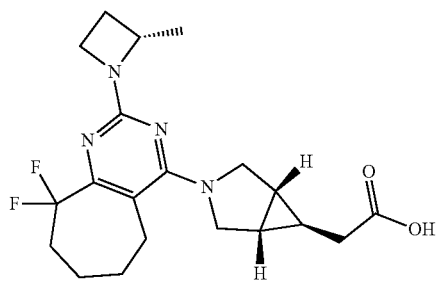 [SMILES: C[C@H]1CCN1c1nc(N2C[C@@H]3[C@@H](CC(=O)O)[C@@H]3C2)c2c(n1)C(F)(F)CCCC2]

(1) Preparation of 1-ethyl 2,6-dimethyl 1-oxohexane-1,2,6-tricarboxylate

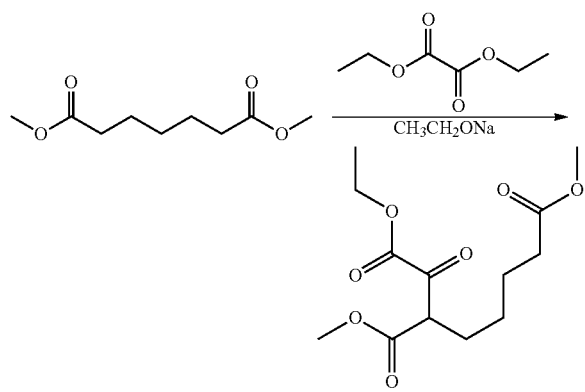

Sodium ethoxide (2.0 g, 29.3 mmol) was dissolved in THF (20 mL), added with diethyl oxalate (3.9 g, 26.6 mmol) and dimethyl pimelate (5.0 g, 26.6 mmol). The reaction was carried out at 25° C. for 16 hours. After being completed, the reaction was distilled under reduced pressure, and layer-separated by adding water and EA. The aqueous phase was adjusted to pH=1, extracted with EA. Then, the obtained organic phase was distilled under reduced pressure, thus obtaining the product for direct use in the next step of reaction.

(2) Preparation of 2-oxosuberic acid

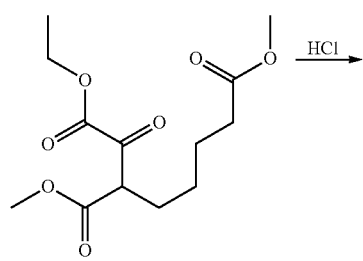

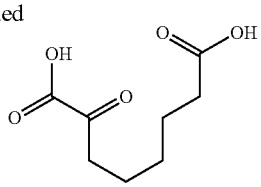

1-ethyl 2,6-dimethyl 1-oxohexane-1,2,6-tricarboxylate (the crude product 7.7 g) was dissolved in 4M HCl (66 ml). After the addition was completed, the reaction was conducted at 65° C. for 10 hours. After being completed, the reaction was directly spin-dried, thus obtaining the product for direct use in the next step of reaction.

(3) Preparation of 8-methoxy-7,8-dioxooctanoic acid

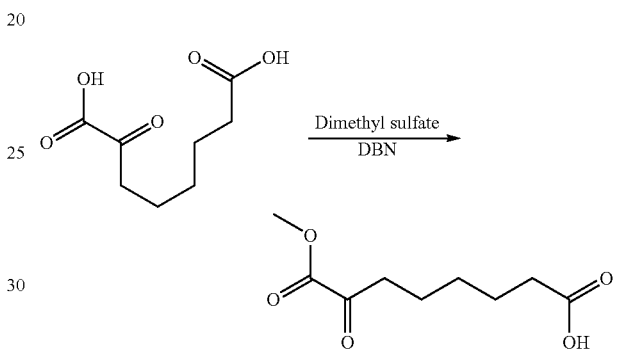

DBN (4.0 g, 31.9 mmol) was dissolved in acetone (60 mL), added with 2-oxosuberic acid (crude 5.0 g) and dimethyl sulfate (3.4 g, 26.6 mmol). Then, the reaction was conducted at 25° C. for 16 hours. After being completed, the reaction was directly spin-dried, and added with EA. Then, the organic phase was washed with 1N HCl, and distilled under reduced pressure, thus obtaining the product for direct use in the next step of reaction.

(4) Preparation of dimethyl 2-oxosuberate

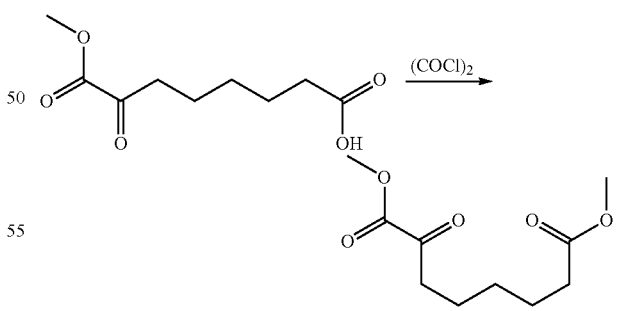

8-methoxy-7,8-dioxooctanoic acid (the crude product 5.4 g) was dissolved in DCM (40 ml), and then added with (COCl)$_2$ (5.1 g, 40.0 mmol). The reaction was carried out at 25° C. for 6 hours, added with MeOH (20 ml), and then further carried out for additional 16 hours. After being completed, the reaction was directly distilled under reduced pressure, thus obtaining the product for direct use in the next step of reaction.

(5) Preparation of dimethyl 2,2-difluorosuberate

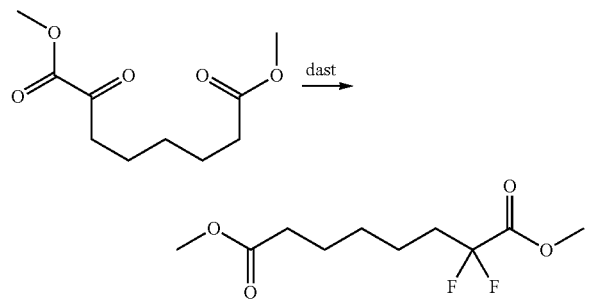

Dimethyl 2-octanedioate (the crude product 5.7 g) was dissolved in DCM (50 ml), and added with dast (10.0 ml, 79.8 mmol). After the addition was completed, the reaction was conducted at 25° C. for 48 hours. The reaction, after completed, was added with 50 ml of water, extracted with EA, and was subjected to normal phase column chromatography (EA:PE=1:8), thus obtaining 1.9 g of the product with a five-step yield of 30%.

(6) Preparation of methyl 3,3-difluoro-2-oxocycloheptane-1-carboxylate

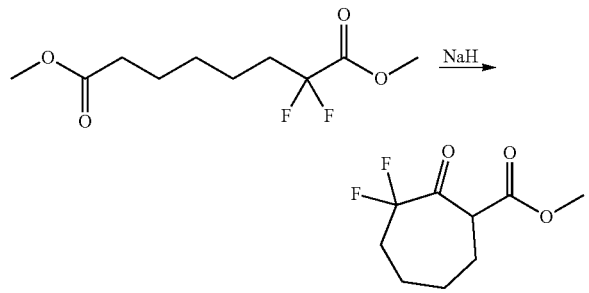

60% NaH (480.0 mg, 12.0 mmol) was dissolved in THF, and added with dimethyl 2,2-difluorosuberate (1.9 g, 8.0 mmol). Then, the reaction was conducted at 50° C. for 16 hours. The reaction, after completed, was cooled to 20° C., quenched by adding water, and subjected to column chromatography (EA:PE=1:10), thus obtaining 680 mg of the product with a yield of 41%.

(7) Preparation of 9,9-difluoro-2-(methylthio)-6,7,8,9-tetrahydro-5H-cyclohepta[d]pyrimidin-4-ol

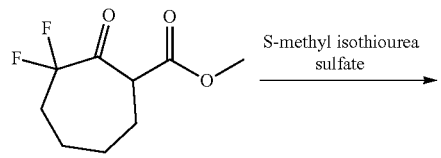

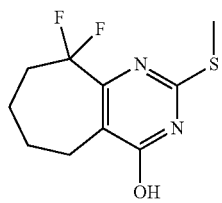

Methyl 3,3-difluoro-2-oxocycloheptane-1-carboxylate (1.0 g, 4.8 mmol) was dissolved in water (30 ml) and added with S-methyl isothiourea sulfate (1.0 g, 7.2 mmol) and Na$_2$CO$_3$ (1.0 g, 9.6 mmol). After the addition was completed, the reaction was conducted at 25° C. for 16 hours. The reaction, after completed, was adjusted to pH=5 and subjected to work-up, thus obtaining the product for direct use in the next step of reaction.

(8) Preparation of 4-chloro-9,9-difluoro-2-(methylthio)-6,7,8,9-tetrahydro-5H-cyclohepta[d]pyrimidine

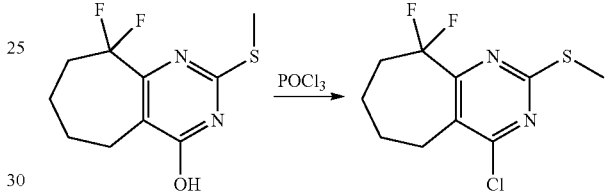

9,9-difluoro-2-(methylthio)-6,7,8,9-tetrahydro-5H-cyclohepta[d]pyrimidin-4-ol (the crude product 3.5 g) was dissolved in DCE (10 ml) and POCl$_3$ (20 ml). Then the reaction was carried out at 110° C. for 16 hours. The reaction, after completed, was evaporated under reduced pressure, adjusted to pH 8 by adding saturated NaHCO$_3$, extracted with EA, and then subjected to column chromatography (EA:PE=1:5), thus obtaining 650 mg of the product with a two-step yield of 51%.

(9) Preparation of methyl 2-((1R,5S,6s)-3-(9,9-difluoro-2-(methylthio)-6,7,8,9-tetrahydro-5H-cyclohepta[d]pyrimidine-4-yl)-3-azabicyclo[3.1.0]hexan-6-yl) acetate

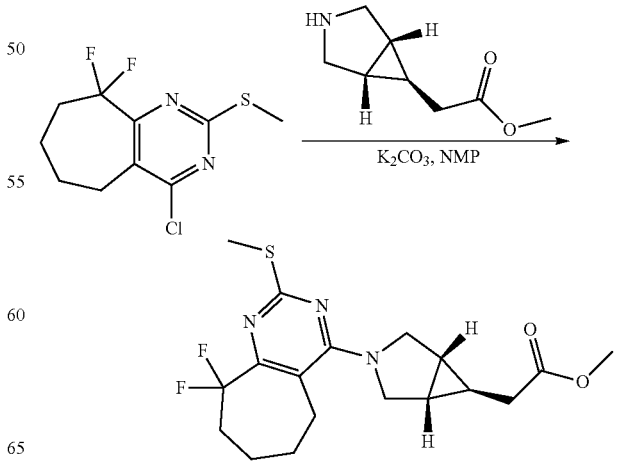

4-chloro-9,9-difluoro-2-(methylthio)-6,7,8,9-tetrahydro-5H-cyclohepta[d]pyrimidine (300.0 mg, 1.14 mmol) was dissolved in NMP (10 ml), added with methyl 2-((1R,5S,6s)-3-azabicyclo[3.1.0]hexane-6-yl)acetate (264.0 mg, 1.7 mmol) and K₂CO₃ (315.0 mg, 2.3 mmol). Then the reaction was conducted at 90° C. for 3 hours. The reaction, after completed, was quenched with water, extracted with EA, and then subjected to column chromatography (EA:PE=1:5), thus obtaining 350 mg of the product with a yield of 83%.

(10) Preparation of methyl 2-((1R,5S,6s)-3-(9,9-difluoro-2-(methylsulfonyl)-6,7,8,9-tetrahydro-5H-cyclohepta[d]pyrimidin-4-yl)-3-azabicyclo[3.1.0]hexan-6-yl)acetate

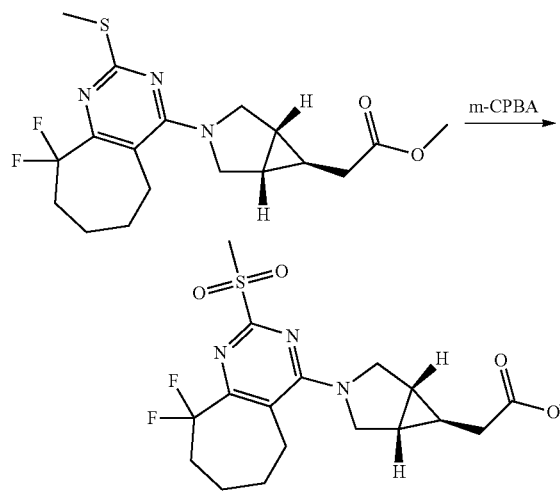

Methyl 2-((1R,5S,6s)-3-(9,9-difluoro-2-(methylthio)-6,7,8,9-tetrahydro-5H-cyclohepta[d]pyrimidine-4-yl)-3-azabicyclo[3.1.0]hexan-6-yl)acetate (350.0 mg, 0.9 mmol) was dissolved in DCM (90 ml), and added with m-CPBA (80%) (392.0 mg, 1.8 mmol). Then, the reaction was conducted at 25° C. for 3 hours. The reaction, after completed, was quenched with saturated NaHCO₃, extracted with DCM, and subjected to column chromatography (EA:PE=2:1), thus obtaining 250 mg of the product with a yield of 67%.

(11) Preparation of methyl 2-((1R,5S,6R)-3-(9,9-difluoro-2-((S)-2-methylazetidine-1-yl)-6,7,8,9-tetrahydro-5H-cycloheptano[d]pyrimidin-4-yl)-3-azabicyclo[3.1.0]hexan-6-yl) acetate

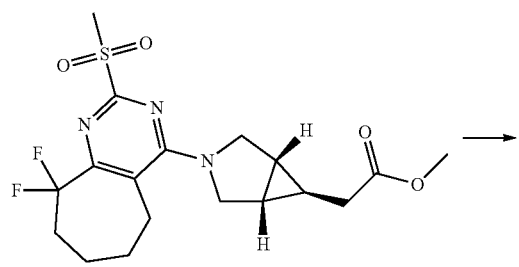

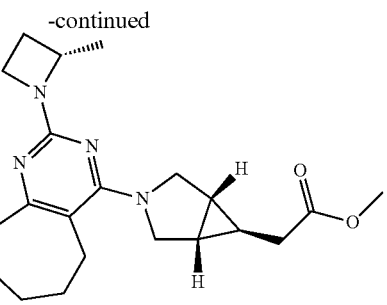

Methyl 2-((1R,5S,6s)-3-(9,9-difluoro-2-(methylsulfonyl)-6,7,8,9-tetrahydro-5H-cyclohepta[d]pyrimidine-4-yl)-3-azabicyclo[3.1.0]hexan-6-yl) acetate (250.0 mg, 0.6 mmol) was dissolved in NMP (6 ml), added with (S)-2-methyl azetidine (0.5 ml, 3.0 mmol). Then, the reaction was subjected to microwave at 160° C. for 8 hours. After completed, the reaction was added with water, extracted with EA, and subjected to column chromatography (EA:PE=1:3), thus obtaining 120 mg of the product with a yield of 49%.

(12) Preparation of 2-((1R,5S,6R)-3-(9,9-difluoro-2-((S)-2-methylazetidine-1-yl)-6,7,8,9-tetrahydro-5H-cycloheptano[d]pyrimidin-4-yl)-3-azabicyclo[3.1.0]hexan-6-yl) acetic acid

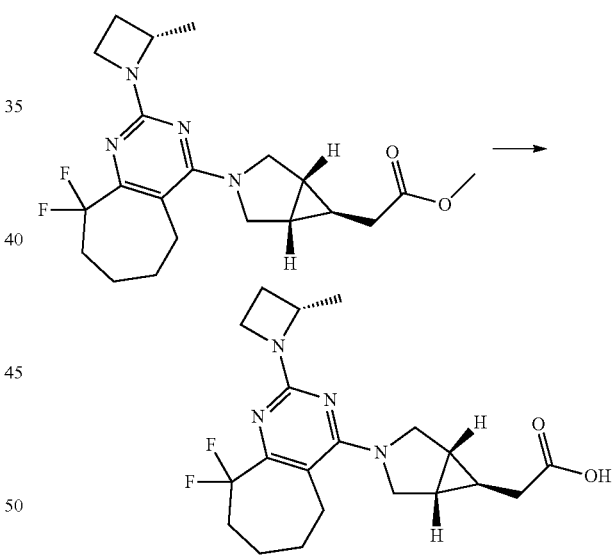

Methyl 2-((1R,5S,6R)-3-(9,9-difluoro-2-((S)-2-methylazetidine-1-yl)-6,7,8,9-tetrahydro-5H-cycloheptano[d]pyrimidin-4-yl)-3-azabicyclo[3.1.0]hexan-6-yl) acetate (120.0 mg, 0.3 mmol) was dissolved in THF (3 mL) and H₂O (3 mL), and added with NaOH (17.7 mg, 0.4 mmol). The reaction was carried out at 25° C. for 3 hours. After completed, the reaction was adjusted to a weak acidic pH and then subjected to preparative thin layer chromatography (DCM:MeOH=15:1), thus obtaining the product of 60 mg with a yield of 53%.

Molecular formula: $C_{20}H_{26}F_2N_4O_2$; Molecular weight: 392.45; LC-MS (M/e): 393.0 (M+H⁺)

¹H-NMR (400 MHz, MeOD) δ: 4.47-4.40 (m, 1H), 4.05-3.87 (m, 4H), 3.49 (t, J=11.2 Hz, 2H), 2.68-2.66 (m, 2H), 2.43-2.35 (m, 1H), 2.35-2.16 (m, 4H), 2.00-1.88 (m, 3H), 1.65 (m, 2H), 1.50-1.48 (m, 5H), 0.86-0.83 (m, 1H).

Example 8. Preparation of 2-((1R,5S,6R)-3-(8,8-difluoro-2-((S)-2-methylpiperidin-1-yl)-5,6,7,8-tetrahydroquinazolin-4-yl)-3-azabicyclo[3.1.0]hexan-6-yl)acetic acid (Compound 10)

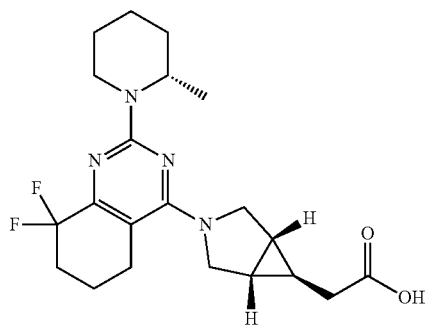 [SMILES: C[C@H]1CCCCN1c1nc(N2C[C@@H]3[C@@H](CC(=O)O)[C@@H]3C2)c2c(n1)C(F)(F)CCC2]

(1) Preparation of methyl 2-((1R,5S,6R)-3-(8,8-difluoro-2-((S)-2-methylpiperidin-1-yl)-5,6,7,8-tetrahydroquinazolin-4-yl)-3-azabicyclo[3.1.0]hexan-6-yl)acetate

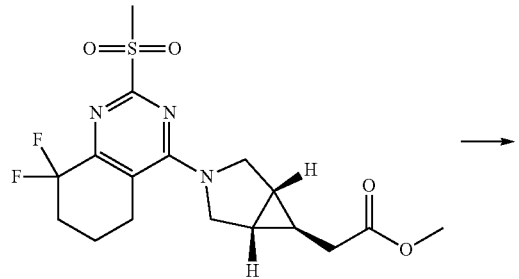

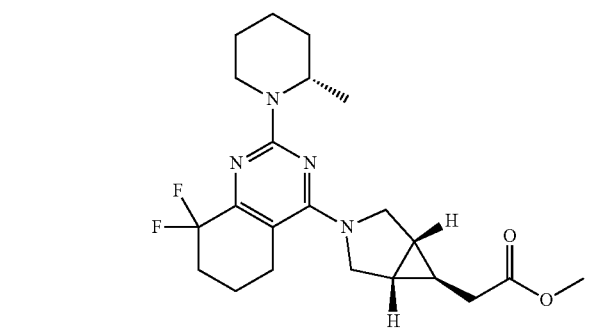

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate (120.0 mg, 0.3 mmol, referring to steps (1)-(10) of example 2 for the preparation method) was dissolved in NMP (3 mL), then added with DIEA (155.0 mg, 1.2 mmol) and (S)-2-methylpiperidine (59.0 mg, 0.6 mmol). Then, the reaction was subjected to microwave at 170° C. for 2 hours, diluted with ethyl acetate, washed with water followed by saturated sodium chloride, dried over anhydrous sodium sulfate, and then subjected to column chromatography (EA/PE=1/5), thus obtaining the product (10.0 mg, yield 7.9%).

(2) Preparation of 2-((1R,5S,6R)-3-(8,8-difluoro-2-((S)-2-methylpiperidin-1-yl)-5,6,7,8-tetrahydroquinazolin-4-yl)-3-azabicyclo[3.1.0]hexan-6-yl)acetic acid

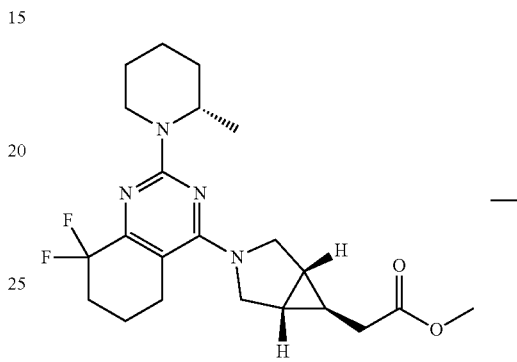

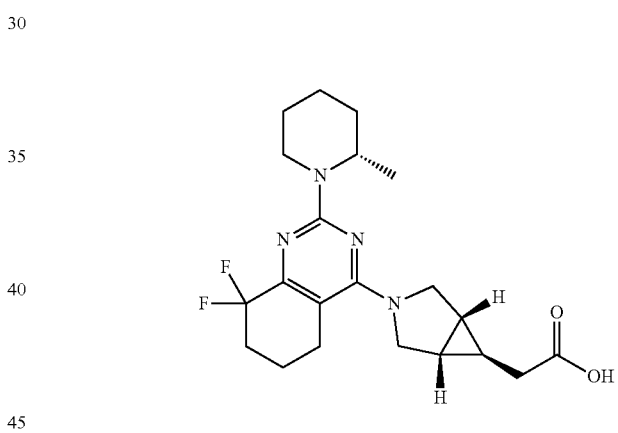

Methyl 2-((1R,5S,6R)-3-(8,8-difluoro-2-((S)-2-methylpiperidin-1-yl)-5,6,7,8-tetrahydroquinazolin-4-yl))-3-azabicyclo[3.1.0]hexan-6-yl)acetate (24.0 mg, 0.057 mmol) was dissolved in THF/H$_2$O (2/2 mL), and then added with NaOH (4.6 mg, 0.11 mmol). The reaction was conducted at 20° C. for 30 min, adjusted to pH6-7, concentrated, and subjected to column chromatography (DCM:MeOH=20:1), thus obtaining the product (7.2 mg, yield: 31.1%).

Molecular formula: $C_{21}H_{28}F_2N_4O_2$; Molecular weight: 406.5 LC-MS (M/e): 407.0 (M+H$^+$)

$^1$H-NMR (400 MHz, CDCl$_3$) δ: 5.03-4.90 (m, 1H), 4.59-4.48 (m, 1H), 4.00-3.76 (m, 2H), 3.64-3.09 (m, 2H), 2.91-2.70 (m, 1H), 2.65-2.57 (m, 2H), 2.47-2.38 (m, 2H), 2.36-2.18 (m, 2H), 1.85-1.75 (m, 2H), 1.75-1.51 (m, 5H), 1.56-1.45 (m, 2H), 1.49-1.40 (m, 1H), 1.39-1.29 (m, 1H), 1.09-1.18 (m, 3H), 0.96-1.08 (m, 1H).

Example 9. Preparation of 2-((1R,5S,6S)-3-(8,8-difluoro-2-((R)-2-methylpiperidin-1-yl)-5,6,7,8-tetrahydroquinazolin-4-yl)-3-azabicyclo[3.1.0]hexan-6-yl)acetic acid (Compound 11)

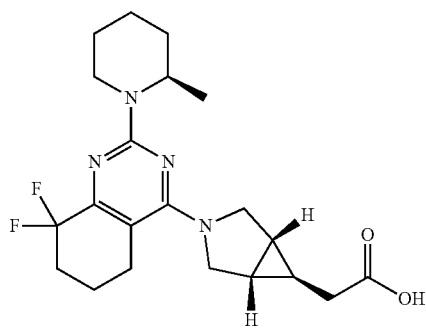 [SMILES: C[C@@H]1CCCCN1c1nc(N2C[C@@H]3[C@@H](CC(=O)O)[C@@H]3C2)c2c(n1)C(F)(F)CCC2]

(1) Preparation of methyl 2-((1R,5S,6S)-3-(8,8-difluoro-2-((R)-2-methylpiperidin-1-yl)-5,6,7,8-tetrahydroquinazolin-4-yl)-3-azabicyclo[3.1.0]hexan-6-yl)acetate

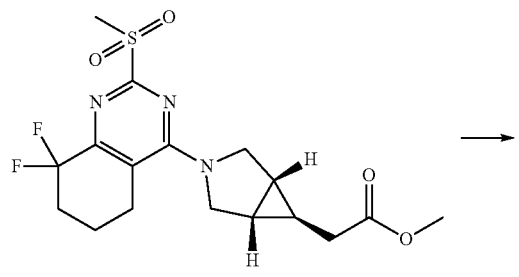

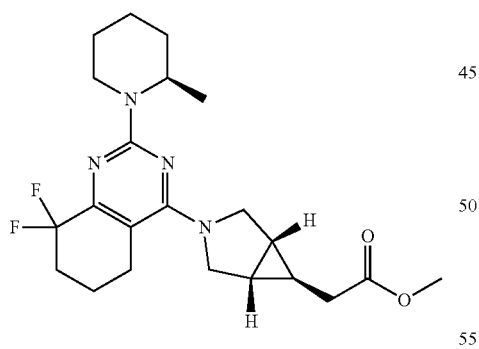

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl)acetate (200 mg, 0.5 mmol) was dissolved in NMP (1 mL), and then added with DIEA (322 mg, 2.5 mmol) and (R)-2-methylpiperidine (99 mg, 1 mmol). Then, the reaction was subjected to microwave at 180° C. for 2 hours, diluted with ethyl acetate, washed with water followed by saturated sodium chloride, dried over anhydrous sodium sulfate, and subjected to column chromatography (EA/PE=1/5), thus obtaining the product (35 mg, yield 17%).

(2) Preparation of 2-((1R,5S,6S)-3-(8,8-difluoro-2-((R)-2-methylpiperidin-1-yl)-5,6,7,8-tetrahydroquinazolin-4-yl)-3-azabicyclo[3.1.0]hexan-6-yl)acetic acid

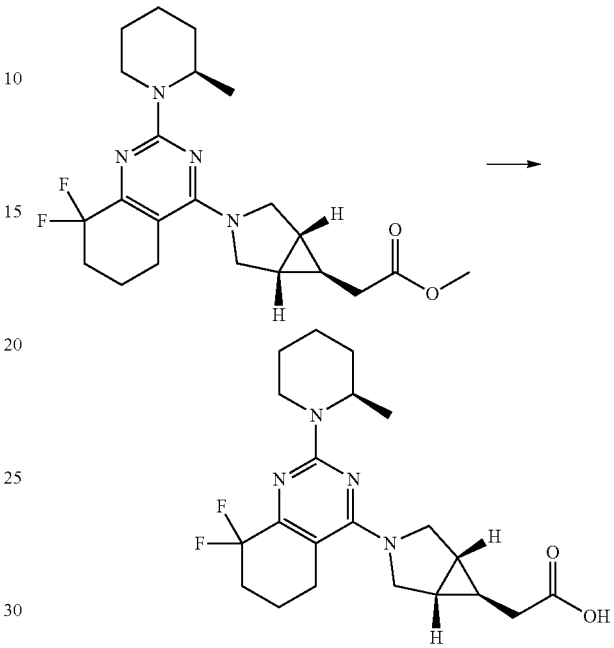

Methyl 2-((1R,5S,6S)-3-(8,8-difluoro-2-((R)-2-methylpiperidin-1-yl)-5,6,7,8-tetrahydroquinazolin-4-yl))-3-azabicyclo[3.1.0]hexan-6-yl)acetate (35 mg, 0.083 mmol) was dissolved in THF/H$_2$O (3/3 mL), and then added with NaOH (17 mg, 0.42 mmol). The reaction was conducted at 20° C. for 3 hours, adjusted to pH 5, concentrated, and subjected to reversed phase column chromatography (ACN/H$_2$O=0-60%), thus obtaining the product (5.9 mg, yield: 17%).

Molecular formula: C$_{21}$H$_{28}$F$_2$N$_4$O$_2$; Molecular weight: 406.5; LC-MS (M/e): 407.2 (M+H$^+$)

$^1$H-NMR (400 MHz, CDCl$_3$) δ: 5.02-4.85 (m, 1H), 4.58-4.42 (m, 1H), 4.00-3.75 (m, 2H), 3.64-3.09 (m, 5H), 2.89-2.70 (m, 1H), 2.65-2.42 (m, 2H), 2.25-1.89 (m, 4H), 1.82-1.15 (m, 7H), 1.09 (m, 3H), 0.8 (s, 1H).

Example 10. Preparation of 2-((1R,5S,6R)-3-(7,7-difluoro-2-((S)-2-methylpiperidin-1-yl)-6,7-dihydro-5H-cyclopenta[d]pyrimidin-4-yl)-3-azabicyclo[3.1.0]hexan-6-yl)acetic acid (Compound 12)

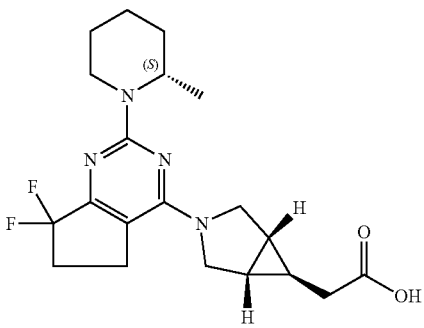

(1) Preparation of methyl 2-((1R,5S,6R)-3-(7,7-difluoro-2-((S)-2-methylpiperidin-1-yl)-6,7-dihydro-5H-cyclopenta[d]pyrimidin-4-yl)-3-azabicyclo[3.1.0]hexan-6-yl)acetate

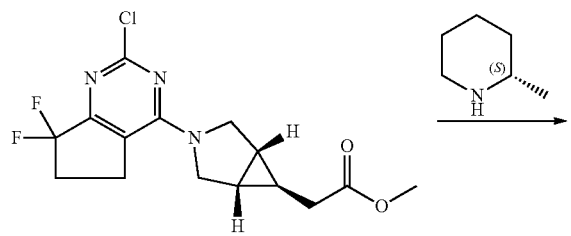

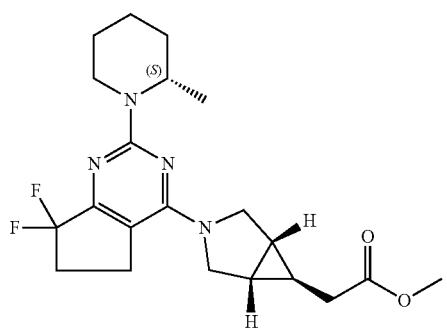

Methyl 2-((1R,5S,6s)-3-(2-chloro-7,7-difluoro-6,7-dihydro-5H-cyclopenta[d]pyrimidin-4-yl)-3-azabicyclo[3.1.0]hexan-6-yl)acetate (80 mg, 0.23 mmol) was dissolved in acetonitrile (2 mL), and added with DIEA (0.5 ml) and (S)-2-methylpiperidine (50 mg, 0.50 mmol). Then, the reaction was subjected to microwave at 90° C. for 6 hours monitored by TLC (petroleum ether:ethyl acetate=2:1), spin-dried, and subjected to preparative thin layer chromatography (petroleum ether:ethyl acetate=2:1), thus obtaining 30 mg of the compound with a yield of 31.9%.

(2) Preparation of 2-((1R,5S,6R)-3-(7,7-difluoro-2-((S)-2-methylpiperidin-1-yl)-6,7-dihydro-5H-cyclopenta[d]pyrimidin-4-yl)-3-azabicyclo[3.1.0]hexan-6-yl)acetic acid

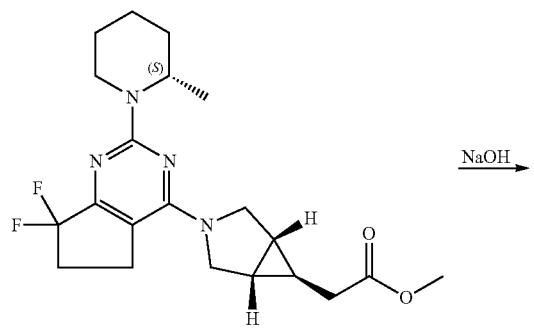

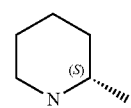

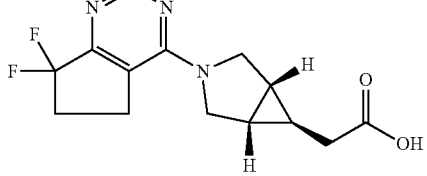

Methyl 2-((1R,5S,6R)-3-(7,7-difluoro-2-((S)-2-methylpiperidin-1-yl)-6,7-dihydro-5H-cyclopenta[d]pyrimidin-4-yl)-3-azabicyclo[3.1.0]hexan-6-yl)acetate (30 mg, 0.07 mmol) was dissolved in MeOH/THF/H$_2$O (2/2/0.2 mL), and added with NaOH (20 mg, 0.5 mmol). The reaction was carried out at 25° C. for 3 hours, adjusted to pH=4-5 with 1N hydrochloric acid, concentrated, and subjected to preparative thin layer chromatography (dichloromethane:methanol=20:1), thus obtaining 20 mg of the compound with yield of 69.0%.

Molecular formula: C$_{20}$H$_{26}$F$_2$N$_4$O$_2$; Molecular weight: 392.4; LC-MS (M/e): 393.0 (M+H$^+$)

$^1$HNMR (400 MHz, MeOD): δ 4.88-5.00 (m, 1H), 4.50-4.54 (m, 1H), 4.02 (dd, J=10.8 Hz, 4.4 Hz, 2H), 3.64-3.67 (m, 2H), 3.03-3.09 (m, 2H), 2.93 (td, J=10.8 Hz, 2.8 Hz, 1H), 2.42-2.49 (m, 2H), 2.32 (d, J=7.2 Hz, 2H), 1.70-1.73 (m, 3H), 1.57-1.67 (m, 4H), 1.42-1.47 (m, 1H), 1.17 (d, J=7.2 Hz, 3H), 0.89-0.92 (m, 1H).

Example 11. Preparation of 2-((1R,5S,6S)-3-(7,7-difluoro-2-((R)-2-methylpiperidin-1-yl)-6,7-dihydro-5H-cyclopenta[d]pyrimidin-4-yl)-3-azabicyclo[3.1.0]hexan-6-yl)acetic acid (Compound 13)

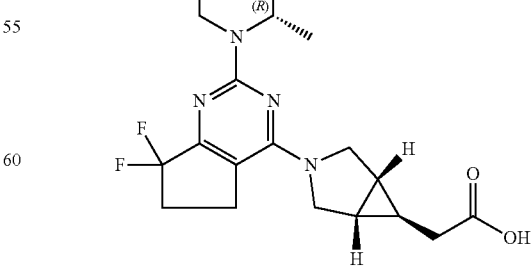

(1) Preparation of 2-((1R,5S,6S)-3-(7,7-difluoro-2-((R)-2-methylpiperidin-1-yl)-6,7-dihydro-5H-cyclopenta[d]pyrimidin-4-yl)-3-azabicyclo[3.1.0]hexan-6-yl)acetate

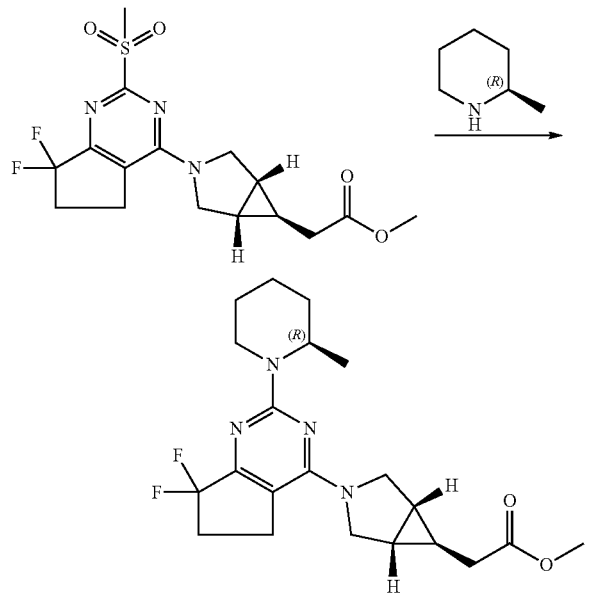

Methyl 2-((1R,5S,6s)-3-(7,7-difluoro-2-(methylsulfonyl)-6,7-dihydro-5H-cyclopenta[d]pyrimidin-4-yl)-3-azabicyclo[3.1.0]hexan-6-yl)acetate (100 mg, 0.26 mmol, referring to Example 1 for the preparation method) was dissolved in NMP (2 mL), and added with DIEA (0.5 ml), 4-dimethylaminopyridine (5 mg, 0.04 mmol), and (R)-2-methylpiperidine (51 mg, 0.51 mmol). Then, the reaction was subjected to microwave at 160° C. for 4 hours, added with water (10 ml), and extracted with 3×5 ml ethyl acetate. Then, the organic phases were combined, spin-dried, and subjected to column chromatography (ethyl acetate:petroleum ether=1:2), thus obtaining 9 mg of the compound with a yield of 8.6%.

(2) Preparation of 2-((1R,5S,6S)-3-(7,7-difluoro-2-((R)-2-methylpiperidin-1-yl)-6,7-dihydro-5H-cyclopenta[d]pyrimidin-4-yl)-3-azabicyclo[3.1.0]hexan-6-yl)acetic acid

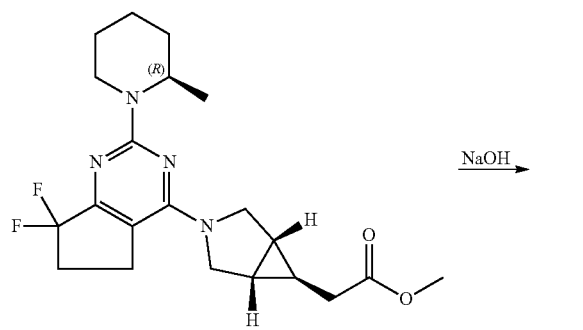

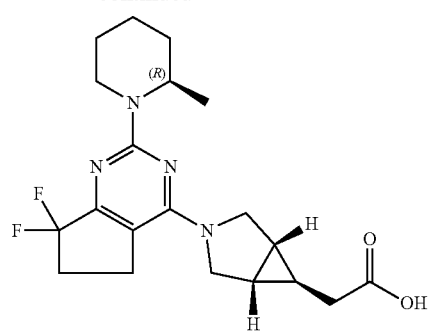

Methyl 2-((1R,5S,6S)-3-(7,7-difluoro-2-((R)-2-methylpiperidin-1-yl)-6,7-dihydro-5H-cyclopenta[d]pyrimidin-4-yl)-3-azabicyclo[3.1.0]hexan-6-yl)acetate (9 mg, 0.022 mmol) was dissolved in MeOH/THF/$H_2O$ (2/2/0.2 mL), and added with NaOH (5 mg, 0.12 mmol). Then, the reaction was conducted at 25° C. for 4 hours, adjusted to pH=6-7 with 1N hydrochloric acid, concentrated, and then subjected to preparative thin layer chromatography (dichloromethane:methanol=20:1), thus obtaining 3.0 mg of the compound with yield of 34.5%.

Molecular formula: $C_{20}H_{26}F_2N_4O_2$; Molecular weight: 392.4; LC-MS (M/e): 393.0 (M+H$^+$)

$^1$HNMR (400 MHz, MeOD): 34.88-5.00 (m, 1H), 4.50-4.54 (m, 1H), 4.01 (dd, J=10.8 Hz, 4.0 Hz, 2H), 3.62-3.65 (m, 2H), 3.02-3.06 (m, 2H), 2.90-2.91 (m, 1H), 2.38-2.43 (m, 2H), 2.29-2.31 (m, 2H), 1.69-1.71 (m, 3H), 1.55-1.60 (m, 4H), 1.28-1.33 (m, 1H), 1.15 (d, J=7.2 Hz, 3H), 0.89-0.92 (m, 1H).

Example 12. Preparation of 2-((1R,5S,6s)-3-(2-(cyclobutyl(methyl)amino)-8,8-difluoro-5,6,7,8-tetrahydroquinazolin-4-yl)-3-azabicyclo[3.1.0]hexan-6-yl)acetic acid (Compound 14)

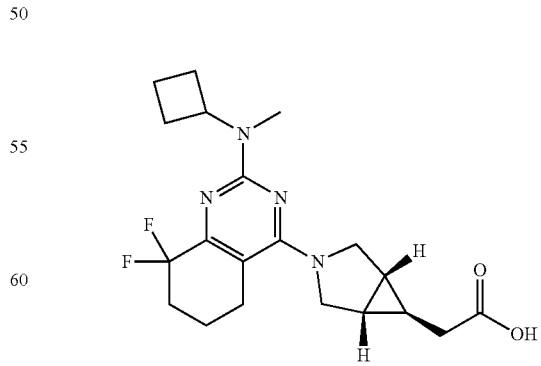

(1) Preparation of methyl 2-((1R,5S,6s)-3-(2-(cyclobutyl(methyl)amino)-8,8-difluoro-5,6,7,8-tetrahydroquinazolin-4-yl)-3-azabicyclo[3.1.0]hexan-6-yl) acetate

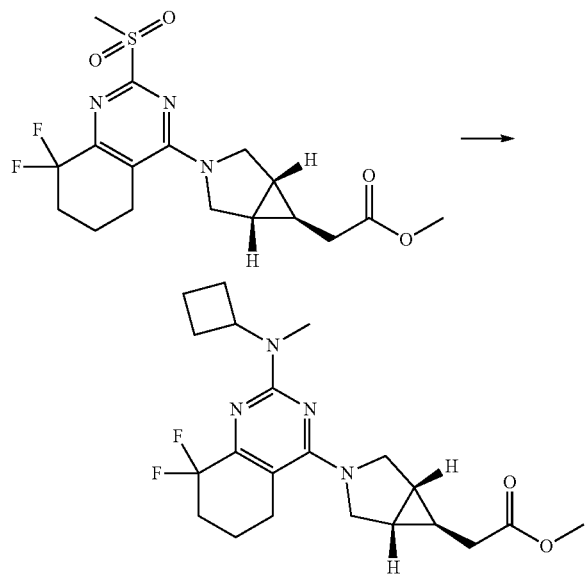

Methyl 2-((1R,5S,6s)-3-(8,8-difluoro-2-(methylsulfonyl)-5,6,7,8-tetrahydroquinazolin-4-yl)-3-azabicyclo[3.1.0]hexan-6-yl) acetate (100 mg, 0.25 mmol) was dissolved in NMP (2 mL), and added with DIEA (161 mg, 1.25 mmol) and N-cyclobutylmethylamine hydrochloride (61 mg, 0.5 mmol). Then, the reaction was subjected to microwave at 160° C. for 2 hours, diluted with ethyl acetate, washed with water followed by saturated sodium chloride, dried over anhydrous sodium sulfate, and then subjected to column chromatography (EA/PE=1/5), thus obtaining the product (30 mg, yield 30%).

(2) Preparation of 2-((1R,5S,6s)-3-(2-(cyclobutyl(methyl)amino)-8,8-difluoro-5,6,7,8-tetrahydroquinazolin-4-yl)-3-azabicyclo[3.1.0]hexan-6-yl)acetic acid

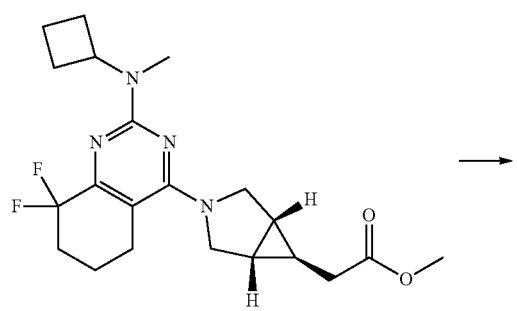

-continued

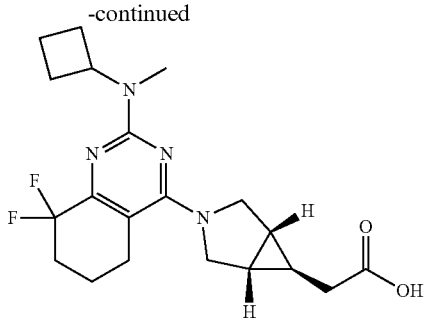

Methyl 2-((1R,5S,6s)-3-(2-(cyclobutyl(methyl)amino)-8, 8-difluoro-5,6,7,8-tetrahydroquinazolin-4-yl))-3-azabicyclo [3.1.0]hexan-6-yl)acetate (30 mg, 0.074 mmol) was dissolved in THF/H$_2$O (3/3 mL), and then added with NaOH (15 mg, 0.37 mmol). The reaction was carried out at 20° C. for 3 hours, adjusted to pH 5, concentrated, and subjected to reversed phase column chromatography (ACN/H$_2$O=0-80%), thus obtaining the product (5.9 mg, yield: 20%). Molecular formula: C$_{20}$H$_{26}$F$_2$N$_4$O$_2$; Molecular weight: 392.45; LC-MS (M/e): 393.2 (M+H$^+$)

$^1$H-NMR (400 MHz, CDCl$_3$) δ: 5.11-4.95 (m, 1H), 3.99-3.85 (m, 2H), 3.55-3.41 (m, 2H), 3.02 (s, 3H), 2.95-2.48 (m, 5H), 2.25-2.12 (m, 6H), 1.83-1.55 (m, 4H), 1.39-1.28 (m, 2H), 0.89 (s, 1H).

Example 13. Preparation of 2-((1R,5S,6s)-3-(8,8-difluoro-2-(1-methyl-1H-1,2,3-triazol-5-yl)-5,6,7,8-tetrahydroquinazolin-4-yl)-3-azabicyclo[3.1.0]hexan-6-yl)acetic acid (Compound 15)

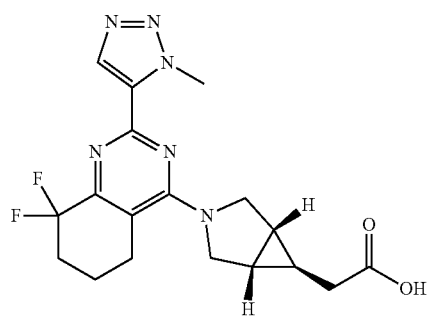 [SMILES: Cn1nncc1-c1nc(N2C[C@@H]3[C@@H](CC(=O)O)[C@@H]3C2)c2c(n1)C(F)(F)CCC2]

(1) Preparation of 8,8-difluoro-2-(methylthio)-5,6,7,8-tetrahydroquinazolin-4-ol

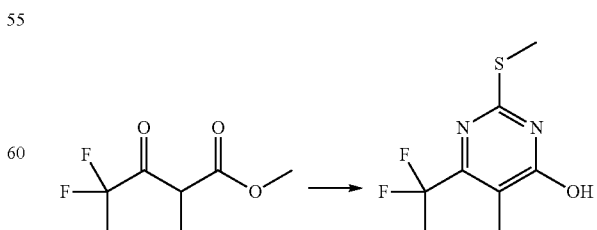

Methyl 3,3-difluoro-2-oxocyclohexane-1-carboxylate (2.0 g, 10.4 mmol) was dissolved in water (50 mL), and added with methyl isothiourea (2.2 g, 15 mmol) and sodium carbonate (2.2 g, 20.8 mmol). Then, the reaction was carried out at 20° C. for 16 hours, adjusted to an acidic pH by adding diluted hydrochloric acid, and extracted with EA. The organic layer was dried over anhydrous sodium sulfate, and distilled under reduced pressure, thus obtaining the product for direct use in the next step of reaction.

(2) Preparation of 8,8-difluoro-5,6,7,8-tetrahydro-quinazoline-2,4-diol

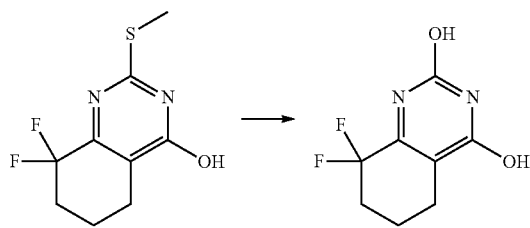

8,8-difluoro-2-(methylthio)-5,6,7,8-tetrahydroquinazolin-4-ol (1.8 g of the crude product) was dissolved in ethanol (40 mL) and added with 6M HCl (40 ml). After the addition was completed, the reaction was carried out at 85° C. for 8 hours. The reaction, after completed, was then directly spin-dried, thus obtaining the product for use in the next step of reaction.

(3) Preparation of 2,4-dichloro-8,8-difluoro-5,6,7,8-tetrahydroquinazoline

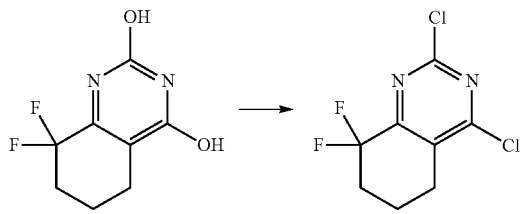 [SMILES: Oc1nc(O)c2c(n1)C(F)(F)CCC2 ; FC1(F)CCCc2c(Cl)nc(Cl)nc21]

8,8-difluoro-5,6,7,8-tetrahydroquinazoline-2,4-diol (1.6 g of the crude product) was dissolved in phosphorus oxychloride (50 mL), and added with DIPEA (5 ml). After the addition was completed, the reaction was carried out at 110° C. for 16 hours. The reaction, after completed, was directly spin-dried and purified by column chromatography (EA:PE=1:5), thus obtaining 1.5 g of the product with a three-step yield of 61%.

(4) Preparation of methyl 2-((1R,5S,6s)-3-(2-chloro-8,8-difluoro-5,6,7,8-tetrahydroquinazolin-4-yl)-3-azabicyclo[3.1.0]hexan-6-yl) acetate

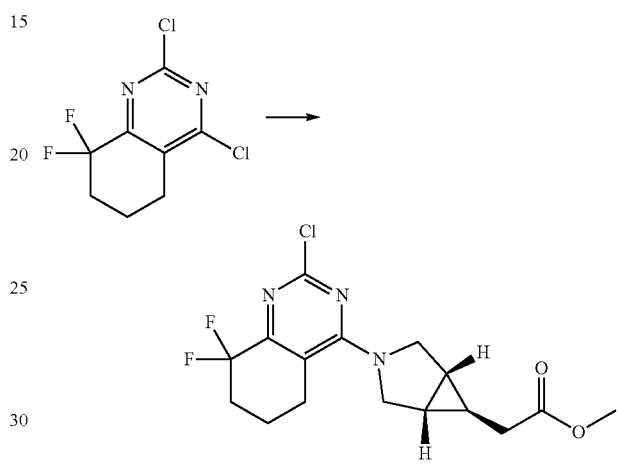

2,4-dichloro-8,8-difluoro-5,6,7,8-tetrahydroquinazoline (500.0 mg, 2.1 mmol) was dissolved in acetonitrile (10 ml), and added with methyl 2-((1R,5S,6s)-3-azabicyclo[3.1.0]hexan-6-yl)acetate (391.0 mg, 2.5 mmol) and DIPEA (1.9 ml, 10.5 mmol). Then the reaction was carried out at 25° C. for 16 hours. The reaction, after completed, was spin-dried and subjected to normal phase column chromatography (EA:PE=1:2), thus obtaining 640 mg of the product with a yield of 85%.

(5) Preparation of methyl 2-((1R,5S,6s)-3-(8,8-difluoro-2-(1-methyl-1H-1,2,3-triazol-5-yl)-5,6,7,8-tetrahydroquinazolin-4-yl)-3-azabicyclo[3.1.0]hexan-6-yl)acetate

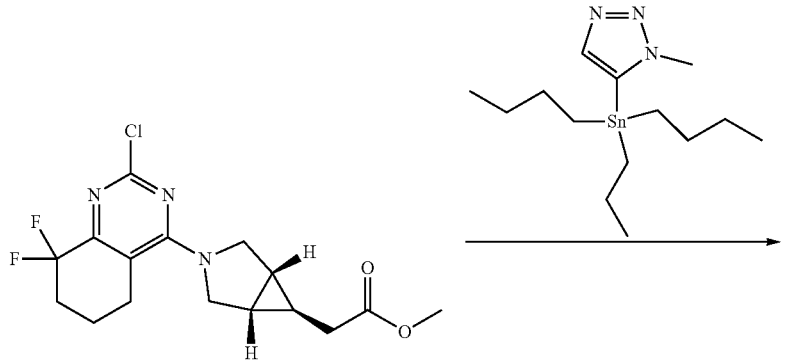

-continued

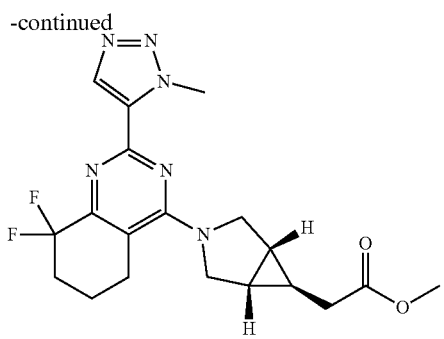

Methyl 2-((1R,5S,6s)-3-(2-chloro-8,8-difluoro-5,6,7,8-tetrahydroquinazolin-4-yl)-3-azabicyclo [3.1.0]hexan-6-yl)acetate (320.0 mg, 0.9 mmol) was dissolved in dioxane (10 ml), and added with 1-methyl-5-(tributylstannyl)-1H-1,2,3-triazole (368.0 mg, 0.99 mmol), Pd(pph$_3$)Cl$_2$ (19.0 mg, 0.027 mmol) and x-phos (13.0 mg, 0.027 mmol). After the addition was completed, the reaction was carried out at 100° C. for 16 hours under N$_2$ protection. After completed, the reaction was cooled to 20° C., spin-dried and subjected to normal phase column chromatography (EA:PE=2:1), thus obtaining 220 mg of the product with a yield of 60%.

(6) Preparation of 2-((1R,5S,6s)-3-(8,8-difluoro-2-(1-methyl-1H-1,2,3-triazol-5-yl)-5,6,7,8-tetrahydroquinazolin-4-yl)-3-azabicyclo[3.1.0]hexan-6-yl)acetic acid

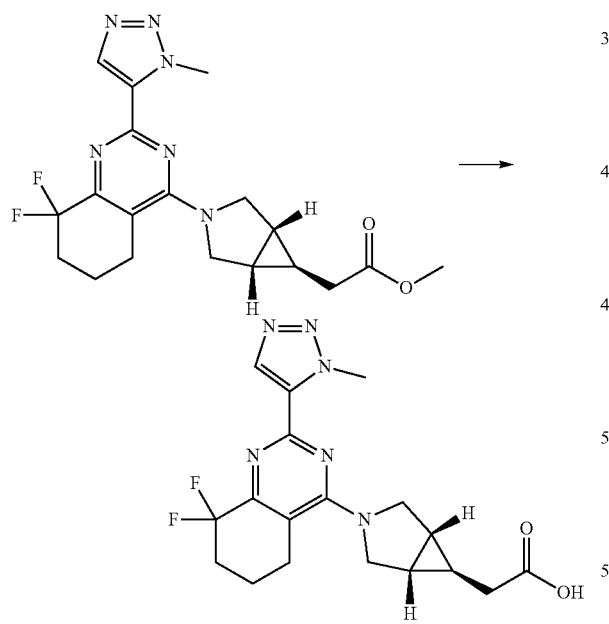

Methyl 2-((1R,5S,6s)-3-(8,8-difluoro-2-(1-methyl-1H-1,2,3-triazol-5-yl)-5,6,7,8-tetrahydroquinazolin-4-yl)-3-azabicyclo[3.1.0]hexan-6-yl)acetate (200.0 mg, 0.5 mmol) was dissolved in THF (4 ml) and H$_2$O (4 ml), and added with NaOH (30.0 mg, 0.75 mmol). After the addition was completed, the reaction was carried out at 25° C. for 2 hours. After completed, the reaction was adjusted to an acidic pH, and filtered, thus obtaining 150 mg of the product with a yield of 77%.

Molecular formula: $C_{18}H_{20}F_2N_6O_2$; Molecular weight: 390.4; LC-MS (M/e): 391.0 (M+H$^+$)

$^1$H-NMR (400 MHz, DMSO) δ: 8.19 (s, 1H), 4.38 (s, 3H), 4.07 (d, J=11.2 Hz, 2H), 3.78 (d, J=10.4 Hz, 2H), 2.94 (s, 2H), 2.31-2.24 (m, 4H), 1.82 (s, 2H), 1.60 (s, 2H), 0.85-0.83 (m, 1H).

Example 14. Preparation of 2-((1R,5S,6s)-3-(7,7-difluoro-2-(1-methyl-1H-1,2,3-triazol-5-yl)-6,7-dihydro-5H-cyclopenta[d]pyrimidin-4-yl)-3-azabicyclo[3.1.0]hexan-6-yl)acetic acid (Compound 16)

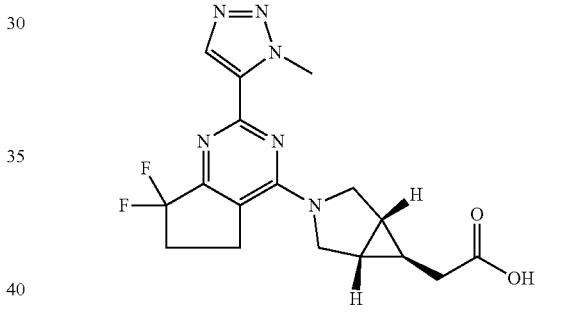

(1) Preparation of 1-methyl-5-(tributylstannyl)-1H-1,2,3-triazole

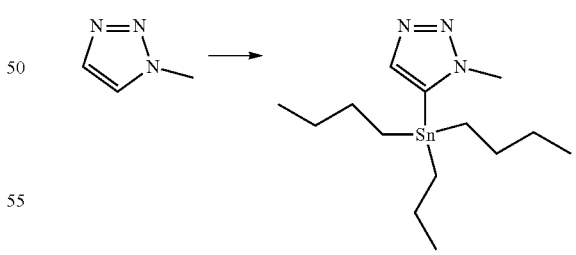

1-methyl-1H-1,2,3-triazole (300.0 mg, 3.6 mmol) was dissolved in THF (5 mL), added with n-BuLi (2.0 ml, 5 mmol) and allowed to react at −78° C. for 2 hours, and then added with tributyltin chloride (1.1 ml, 4 mmol) and allowed to react at −78° C. for 1 hour. After that, the reaction was heated to 20° C. for 1 hour, then spin-dried directly, added with petroleum ether, and filtered. The filtrate was distilled under reduced pressure, thus obtaining 1.5 g of the crude product for direct use in the next step of reaction.

(2) Preparation of methyl 2-((1R,5S,6s)-3-(7,7-difluoro-2-(1-methyl-1H-1,2,3-triazol-5-yl)-6,7-dihydro-5H-cyclopenta[d]pyrimidin-4-yl)-3-azabicyclo[3.1.0]hexan-6-yl) acetate

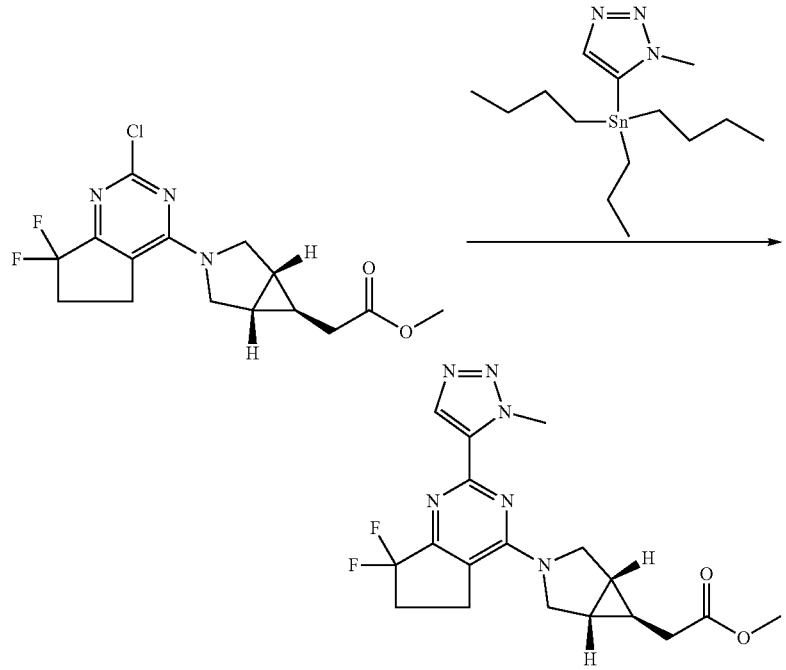

Methyl 2-((1R,5S,6s)-3-(2-chloro-7,7-difluoro-6,7-dihydro-5H-cyclopenta[d]pyrimidin-4-yl)-3-azabicyclo[3.1.0]hexan-6-yl)acetate (70.0 mg, 0.2 mmol) was dissolved in dioxane (2 mL), and added with 1-methyl-5-(tributylstannane)-1H-1,2,3-triazole (82.0 mg of the crude product), Pd(pph$_3$)$_2$Cl$_2$ (4.2 mg, 0.006 mmol) and x-phos (2.9 mg, 0.006 mmol). After the addition was completed, the reaction was conducted under N$_2$ protection at 100° C. for 3 hours. After completed, the reaction was filtered, and washed with methanol. The filtrate was distilled under reduced pressure and purified by preparative thin layer chromatography (DCM:MeOH=20:1), thus obtaining 71 mg of the product with a yield of 91%.

(3) Preparation of 2-((1R,5S,6s)-3-(7,7-difluoro-2-(1-methyl-1H-1,2,3-triazol-5-yl)-6,7-dihydro-5H-cyclopenta[d]pyrimidin-4-yl)-3-azabicyclo[3.1.0]hexan-6-yl)acetic acid

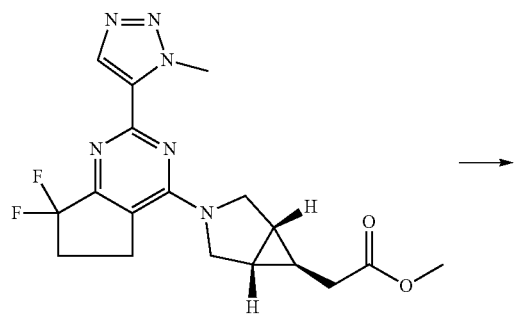

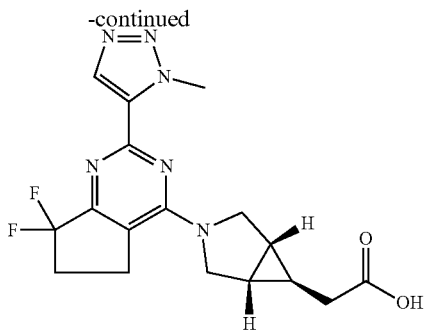

Methyl 2-((1R,5S,6s)-3-(7,7-difluoro-2-(1-methyl-1H-1,2,3-triazol-5-yl)-6,7-dihydro-5H-cyclopenta[d]pyrimidin-4-yl)-3-azabicyclo[3.1.0]hexan-6-yl) acetate (100.0 mg, 0.26 mmol) was dissolved in THF (3 mL) and H$_2$O (3 mL), and added with NaOH (16.0 mg, 0.39 mmol). The reaction was carried out at 20° C. for 2 hours, adjusted to an acidic pH, and extracted with EA. The organic phase was distilled under reduced pressure, thus obtaining a solid, which was then washed with methanol and obtained 53 mg of the product with a yield of 54%.

Molecular formula: C$_{17}$H$_{18}$F$_2$N$_6$O$_2$; Molecular weight: 376.37; LC-MS (M/e): 377.0 (M+H$^+$).

$^1$H-NMR (400 MHz, MeOD) δ: 8.29 (s, 1H), 4.48 (s, 3H), 4.16 (d, J=11.2 Hz, 2H), 3.91-3.69 (m, 2H), 3.31 (t, J=1.6 Hz, 2H), 2.57-2.54 (m, 2H), 2.35 (d, J=7.2 Hz, 2H), 1.67 (s, 2H), 0.96-0.94 (m, 1H).

The KHK inhibitors provided by the present invention and their uses are described in detail in the above. The principles and embodiments of the present application are

What is claimed is:

1. A compound represented by general formula (I), a pharmaceutically acceptable salt, an ester, or a stereoisomer thereof:

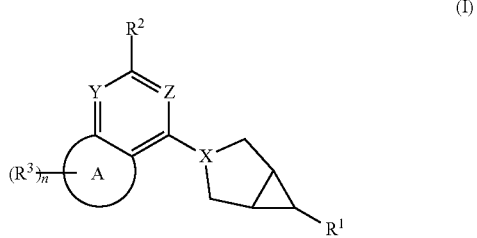

(I)

wherein,

X, Y, and Z are each —N—;

ring A is a 4-7 membered cycloalkyl;

$R^1$ is selected from hydrogen, halogen, nitro group, cyano group, -(L)$_m$-C(O)OR$^a$, -(L)$_m$-CONR$^a$R$^b$, -(L)$_m$-CONHSO$_2$R$^a$, -(L)$_m$-SO$_2$R$^a$, -(L)$_m$-SO$_2$NHCOR$^a$, -(L)$_m$-OR$^a$, -(L)$_m$-SR$^a$, -(L)$_m$-NR$^a$R$^b$, -(L)$_m$-C(O)R$^a$, -(L)$_m$-OC(O)R$^a$, -(L)$_m$-OC(O)OR$^a$, -(L)$_m$-OC(O)NR$^a$R$^b$, -(L)$_m$-NR$^a$C(O)R$^b$, -(L)$_m$-NR$^a$C(O)OR$^b$, -(L)$_m$-OS(O)R$^a$, -(L)$_m$-OS(O)OR$^a$, -(L)$_m$-OS(O)NR$^a$R$^b$, -(L)$_m$-S(O)NR$^a$R$^b$, -(L)$_m$-NR$^a$S(O)R$^b$, -(L)$_m$-OS(O)$_2$R$^a$, -(L)$_m$-S(O)$_2$NR$^a$R$^b$, -(L)$_m$-NR$^a$S(O)$_2$R$^b$; and the following groups optionally substituted with one or more Q1 groups: -(L)$_m$-C$_{1-6}$ alkyl, -(L)$_m$-C$_{1-6}$ alkoxy, -(L)$_m$-C$_{3-12}$ cycloalkyl, -(L)$_m$-C$_{3-12}$ heterocyclyl, -(L)$_m$-C$_{6-12}$ aryl, and -(L)$_m$-C$_{5-12}$ heteroaryl;

L is selected from C$_{1-6}$ alkylene and haloC$_{1-6}$ alkylene;

$R^2$ is selected from the following groups optionally substituted by one or more Q2 groups: 3-12 membered heterocyclic group, 3-12 membered cycloalkyl group, 5-12 membered heteroaryl, 6-12 membered aryl, 5-12 membered spirocyclic group, 5-12 membered spiro heterocyclic group, 5-12 membered bridged group, 5-12 membered bridged heterocyclic group, N(C$_{1-6}$ alkyl)$_2$, N(C$_{1-6}$ alkyl)(C$_{3-8}$ cycloalkyl), NH(C$_{1-6}$ alkyl), and NH(C$_{3-8}$ cycloalkyl);

each $R^3$ is independently selected from hydrogen, halogen, nitro group, cyano group, amino group, hydroxyl, carboxy; and the following groups optionally substituted with one or more Q3 groups: C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-12 membered cycloalkyl group, 3-12 membered heterocyclic group, 6-12 membered aryl, and 5-12 membered heteroaryl;

each of $R^a$ and $R^b$ is independently selected from hydrogen, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, and halo C$_{1-6}$ alkoxy;

each of Q1, Q2, Q3 and Q4 groups is independently selected from hydroxyl, amino group, halogen, nitro group, cyano group, carboxy, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-10 membered cycloalkyl group, 3-10 membered heterocyclic group, 6-10 membered aryl, and 5-10 membered heteroaryl; and m and n are each independently an integer from 0 to 8.

2. The compound, the pharmaceutically acceptable salt, the ester or the stereoisomer thereof according to claim 1, wherein, X, Y, and Z are each —N—;

ring A is a 4-7 membered cycloalkyl;

$R^1$ is selected from hydrogen, halogen, nitro group, cyano group, -(L)$_m$-C(O)OR$^a$, -(L)$_m$-CONR$^a$R$^b$, -(L)$_m$-CONHSO$_2$R$^a$, -(L)$_m$-SO$_2$R$^a$, -(L)$_m$-SO$_2$NHCOR$^a$, -(L)$_m$-OR$^a$, -(L)$_m$-SR$^a$, -(L)$_m$-NR$^a$R$^b$, -(L)$_m$-C(O)R$^a$, -(L)$_m$-OC(O)R$^a$, -(L)$_m$-OC(O)OR$^a$, -(L)$_m$-OC(O)NR$^a$R$^b$, -(L)$_m$-NR$^a$C(O)R$^b$, -(L)$_m$-NR$^a$C(O)OR$^b$, -(L)$_m$-OS(O)R$^a$, -(L)$_m$-OS(O)OR$^a$, -(L)$_m$-OS(O)NR$^a$R$^b$, -(L)$_m$-S(O)NR$^a$R$^b$, -(L)$_m$-NR$^a$S(O)R$^b$, -(L)$_m$-OS(O)$_2$R$^a$, -(L)$_m$-S(O)$_2$NR$^a$R$^b$, -(L)$_m$-NR$^a$S(O) 2R$^b$; and the following groups optionally substituted with one or more Q1 groups: -(L)$_m$-C$_{1-6}$ alkyl, -(L)$_m$-C$_{1-6}$ alkoxy, -(L)$_m$-C$_{3-10}$ cycloalkyl, -(L)$_m$-C$_{3-10}$ heterocyclyl, -(L)$_m$-C$_{6}$-10 aryl, and -(L)$_m$-C$_{5-10}$ heteroaryl;

L is selected from C$_{1-6}$ alkylene and halo C$_{1-6}$ alkylene;

$R^2$ is selected from the following groups optionally substituted by one or more Q2 groups: 3-8 membered heterocyclic group, 3-8 membered cycloalkyl group, 5-10 membered heteroaryl, 6-10 membered aryl, 5-10 membered spirocyclic group, 5-10 membered spiro heterocyclic group, 5-10 membered bridged group, 5-10 membered bridged heterocyclic group, N(C$_{1-6}$ alkyl) 2, N(C$_{1-6}$ alkyl)(C$_{3-8}$ cycloalkyl), NH(C$_{1-6}$ alkyl), and NH(C$_{3-8}$ cycloalkyl);

each $R^3$ is independently selected from hydrogen, halogen, nitro group, cyano group, amino group, hydroxyl, carboxy; and the following groups optionally substituted with one or more Q3 groups: C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, halo C$_{1-6}$ alkoxy, 3-10 membered cycloalkyl group, 3-10 membered heterocyclic group, 6-10 membered aryl, and 5-10 membered heteroaryl;

each of $R^a$ and $R^b$ is independently selected from hydrogen, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, and halo C$_{1-6}$ alkoxy;

each of Q1, Q2, Q3 and Q4 groups is independently selected from hydroxyl, amino group, halogen, nitro group, cyano group, carboxy, C$_{1-6}$ alkyl, C$_{1-6}$ alkoxy, C$_{1-6}$ alkylamino, di(C$_{1-6}$ alkyl)amino, halo C$_{1-6}$ alkyl, hydroxy C$_{1-6}$ alkyl, amino C$_{1-6}$ alkyl, and halo C$_{1-6}$ alkoxy; and m and n are each independently an integer from 0 to 6.

3. The compound, the pharmaceutically acceptable salt, the ester or the stereoisomer thereof according to claim 2, wherein, X, Y, and Z are each —N—;

ring A is a 4-7 membered cycloalkyl;

$R^1$ is selected from hydrogen, halogen, nitro group, cyano group, -(L)$_m$-C(O)OR$^a$, -(L)$_m$-CONR$^a$R$^b$, -(L)$_m$-CONHSO$_2$R$^a$, -(L)$_m$-SO$_2$R$^a$, -(L)$_m$-SO$_2$NHCOR$^a$, -(L)$_m$-OR$^a$, -(L)$_m$-NR$^a$R$^b$, -(L)$_m$-C(O)R$^a$, -(L)$_m$-OC(O)R$^a$, -(L)$_m$-NR$^a$C(O)R$^b$, -(L)$_m$-NR$^a$C(O)OR$^b$, -(L)$_m$-OS(O) 2R$^a$, -(L)$_m$-S(O)$_2$NR$^a$R$^b$, -(L)$_m$-NR$^a$S(O)$_2$R$^b$, and the following groups optionally substituted with one or more Q1 groups: $-(L)_m-C_{1-4}$ alkyl, and $-(L)_m-C_{1-4}$ alkoxy;

L is selected from $C_{1-4}$ alkylene and halo $C_{1-4}$ alkylene;

$R^2$ is selected from the following groups optionally substituted by one or more Q2 groups: 3-8 membered heterocyclic group, 3-8 membered cycloalkyl group, 5-10 membered heteroaryl, 6-10 membered aryl, 5-10 membered spirocyclic group, 5-10 membered spiro heterocyclic group, $N(C_{1-4}$ alkyl) 2, $N(C_{1-4}$ alkyl)($C_{3-6}$ cycloalkyl), $NH(C_{1-4}$ alkyl), and $NH(C_{3-6}$ cycloalkyl);

each $R^3$ is independently selected from hydrogen, halogen, nitro group, cyano group, amino group, hydroxyl, carboxy, and the following groups optionally substituted with one or more Q3 groups: $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy;

each of $R^a$ and $R^b$ is independently selected from hydrogen, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy;

each of Q1, Q2, Q3, and Q4 groups is independently selected from hydroxyl, amino group, halogen, nitro group, cyano group, carboxy, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy; and m and n are each independently an integer from 0 to 6.

4. The compound, the pharmaceutically acceptable salt, the ester or the stereoisomer thereof according to claim 3, wherein, X, Y, and Z are each —N—;

ring A is a 4-7 membered cycloalkyl;

$R^1$ is selected from $-(L)_m-C(O)OR^a$, $-(L)_m-CONR^aR^b$, $-(L)_m-CONHSO_2R^a$, $-(L)_m-SO_2R^a$, $-(L)_m-SO_2NHCOR^a$, $-(L)_m-OR^a$, $-(L)_m-NR^aR^b$, $-(L)_m-C(O)R^a$, $-(L)_m-OC(O)R^a$, $-(L)_m-NR^aC(O)R^b$, $-(L)_m-NR^aC(O)OR^b$, $-(L)_m-OS(O) 2R^a$, $-(L)_m-S(O)_2NR^aR^b$, $-(L)_m-NR^aS(O)_2R^b$, and the following groups optionally substituted with 1-4 Q1 groups: $-(L)_m-C_{1-4}$ alkyl, and $-(L)_m-C_{1-4}$ alkoxy;

L is selected from $C_{1-3}$ alkylene and halo $C_{1-3}$ alkylene;

$R^2$ is selected from the following groups optionally substituted by 1-4 Q2 groups: 3-6 membered heterocyclic group, 3-6 membered cycloalkyl group, 5-10 membered heteroaryl, 6-10 membered aryl, 5-8 membered spirocyclic group, 5-8 membered spiro heterocyclic group, and $N(C_{1-4}$ alkyl)($C_{3-6}$ cycloalkyl);

each $R^3$ is independently selected from hydrogen, halogen, nitro group, cyano group, amino group, hydroxyl, carboxy, and the following groups optionally substituted with 1-4 Q3 groups: $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy;

each of $R^a$ and $R^b$ is independently selected from hydrogen, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy;

each of Q1, Q2, Q3, and Q4 groups is independently selected from hydroxyl, amino group, halogen, nitro group, cyano group, carboxy, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl, and halo $C_{1-4}$ alkoxy; and m and n are each independently an integer from 0 to 4.

5. The compound, the pharmaceutically acceptable salt, the ester or the stereoisomer thereof according to claim 4, wherein, X, Y, and Z are each —N—;

ring A is a 4-7 membered cycloalkyl;

$R^1$ is selected from $-(L)_m-C(O)OR^a$, $-(L)_m-CONR^aR^b$, $-(L)_m-SO_2R^a$, $-(L)_m-OR^a$, $-(L)_m-NR^aR^b$, $-(L)_m-C(O)R^a$, $-(L)_m-OC(O)R^a$, $-(L)_m-NR^aC(O)R^b$, $-(L)_m-S(O)_2NR^aR^b$, $-(L)_m-NR^aS(O)_2R^b$, and the following groups optionally substituted with 1-3 Q1 groups: $-(L)_m-C_{1-4}$ alkyl, and $-(L)_m-C_{1-4}$ alkoxy;

L is $C_{1-3}$ alkylene;

$R^2$ is selected from the following groups optionally substituted by 1-4 Q2 groups: 3-6 membered heterocyclic group, 5-8 membered spiro heterocyclic group, 5-8 membered heteroaryl, and $N(C_{1-4}$ alkyl)($C_{3-6}$ cycloalkyl);

each $R^3$ is independently selected from hydrogen, halogen, nitro group, cyano group, amino group, hydroxyl, and carboxy;

each of $R^a$ and $R^b$ is independently selected from hydrogen and $C_{1-4}$ alkyl;

each of Q1 and Q2 groups is independently selected from hydroxyl, amino group, halogen, nitro group, cyano group, carboxy; $C_{1-4}$ alkyl, $C_{1-4}$ alkoxy, $C_{1-4}$ alkylamino, di($C_{1-4}$ alkyl)amino, halo$C_{1-4}$ alkyl, hydroxy $C_{1-4}$ alkyl, amino $C_{1-4}$ alkyl, and halo $C_{1-4}$ alkoxy; and m and n are each independently an integer from 0 to 3.

6. The compound, the pharmaceutically acceptable salt, the ester or the stereoisomer thereof according to claim 5, wherein, X, Y and Z are each —N—;

ring A is a 4-7 membered cycloalkyl;

$R^1$ is selected from $-(L)_m-C(O)OR^a$, $-(L)_m-CONR^aR^b$, $-(L)_m-SO_2R^a$, $-(L)_m-OR^a$, $-(L)_m-NR^aR^b$, $-(L)_m-C(O)R^a$, and the following groups optionally substituted with 1-3 Q1 groups: $-(L)_m-C_{1-4}$ alkyl, and $-(L)_m-C_{1-4}$ alkoxy;

L is methylene;

$R^2$ is selected from the following groups optionally substituted by 1-3 Q2 groups: oxetanyl, azetidinyl, tetrahydrofuranyl, tetrahydrothienyl, pyrrolidinyl, imidazolidinyl, oxazolidinyl, thiazolidinyl, piperidinyl, piperazinyl, morpholinyl, furyl, pyranyl, pyrrolyl, thienyl, thiazolyl, isothiazolyl, thiadiazolyl, imidazolyl, pyrazolyl, oxazolyl, isoxazolyl, oxadiazolyl, triazolyl, tetrazolyl, pyridyl, pyrimidinyl, pyrazinyl, pyridazinyl, triazinyl, tetrazinyl,

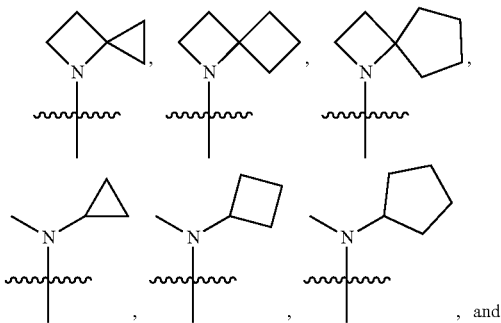

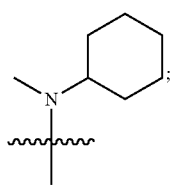

each R³ is independently selected from hydrogen, halogen, nitro group, cyano group, amino group, hydroxyl, and carboxy;

each of Rᵃ and Rᵇ is independently selected from hydrogen, methyl, ethyl, propyl, isopropyl, butyl, isobutyl, sec-butyl, and tert-butyl;

each of Q1 and Q2 groups is independently selected from hydroxyl, amino group, fluorine, chlorine, bromine, iodine, nitro group, cyano group, carboxy, methyl, ethyl, propyl, isopropyl, butyl, isobutyl, sec-butyl, tert-butyl, methoxy, ethoxy, propoxy, methylamino, dimethylamino, trifluoromethyl, and trifluoromethoxy; and m and n are each independently 0, 1, 2, or 3.

7. A compound, or a pharmaceutically acceptable salt, an ester, or a stereoisomer thereof, wherein the compound is selected from:

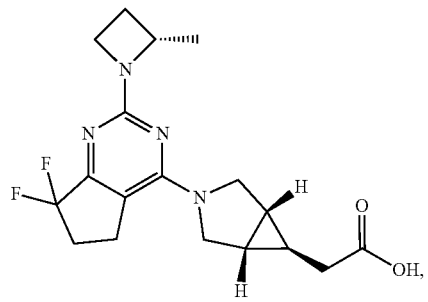

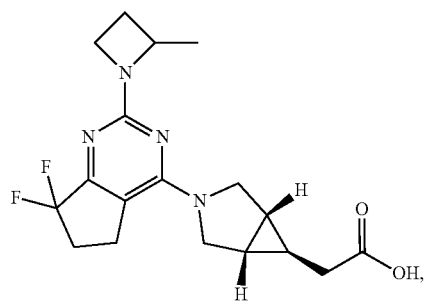

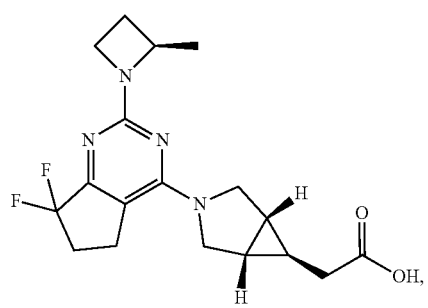

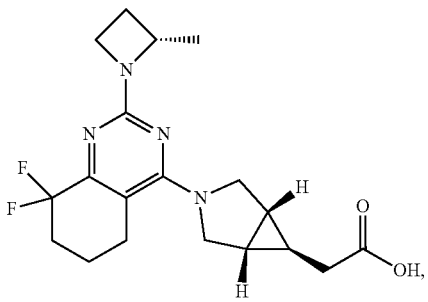

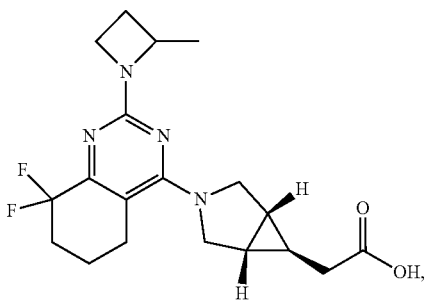

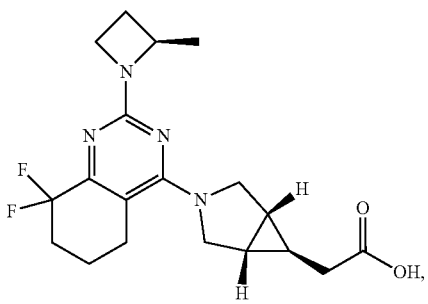

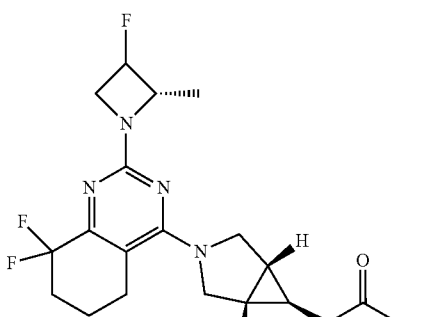

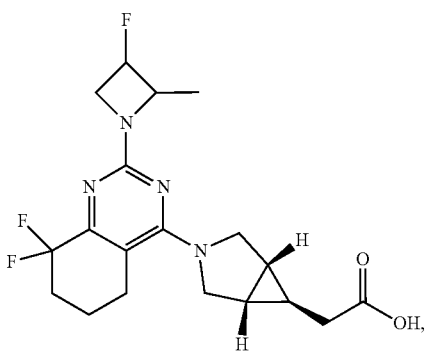

89
-continued
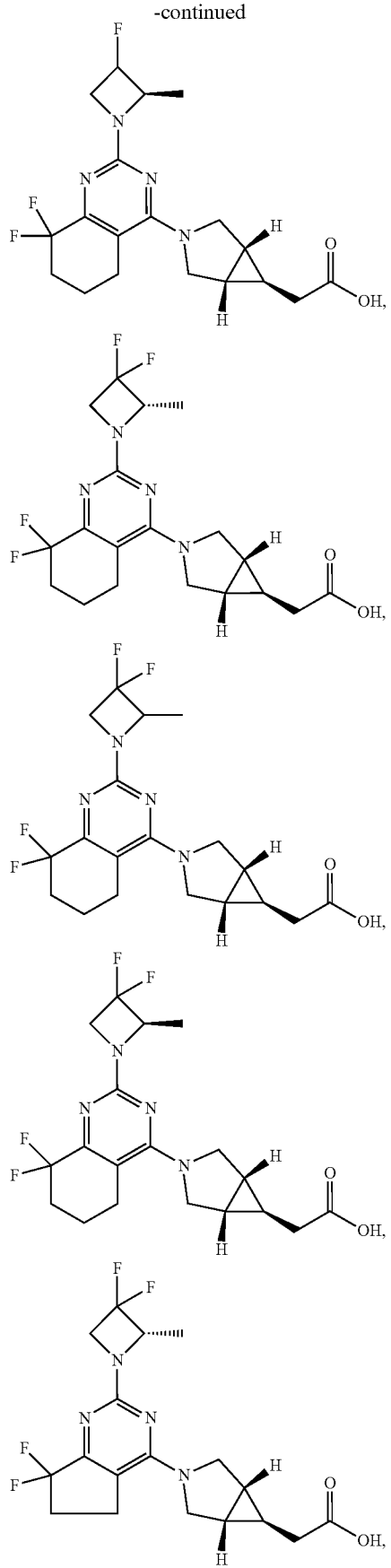
90
-continued
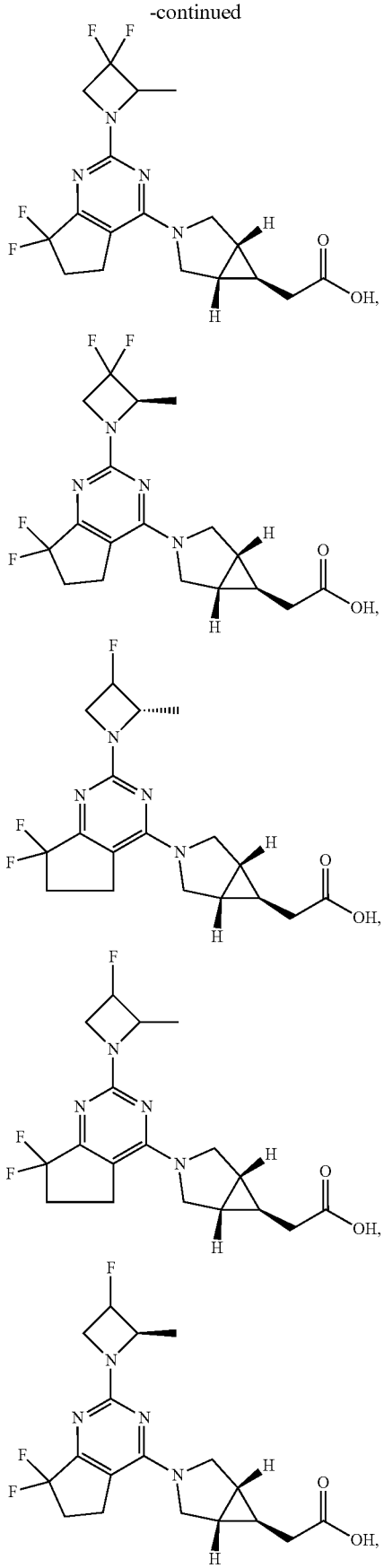

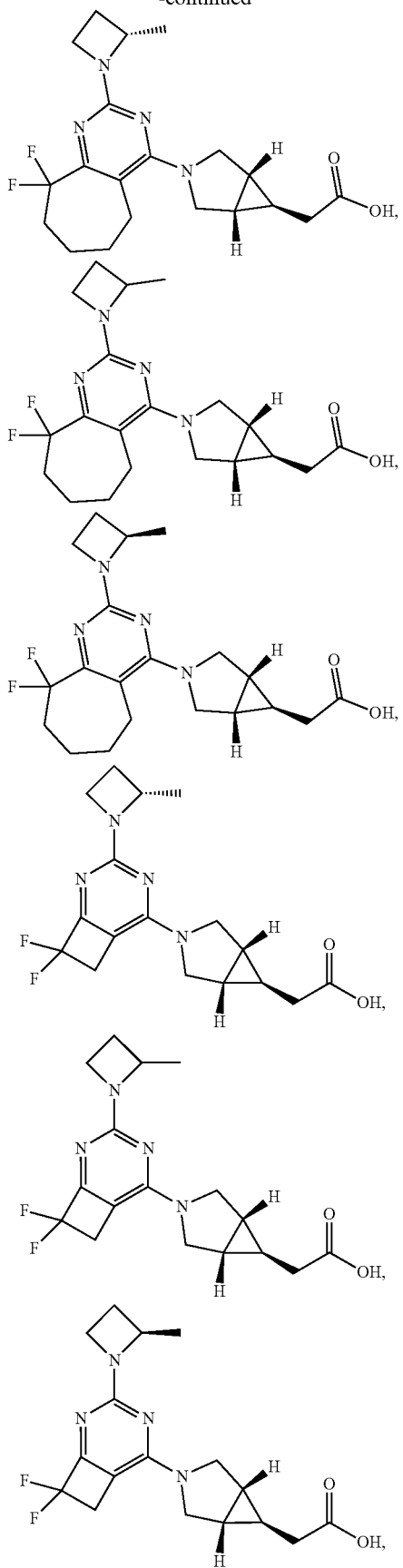
-continued
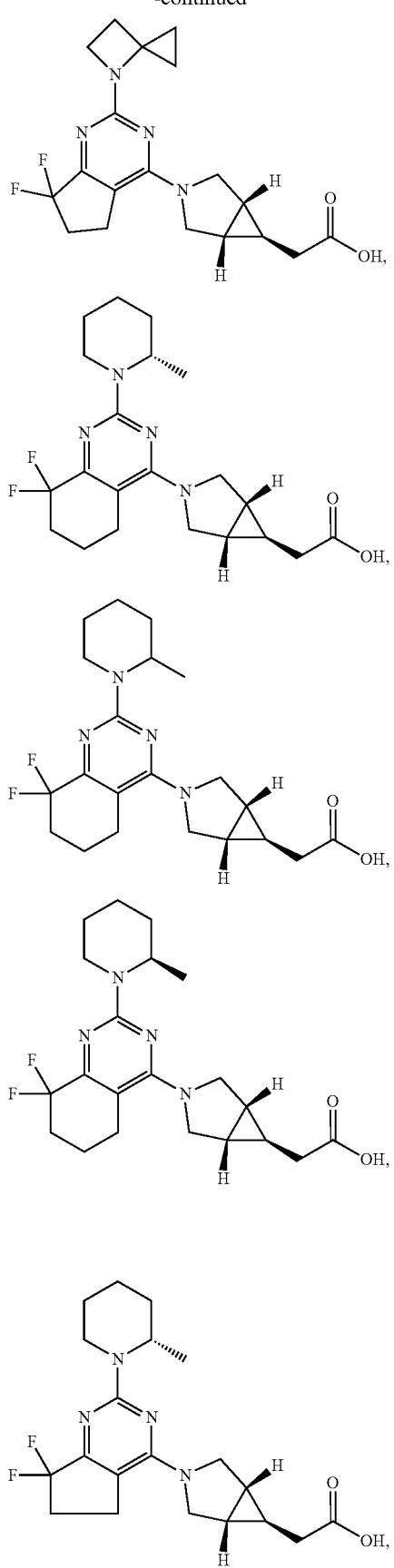
-continued

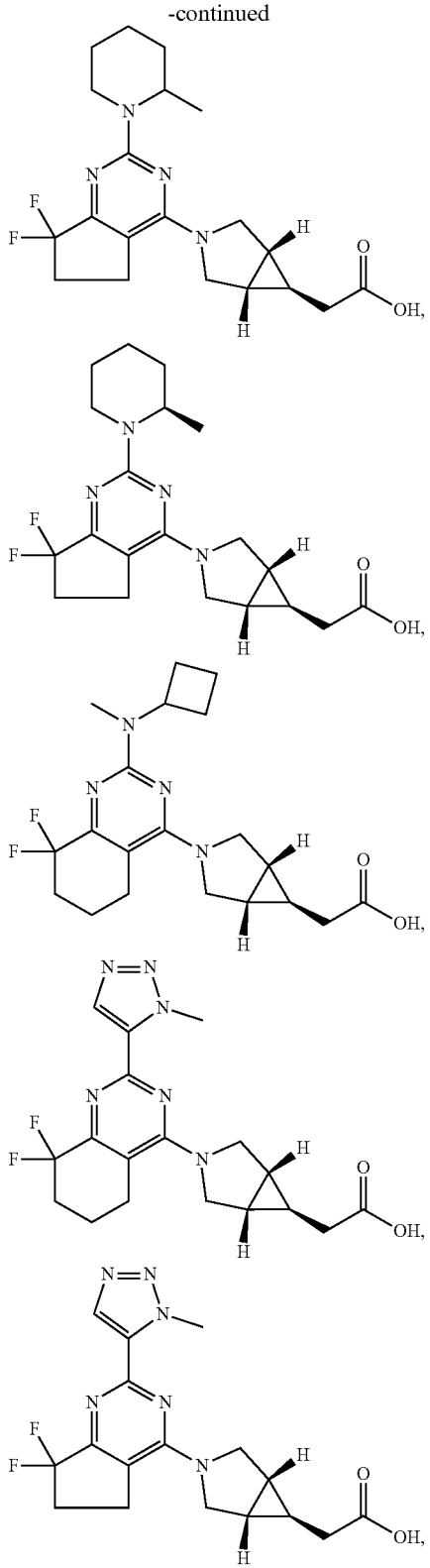

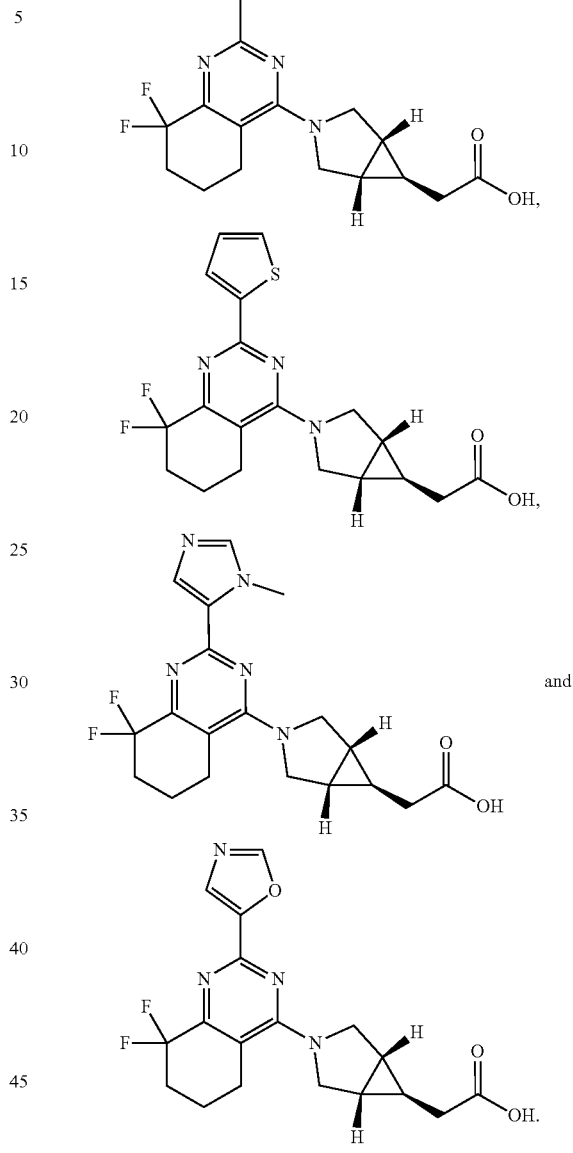

and

8. A pharmaceutical formulation comprising the compound, the pharmaceutically acceptable salt, the ester, or the stereoisomer thereof according to claim 1, and one or more pharmaceutically acceptable carriers and/or diluents, wherein the pharmaceutical formulation is in any dosage form that is clinically or pharmaceutically acceptable.

9. A pharmaceutical composition comprising the compound, the pharmaceutically acceptable salt, the ester, or the stereoisomer thereof according to claim 1, one or more second therapeutic agents; and optionally one or more pharmaceutically acceptable carriers and/or diluents.

* * * * *